US006800604B2

(12) United States Patent
Gurney et al.

(10) Patent No.: US 6,800,604 B2
(45) Date of Patent: Oct. 5, 2004

(54) POLYPEPTIDES THAT INHIBIT HUMAN SERUM-INDUCED CLEAVAGE OF HEPATOCYTE GROWTH FACTOR

(75) Inventors: Austin L. Gurney, Belmont, CA (US); Daniel K. Kirchhofer, Los Altos, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 105 days.

(21) Appl. No.: 09/742,201

(22) Filed: Dec. 19, 2000

(65) Prior Publication Data

US 2002/0123091 A1 Sep. 5, 2002

Related U.S. Application Data

(60) Provisional application No. 60/253,665, filed on Nov. 28, 2000.

(30) Foreign Application Priority Data

Feb. 11, 2000 (WO) ............................... PCT/US00/03565
Mar. 15, 2000 (WO) ............................... PCT/US00/06884

(51) Int. Cl.$^7$ ......................... C07K 14/00; A61K 38/00

(52) U.S. Cl. ........................... 514/2; 530/300; 530/350; 514/12; 424/85.1; 424/198.1

(58) Field of Search ................................. 530/300, 350, 530/351; 514/2, 12; 424/85.1, 184.1, 192.1, 198.1

(56) References Cited

U.S. PATENT DOCUMENTS

| | | |
|---|---|---|
| 4,736,866 A | 4/1988 | Leder et al. |
| 4,873,191 A | 10/1989 | Wagner et al. |
| 5,573,762 A | 11/1996 | Ferrara et al. |
| 5,610,134 A | 3/1997 | Clark et al. |
| 5,624,806 A | 4/1997 | Baker et al. |
| 5,650,282 A | 7/1997 | Keating et al. |
| 5,661,122 A | 8/1997 | Clark et al. |
| 5,773,223 A | 6/1998 | Shyamala et al. |
| 5,773,414 A | 6/1998 | Cody et al. |
| 5,935,924 A | 8/1999 | Bunting et al. |

FOREIGN PATENT DOCUMENTS

| | | |
|---|---|---|
| EP | 0 759 467 A | 2/1997 |
| WO | 97/12629 | 4/1997 |
| WO | 01/05972 A1 | 1/2001 |

OTHER PUBLICATIONS

Falkenberg et al. Expression of a functional proteinase inhibitor capable of accepting xylose: bikunin. Arch Biochem Biophys 387(1):99–106, 2001.*

Kataoka et al. Hepatocyte growth factor activator inhibitor type 1 is a specific cell surface binding protein of hepatocyte growth factor activator (HGFA) and regulates HGFA activity in the pericellular microenvironment.J Biol Chem 275(51):40453–40462,2000.*

Hamasuna et al. Reduced expression of hepatocyte growth factor activator inhibitor type–2/placental bikunin (HAI–2/PB) in human glioblastomas: implication for anti–invasive role of HAI–2/PB in glioblastoma cells. Int J Cancer 93: 339–3435, 2001.*

Adamis et al., "Inhibition of Vascular Endothelial Growth Factor Prevents Retinal Ischemia–Associated Iris Neovascularization in a Nonhuman Primate" *Arch. Opthalmology* 114(1):66–71 (1996).

Aiello et al., "Vascular endothelial growth factor in ocular fluid of patients with diabetic retinopathy and other retinal disorders" *New England J. of Medicine* 331(22):1480–1487 (1994).

Berkman et al., "Expression of the vascular permeability factor/vascular endothelial growth factor gene in central nervous system neoplasms" *J. Clin. Invest.* 91(1):153–159 (1993).

Betocchi et al., "Effects of Diltiazem on left ventricular systolic and diastolic function in hypertrophic cardiomyopathy" *Am. J. Cardiol.* 78:451–457 (1996).

Boznak, M. *Can. J. Biochem. Physiol.* 33:985–994 (1955).

Bonow et al., "Verapamil–induced improvement in left ventricular diastolic filling and increased exercise tolerance in patients with hypertrophic cardiomyopathy: short– and long–term effects" *Circulation* 72:853–864 (1985).

Borgstrom et al., "Complete inhibition of angiogenesis and growth of microtumors by anti–vascular endothelial growth factor neutralizing antibody: novel concepts of angiostatic therapy from intravital videomicroscopy" *Cancer Research* 56(17):4032–4039 (1996).

(List continued on next page.)

*Primary Examiner*—Elizabeth Kemmerer
*Assistant Examiner*—Bridget E. Bunner
(74) *Attorney, Agent, or Firm*—Paul Naik; Craig Svoboda

(57) ABSTRACT

Compositions and methods are disclosed for stimulating or inhibiting angiogenesis and/or cardiovascularization in mammals, including humans. Pharmaceutical compositions are based on polypeptides or antagonists thereto that have been identified for one or more of these uses. Disorders that can be diagnosed, prevented, or treated by the compositions herein include trauma such as wounds, various cancers, and disorders of the vessels including atherosclerosis and cardiac hypertrophy. In addition, the present invention is directed to novel polypeptides and to nucleic acid molecules encoding those polypeptides. Also provided herein are vectors and host cell comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

27 Claims, 5 Drawing Sheets

OTHER PUBLICATIONS

Bradham et al., "Connective Tissue Growth Factor: a Cysteine–rich Mitogen Secreted by Human Vascular Endothelial Cells Is Related to the SRC–induced Immediate Early Gene Product CEF–10" *Journal of Cell Biology* 114:1285–1294 (1991).

Bradley, "Production and Analysis of Chimaeric Mice" *Teratocarcinomas and Embryonic Stem Cells: A Practical Approach*, E. J. Robertson, ed., IRL, Oxford, Chapter 5, pps. 113–151 (1987).

Brown and Vaughan, "Angiotensin–Converting Enzyme Inhibitors" *Circulation* 97:1411–1420 (1998).

Brown et al., "Expression of vascular permeability factor (vascular endothelial growth factor) and its receptors in adenocarcinomas of the gastrointestinal tract" *Cancer Research* 53(19):4727–4735 (1993).

Brown et al., "Expression of vascular permeability factor (vascular endothelial growth factor) and its receptors in breast cancer" *Human Pathology* 26(1):86–91 (1995).

Burgess and Maciag, "The Heparin–Binding (Fibroblast) Growth Factor Family of Proteins" *Annu. Rev Biochem.* 58: 575–606 (1989).

The Consensus Trial Study Group, "Effects of Enalapril on Mortality in Severe Congestive Heart Failure" *New England J. of Medicine* 316 (23):1429–1435 (1987).

The Captopril Multicenter Research Group, "A Placebo–Controlled Trial of Captopril in Refractory Chronic Congestive Heart Failure" *JACC* 2(4):755–763 (1983).

The Captopril–Digoxin Multicenter Research Group, "Comparative Effects of Therapy with Captopril and Digoxin in Patients with Mild to Moderate Heart Failure" *Journal of the American Medical Assn.* 259(4):539–544 (1988).

Cheng et al., "Relationship between the inhibition constant ($K_I$) and the concentration of inhibitor which causes 50 per cent inhibition ($I_{50}$) of an enzymatic reaction" *Biochem. Pharmacol* 22:3099–3108 (1973).

Chien et al., "Regulation of Cardiac Gene Expression During Myocardial Growth and Hypertrophy: Molecular Studies of an Adaptive Physiology Response" *FASEB Journal* 5:3037–3046 (1991).

Chien et al., "Transcriptional Regulation During Cardiac Growth and Development" *Annu. Rev. Physiol* 55:77–95 (1993).

Clapp et al., "The 16–kilodalton N–terminal fragment of human prolactin is a potent inhibitor of angiogenesis" *Endocrinology* 133(3):1292–1299 (1993).

Clemmons et al., "Cultured Fibroblast Monolayers Secrete a Protein That Alters the Cellular Binding of Somatomedin–C/Insulinlike Growth Factor I" *J. Clin. Invest.* 77:1548 1556 (1986).

Cohn et al., "A Comparison of Enalapril with Hydralazine–Isosorbide Dinitrato in the Treatment of Chronic Congestive Heart Failure" *New England J. of Medicine* 325(5):303–310 (1991).

Connolly et al., "Human Vascular Permeability Factor" *Journal of Biological Chemistry* 264(33):20017 20024 (1989).

Delco et al., "Cell Surface Antigens of Chemically Induced Sarcomas of the Mouse" *Journal of Experimental Medicine* 146:720–734 (1977).

Drobin et al., "Inhibition of Tumor Growth By a Monoclonal Antibody Reactive With an Oncogene–Encoded Tumor Antigen" *Proc. Natl. Acad. Sci* 83:9129–9133 (1986).

Dunn et al., "The Cleavage and Formation of Activated Human Hageman Factor by Autodigestion and by Kallikrein" *Journal of Biology Chemistry* 257:1779–1784 (1982).

Dvorak et al., "Vascular permeability factor/vascular endothelial growth factor, microvascular hyperpermeability, and angiogenesis" *American Journal of Pathology* 146(5):1029–1039 (1995).

Englestein and Mertz, "New Method for Assessing Epidermal Wound Healing: The Effects of Triamcinolone Acetonide and Polyethelene Film Occlusion" *J. Invest. Dermatol.* 71:382 384 (1978).

Eichhorn, E., "Restoring Function in Failing Hearts: The Effects of Beta Blockers" *American Journal of Medicine* 104:163–169 (1998).

Ferrara and Davis–Smyth., "The Biology of Vascular Endothelial Growth Factor." *Endocrine Reviews.* 18(1):4–25 (1997).

Ferrara and Henzel, "Pituitary Follicular Cells Secrete a Novel Heparin–binding Growth Factor Specific for Vascular Endothelial Cells" *Biochem. & Biophys. Res. Comm.* 161(2):851–858 (1989).

Ferrara et al., "Molecular and biological properties of the vascular endothelial growth factor family of proteins" *Endo. Rev.* 13:18–32 (1992).

Ferrara et al., "The vascular endothelial growth factor family of polypeptides" *J. Cell Biochem.* 47:211–218 (1991).

Folkman and Shing, "Angiogenesis" *Journal of Biological Chemistry* 267:10931–10934 (1992).

Folkman et al., "Induction of angiogenesis during the transition from hyperplasia to neoplasia" *Nature* 339(6219):58–61 (1989).

Found et al. *J. Am. Coll. Cardiol.* 4:1500–1506 (1984).

Getrans Database, Accession No. BC004140, "Serine portease inhibitor, Kunitz type 1—*Homo sapiens*" (blast results) (Direct Submission Mar. 1, 2001).

Geneseq Patent Database, Accession No. P_B19553, "Human hepatocyte growth factor activator inhibitor–1 (HAI–1) Homo sapiens" (blast results) (Mar. 1, 2001).

Geneseq Patent Database, Accession No. P_W27368, "Hepatocyte growth factor activator inhibitor—*Homo sapiens*" (blast results) (Feb. 26, 1997).

Geneseq Patent Database, Accession No. P W63684, "Human secreted protein 4—*Homo sapiens*" (blast results) (Jun. 18, 1998).

Geneseq Patent Database, Accession No. P_W92653, "Human HAT–1 protein—*Homo sapiens*" (blast results) (Feb. 9, 1999).

Garner, A., "Vascular Diseases" *Pathobiology of Ocular Disease, A Dynamic Approach*, Garner, A., Klintworth GK Eds., 2nd edition, NY:Marcel Dekker pps. 1625–1710 (1994).

Gohda et al., "Purification and Partial Characterization of Hepatocyte Growth Factor from Plasma of a Patient with Fulminant: Hepatic Failure" *J. Clin. Invest.* 81:414–419 (1988).

Good et al., "A tumor suppressor–dependent inhibitor of angiogenesis is immunologically and functionally indistinguishable from a fragment of thrombospondin" *Proc. Natl. Acad. Sci. USA* 87(17):6624–6628 (1990).

Harada et al., "Pressure Overload Induces Cardiac Hypertrophy in Angiotensin II Type IA Receptor Knockout Mice" *Circulation* 97:1952–1959 (1998).

Harrison et al., "Effects of beta adrenergic blockade on the circulation, with particular reference to observations in patients with hypertrophic subaortic stenosis" *Circulation* 29:84–98 (1964).

Hartford et al., "Diastolic Function of the Heart in Untreated Primary Hypertension" *Hypertension* 6:329–338 (1984).

Homey, C., "Signalling Hypertrophy: How Many Switches, How Many Wires" *Circulation* 97:1890–1892 (1998).

Horak et al., "Angiogenesis, assessed by platelet/endothelial cell adhesion molecule antibodies, as indicator of node metastases and survival in breast cancer" *Lancet* 340(8828):1120–1124 (1992).

Houck et al., "The Vascular Endothelial Growth Factor Family: Identification of a Fourth Molecular Species and Characterization of Alternative Splicing of RNA." *Mol. Endocrinol.* 5:1806 1814 (1991).

Igawa et al., "Hepatocyte Growth Factor is a Potent Mitogen for Cultured Rabbit Renal Tubular Epithelial Cells" *Biochem. & Biophys. Res. Comm* 174(2):831–838 (Jan. 31, 1991).

Inoue et al., "The Human Endothelin Family: Three Structurally and Pharmacologically Distinct Isopeptides Predicted by Three Separate Genes" *Proc. Natl. Acad. Sci. USA* 86:2863–2867 (Apr. 1989).

Inouye et al., "Failure of Antihypertensive Therapy with Diuretic, Beta–Blocking and Calcium Channel–Blocking Drugs to Consistently Reverse Left Ventricular Diastolic Filling Abnormalities" *Am. J. Cardiol.* 53:1583–1587 (1984).

Ishikawa et al., "Identification of Angiogenic Activity and the Cloning and Expression of Platelet–Derived Endothelial Cell Growth Factor." *Nature.* 338:557–562 (1989).

Joloit et al., "Proviral Rearrangements and Overexpression of a New Cellular Gene (nov) in Mycloblastosis–Associated Virus Type 1 induced Nephroblastomas" Mol. Cell Biol. 12:10–21 (1992).

Kan et al., "Hepatocyte growth factor/hepatopoietin A stimulates the growth of rat kidney proximal tubule epithelial cells (RPTE), rat nonparenchymal liver cells, human melonoma cells, mouse keratinocytes and stimulates anchorage–independent growth of SV–40 transformed RPTE" *Biochem. & Biophys.*

Karmali et al., "Prostaglandins in breast cancer: Relationship to disease stage and hormone status" *Br. J. Cancer* 48:689–696 (1983).

Katz, A.M., "Scientific insights from clinical studies of converting–enzyme inhibitors in the failing heart" *Trends Cardiovasc. Med* 5(1):37–44 (1995).

Kock et al., "Vascular Permeability Factor, An Endothelial Cell Mitogen Related to PDGF" *Science* 246:1309–1312 (1989).

Koyt et al., "A Faster–Acting and More Potent Form of Tissue Plasminogen Activator." *Proc. Natl. Acad. Sci USA* 91:3670–3674 (1994).

Kim et al., "Inhibition of Vascular Endothelial Growth Factor Induced Angiogenesis Suppresses Tumour Growth in vivo" *Nature* 362:841–844 (1993).

Klagsbrun and D'Amore, "Regulators of angiogenesis" *Ann. Rev. Physiol* 53:217–239 (1991).

Kramer et al., "Controlled Trial of Captopril on Chronic Heart Failure: A Rest and Exercise Hemodynamic Study" *Circulation* 67(4):807–816 (1983).

Kurzrock et al., "LIF: Not Just a Leukemia Inhibitory Factor" *Endocrine Reviews* 12(3):208–217 (1991).

Lai et al., "Prostaglandin $E_{2\alpha}$ induces cardiac myocyte hypertrophy in vitro and cardiac growth in vivo" *Am. J. Physiol.* (*Heart Circ. Physiol.*) 271:H2197–H2208 (1996).

Lakco et al., "Targeted Oncogene Activation by Site–Specific Recombination in Transgenic Mice," *Proc. Natl. Acad Sci. USA.* 89:6232–6236 (Jul 1992).

Lau and Nathans, "Genes induced by serum growth factors" *The Hormonal Control of Gene Transcription* (Series: Molecular Aspects of Cellular Regulation), P. Cohen & J.G. Foulkes, NY:Elsevier Science Publishers vol. 6:257–293 (1991).

Lavitrano et al., "Sperm Cells as Vectors for Introducing Foreign DNA into Eggs: Genetic Transformation of Mice" *Cell.* 57:717 723 (1989).

Leung et al., "Vascular Endothelial Growth Factor is a Secreted Angiogenic Mitogen" *Science* 246:1306–1309 (1989).

Li et al., "Targeted Mutation of the DNA Methyltransferase Gene Results in Embryonic Lethality." *Cell.* 69:915–926 (Jun 1992).

Lo, C.W., "Transformation by Iontophoretic Microinjection of DNA: Multiple integrations Without, Tandem Insertions" *Mol. Cell Biol.* 3(10):1803 1814 (Oct 1983).

Lopez et al., "Transdifferentiated retinal pigment epithelial cells are immunoreactive for vascular endothelial growth factor in surgically excised age–related macular degeneration–related choroidal neovascular membranes" *Invest. Ophthalmol. Vis. Sci.* 37(b):855–868 (1996).

Lorell et al., "Modification of abnormal left ventricular diastolic properties by nitedipine in patients with hypertrophic cardiomyopathy" *Circulation* 65:499–507 (1982).

Louie and Edwards, "Hypertrophic Cardiomyopathy" *Prog Cardiovasc. Dis.* 36:275–308 (1994).

Macchiarini et al., "Relation of neovascularisation to metastasis of non–small–cell lung cancer" *Lancet* 340 (8812):145–146 (1992).

Marian and Roberts, "Recent Advances in the Molecular Genetics of Hypertrophic Cardiomyopathy" *Circulation* 92:1336–1347 (1995).

Maron et al., "Hypertrophic Cardiomyopathy: Interrelations of Clinical Manifestations, Pathophysiology, and Therapy" *New England J. of Medicine* 316:780–789 (1987).

Mosaic, B., "Heart Failure 1997: a time to take stock" *Curr. Op. in Cardiology* 12:209–217 (1997).

Matsumoto et al., "Hepatocyte Growth Factor is a Potent Stimulator of Human Melanocyte DNA Synthesis and Growth" *Biochem & Biophys Res Comm.* 176(1):45–51 (Apr. 15, 1991).

Mattern et al., "Association of vascular endothelial growth factor expression with intratumoral microvessel density and tumour cell proliferation in human epidermoid lung carcinoma" *Brit. J Cancer* 73(7):931–934 (1996).

McInyk et al., "Vascular endothelial growth factor promotes tumor dissemination by a mechanism distinct from its effect on primary tumor growth" *Cancer Research* 56(4):921–924 (1996).

Metcalf, D., "Leukemia Inhibitory Factor—A Puzzling Polyfunctional Regulator" *Growth Factors* 7:169–173 (1992).

Michalopoulos, G.K., "Liver regeneration: molecular mechanism of growth control" *FASEB Journal* 4:176 187 (1990).

Miyazawa et al., "Molecular Cloning and Sequence Analysis of the cDNA for a Human Serine Protease Responsible for Activation of Hepatocyte Growth Factor" *Journal of Biological Chemistry* 268:10024–10028 (1993).

Miyazawa et al., "Proteolytic Activation of Hepatocyte Growth Factor in Response to Tissue Injury" Journal *of Biological Chemistry* 269:8966–8970 (1994).

Montesano et al., "Identification of a Fibroblast–Derived Epithelial Morphogen as Hepatocyte Growth Factor" *Cell* 67:901–908 (Nov. 29, 1991).

Morgan and Baker, "Cardiac Hypertrophy, Mechanical, Neural and Endocrine Dependence" *Circulation* 83:13–25 (1991).

Naka et al., "Activation of Hepatocyte Growth Factor by Proteolytic Conversion of a Single Chain Form to a Heterodimer" *The Journal of Biological Chemistry* 267(28):20114–20119 (1992).

Naldini et al., "Scatter Factor and Hepatocyte Growth Factor are Indistinguishable Ligands for the MET Receptor" *EMBO Journal* 10(10):2867–2878 (1991).

Neuhaus et al., "Improved thrombolysis with a modified dose regimen of recombinant tissue–type plasminogen activator" *JACC* 14:1566 1569 (1989).

Neuhaus et al., "Intravenous Recombinant Tissue Plasminogen Activator (rt–PA) and Urokinase in Acute Myocardial Infarction: Results of the German Activator Urokinase Study (GAUS)" *J. Am. Cell Cardiol.* 12:581–587 (1988).

Nielsen et al., "Identification of Prokaryotic and Eukaryotic Signal Peptides and Prediction of Their Cleavage Sites" *Protein Engineering.* 10(1):1–6 (1997).

O'Brien et al., "Expression of cyr61, a Growth Factor–Inducible Immediate–Early Gene" *Mol. Cell Biol.* 10:3569–3577 (1990).

O'Reilly et al., "Angiostatin: a novel angiogenesis inhibitor that mediates the suppression of metastasis by a Lewis lung carcinoma" Cell 79(2):315–328 (1994).

O'Reilly et al., "Endostatin: an endogenous inhibitor of angiogenesis and tumor growth" *Cell* 88(2):277–285 (1997).

O'Rourke and Reibel, "Effects of Adrenoceptor Blockade on Cardiac Hypertrophy and Myocardial Phospholipids" P.S.E.*M.B.* 200:95–100 (1992).

Polladino et al., "Characterization of the Antitumor Activities of Human Tumor Necrosis Factor–α and the Comparison with Other Cytokines: Induction of Tumor–Specific Immunity" *J. Immunol.* 138(11):4023–4032 (1987).

Pennica et al., "Expression cloning of cardiotrophin 1, a cytokine that induces cardiac myocyte hypertrophy" *Proc. Natl. Acad. Sci. USA* 92:1142–1146 (1995).

Piper et al., "Adult Ventricular Rat Heart Muscle Cells" *Cell Culture Techniques in Heart and Vessel Research*, H.M. Piper, Berlin:Springer–Verlag pps. 36–60 (1990).

Pollick, C., "Muscular subaortic stenosis, hemodynamic and clinical improvement after disopyramide" *New England J. of Medicine* 307(16):997 999 (1982).

Quivev et al., "Computerized Tomography in the Quantitative Assessment of Tumour Response" *Br. J. Cancer* 41:suppl. 4, 30 (1980).

REFSEQ Database, Accession No. NM_003710, "Hepatocyte growth factor activator inhibitor precursor" (blast results) (1998).

Reddy et al., "Update on digoxin and other oral positive inotropic agents for chronic heart failure" *Curr. Op. in Cardiol.* 12:233 241 (1997).

Rossi and Peres, "Effect of captopril on the prevention and regression of myocardial cell hypertrophy and interstitial fibrosis in pressure overload cardiac hypertrophy" *Am. Heart J.* 124:700 709 (1992).

Rubin et al., "A Broad–Spectrum Human Lung Fibroblast–Derived Mitogen is a Variant of Hepatocyte Growth Factor" *Proc. Natl. Acad Sci. USA* 88:415–419 (1991).

Ryneck et al., "Structure, mapping, and expression of fisp–12, a growth factor–inducible gene encoding a secreted cysteine–rich protein" *Cell Growth Differ.* 2:225–233 (1991).

The SOLVD Investigators, "Effect of Enalapril on Survival in Patients with Reduced Left Ventricular Ejection Fractions and Congestive Heart Failure" *New England J. of Medicine* 325(5):293–302 (1991).

Schwartz et al., "Molecular Basis of Familial Cardiomyopathies" *Circulation* 91:532–540 (1995).

Shahi et al., "Regression of hypertensive left ventricular hypertrophy and left ventricular diastolic function" *Lancet* 336:458–461 (1990).

Shahzad et al., "The molecular genetics of hypertrophic cardiomyopathy" *Curr. Opin. Cardiol* 12:295–302 (1997).

Shimomura et al., "Activation of hepatocyte growth factor by two homologous proteases, blood–coagulation factor XIIa and hepatocyte growth factor activator" *European Journal of Biochemistry* 229:257–261 (1995).

Shimomura et al., "Hepatocyte Growth Factor Activator Inhibitor, a Novel Kunitz–type Serine Protease Inhibitor" *Journal of Biological Chemistry* 272:6370–6376 (1997).

Simmons et al., "Identification of a phorbol ester–repressible v–src–inducible gene" *Proc. Natl. Acad. Sci*. 86:1178 1182 (1989).

Smith et al., "Rapid Ventricular Filling in Left Ventricular Hypertrophy: II. Pathological Hypertrophy" *J. Am. Cell. Cardiol.* 5:869–874 (1985).

Spirilo et al., "Clinical course and prognosis of hypertrophic cardiomyopathy in an outpatient population" *New England J. of Medicine* 320:749–755 (1989).

Spirito et al., "The Management of Hypertrophic Cardiomyopathy" *New England J of Medicine* 336:775–785 (1997).

Stoker et al., "Scatter Factor is a Fibroblast–Derived Modulator of Epithelial Cell Mobility" *Nature* 327:239–242 (May 21, 1987).

Swissprot (SPROT) Database, SPT1_Human, "Kunitz–type protease inhibitor 1 precursor—*homo sapiens*" (blast results) (Feb. 27, 2001).

Szlachcic et al., "Effect of diltiazcm on left ventricular mass and diastolic filling in mild to moderate hypertension" *Am J Cardiol.* 63:198–201 (1989).

Tebbe et al., "Single–Bolus injection of Recombinant Tissue–Type Plasminogen Activator in Acute Myocardial Infarction" *Am. J. Cardiol.* 64:448–453 (1989).

Thierfelder et al., "α–Tropomyosin and Cardiac Troponin T Mutations Cause Familial Hypertrophic Cardiomyopathy: A Disease of the Sarcomere" *Cell* 77:701–712 (1994).

Thomas and Capecchi, "Site–Directed Mutagenesis by Gene Targeting in Mouse Embryo–Derived Stem Cells." Cell. 51:503–512 (Nov. 1987).

Thompson et al., "Effects of propranolol on myocardial oxygen consumption, substrate extraction, and haemodynamics in hypertrophic obstructive cardiomyopathy" *Br. Heart J.* 44:488–498 (1980).

Tincher et al., "Vascular Endothelial Growth Factor: A New Member of the Platelet–Derived Growth Factor Gene Family." *Biochem. & Biophys. Res. Comm.* 165:1198–1206 (1989).

Togo et al., "Host Organ Specifically Determines Cancer Progression" *Cancer Research* 55:681–684 (Feb. 1, 1995).

Topol et al., "Comparison of Two Dose Regimens of Intravenous Tissue Plasminogen Activator for Acute Myocardial Infarction" *Am. J Cardiol.* 61:723–728 (1988).

Topol, E.J., "Ultrathrombolysis" *J. Am Coll. Cardiol.* 15:922–924 (1990).

Van der Putlon et al., "Efficient Insertion of Genes Into the Mouse Germ Line Via Retroviral Vectors" *Proc. Natl. Acad. Sci. USA* 82:6148–6152 (1985).

Wang et al., "Antibodies to Macrophage Stimulating Protein (MSP): Specificity, Epitope Interactions, and Immunoassay of MSP in Human Serum" *Journal of Leukocyte Biology* 54:289–295 (1994).

Warren et al., "Regulation by vascular endothelial growth factor of human colon cancer tumorigenesis in a mouse model of experimental liver metastasis" *J Clin. Invest.* 95(4):1789–1797 (1995).

Watkins et al., "Characteristics and prognostic implications of myosin missense mutations on familial hypertrophic cardiomyopathy" *New England J. of Medicine* 326:1108–1114 (1992).

Watkins et al., "Mutations in the cardiac myosin binding protein–C gene on chromosome 11 cause familial hypertrophic cardiomyopathy" *Nat. Gen* 11:434–437 (1995).

Weber, K., "Extracellular Matrix Remodeling in Heart Failure: A Role for De Novo Angiotensin II Generation" *Circulation* 96:4065–4082 (1997).

Weidner et al., "Scatter Factor: Molecular Characteristics and Effect on the Invasiveness of Epithelial Cells" *Journal of Cell Biology* 111:2097–2108 (Nov. 1990).

Weidner et al., "Tumor angiogenesis and metastasis—correlation in invasive breast carcinoma" *New England J. of Medicine* 324(1):1 8 (1991).

Wigle et al., "Hypertrophic cardiomyopathy, clinical spectrum and treatment" *Circulation* 92:1680–1692 (1995).

Winter, "Epidermal Regeneration Studied in the Domestic Pig" *Epidermal Wound Healing*, Maibach, H.I. and Rovoe D.T., Chicago:Year Book Medical Publishers, Inc. pps. 71–112 (1972).

Yanagisawa and Masaki, "Molecular Biology and Biochemistry of the Endothelins" *Trends Pharm. Sci.* 10:374 378 (Sep. 1989).

Yanagisawa et al., "A novel potent vasoconstrictor peptide produced by vascular endothelial cells" *Nature* 332:411–415 (1988).

Zacharaski, L.R., "Basis For Selection of Anticoagulant Drugs For Therapeutic Trials in Human Malignancy" *Haemostasis* 16:300 320 (1986).

Zapf et al., "Inhibition of the Action of Nonsuppressible Insulin–like Activity on the Isolated Rat Fat. Cells by Binding to its Carrier Protein" *J. Clin Invest.* 63:1077–1084 (1979).

von Haijne, G., "A new method for predicting signal sequence cleavage sites" *Nucl Acids. Res.* 14(11):4683–4690 (1986).

Shimomura et al., "Hepatocyte Growth Factor Activator Inhibitor, a Novel Kunitz–type Serine Protease Inhibitor" *Journal of Biological Chemistry* 272:6370–6376 (1997).

* cited by examiner

GGGGGAGAAGGCGGCCCGAGCCCCCAGTCTCTCCGAGCACCGGGTCTGGAAGCCGGACCCGAGCCGCGCAGGAA
GCTGGGACCGGAACCTCGGCGACTCGACCCGGCCACCCCCAACCCCCTGGGGAGGAAGGCGCAGGTCACCGACCCTCGGAAC
CCAGAGCCCGGCTCTGAAGGTGACCCCCCTGCGTGTGGGCTTCTGTGCACGCTCGGCCTCCAGGGCA
CGCCCGCCTCGCCCCGGCATCCGCCCCGCCCCCTGGGCTGCCCGGGAGCCGACTGCCGACTGAGCCTGAACAGTTTACCGCC
CCCAGGCGGGCCCTGGCTTCGTGCTGACGACCAACGCCTCGGTGCAGCAGGAGCTACCTTCTGAGTCCCCAC
GGGTGCCGCGGGACTGGGAACTGGGGACTGCCAACGGCCATCGCCGCCCGCCCATCGCCGCGCCATCGCCTCTACGCGCCTCTACGCCA
CGTGCGCGGGACCGCGGGGAGGACGCCATCGCCGCCCATCGCCGCGCCATCGCCTCTACGCGCCTCTACGCCA
TGCAGCCCGACCGCGGGAGGACGCCATCGCCGCGCCATCGCCTCTACGCGCCTCTACGCCA
GTGTGCAAGTTCGCGCCCCAGGGCTTTGGAGGGTCTGAAGCGCCATCCAGTGTCTGCACCTGTCAGCCCGACGCTTC
GCTGCGGACCCCAGGCTTTGCTGAAGATGTGAAAACAGATTGGGGACTGTGGGGACTCACGAGTCCACAAGCTACAAC
CCAGGAACCCCTGGTGCTGAAGATGTGAAAACAGATTGGGGACTGTGGGGACTCACGAGTCCACAAGCTACAAC
AGGGTAGAGAAAGACCAAACCAGTGGAACTGTGGGACTCACAGTGCTGTGTCCACCAAGCAGA
GACAGTGACTAGCTCAGACCCACCCAGAGACGACCAGCTGGGTGTCGCTGCCCAAGTGCACTGCTGTCCACCAAGCAGA
CAGAAGACTACTGCCTCGCATGCAAGATCTGCAAGAGTTTGTTTAGGAGGCTGCTTGGGCAAGAACTGAGGCTGCACCTTCGGGA
CCCACGGAGCAGATCTGCATTCTAGCCTGTGTCGGGTGCAAGTGGGCCTTTGAGAGGCAGCTCTGGCACCTGTCAGCCCCAGTTC
CTTTCCCCAGCAATGCTGCTGGAAGGCGCCATCCAGTGTCTGGACACAGTTCCTGGATGGCCATCCCCGACGCCTC
CGCTGCAGCAATGGCTGCTGTGAAAAATACAGAGTGCCATCGAGAGCTTTGACGAGCTCCAGTGCATCCATTCCCCAGTGACA
CGAGGAGGCACTGCCTGTGGACCTGCCAGAGACCTGCCAGAGAACCTCTGCAAGAGAGCATCCGCGCGTGGTACTACAACCCC
AAGGCCACTGCCTGTGGACCTGCCAGATCTCCAAGAAGATGTGTTGCCTGAAGAGACAACTTTGAGGAAGAGCA
TTCAGTGCCTCGAGTCTCGTGCGCGACATCTCCAAGAAGATGTGTTGCCTGAAGAGACAACTTTGAGGAAGAGCA
GCAGTTGCCTCGAGTCTCGTGTGAGAATGGCTGTGTCAGTGCCATCTCGTCATTGGCGGGAAATCCCATTC
CCAGCACAGGCTCTGGCCCCCAGGTTCTGTGAGAATGGCTGTGTCAGTGTCTGTCATCTGCATTGTGTGGTGACCAC
TTGGGTTACTGCTTCTTCAAGAACCAGAGAAGGACTTCCACGACACCTGTCTATAACCACACACACCGGCCCCTCT
TGCCAGTCGCCACTGTCTCCAGGGTCTCACCGGCCTCTTGCCTGTTTCCAGGCCCACTGCCAAGGCAGAGACCAGGCTTCAGCTCCTCT
GAGCCTGGTGGTCTCACCGGCCTCTTGCCTGTTTCCAGGCCCACTGTGCCTCAGAGACCAGGCTTCAGCTCCTCTCT
AACTTTGGAACCAGACTCTCAGTCAGCTAAGCTCAGTCAGTCCAGAAGTTTGAAGGAGCAGAAAACCCTTGGC
TGGAGAAGTCCAGATAGATGGACCTACCCATGGTGCTAGGAAGAGAGTGGGGTGGTCAGACCCTGGAGGCCCAA
CAAAGTGCCTCGTCGTGCCTACCCATGGTGCTAGGAAGAGAGTGGGGTGGTCAGACCCTGGAGGCCCAA
CCCTGTCCTCCGAGCTCCTTCCGAGCTCTTCCATGCGTCGCCCAGGGCTGGAGGAGGAAGACTTCCCTGTGTAGTTT
GTGCTGTAAAGAGTTGCTTTTGTTTTATTGGTGTGCATGGGTGAAGAGGTGAAAGAGGGAAGGCCTGTT
TGGCCTCTCTGTCCTCTCTCCCTCTTTCCCCCAAGATTGAGCTCTGCCCTTGATCAGCCCCACCCTGCC
TAGACCAGCAGAGAGAGCCAGGAGAGGCTCAGCTGCATTCCGCAGCCCCACCCCAAGTTCTCCAACAT
CACAGCCCAGCCACTGGGTAATAAAAGTGGTTTGTGGAAAAAAAAAAAAAAAAAAA

FIG._1

MAPARTMARARLAPAGIPAVALWLLCTLGLQGTQAGPPPAPPGLPAGADCLNSFTAGVPGFVLDTNASVSN
GATFLESPTVRRGWDCVRACCTTQNCNLALVELQPDRGEDAIAACFLINCLYEQNFVCKFAPREGFINYLT
REVYRSYRQLRTQGFGGSGIPKAWAGIDLKVQPQEPLVLKDVENTDWRLLRGDTDVRVERKDPNQVELWGL
KEGTYLFQLTVTSSDHPEDTANVTVTVLSTKQTEDYCLASNKVGRCRGSFPRWYYDPTEQICKSFVYGGCL
GNKNNYLREEECILACRGVQGGPLRGSSGAQATFPQGPSMERRHPVCSGTCQPTQFRCSNGCCIDSFLECD
DTPNCPDASDEAACEKYTSGFDELQRIHFPSDKGHCVDLPDTGLCKESIPRWYNPFSEHCARFTYGGCYG
NKNNFEEEQQCLESCRGISKKDVFGLRREIPIPSTGSVEMAVTVFLVICIVVVAILGYCFFKNQRKDFHG
HHHHPPPTPASSTVSTTEDTEHLVYNHTTRPL signal sequence:                    Amino acids 1-35 transmembrane domain:               Amino acids 466-483

N-glycosylation sites:              Amino acids 66-70;235-239;523-527

N-myristoylation sites:             Amino acids 29-35;43-49;161-167;
                                    212-218;281-287;282-288;
                                    285-291;310-316;313-319;
                                    422-428;423-429;426-432

Cell attachment sequence:           Amino acids 193-199

Pancreatic trypsin inhibitor (Kunitz) family signatures:
                                    Amino acids 278-298;419-438

FIG._2

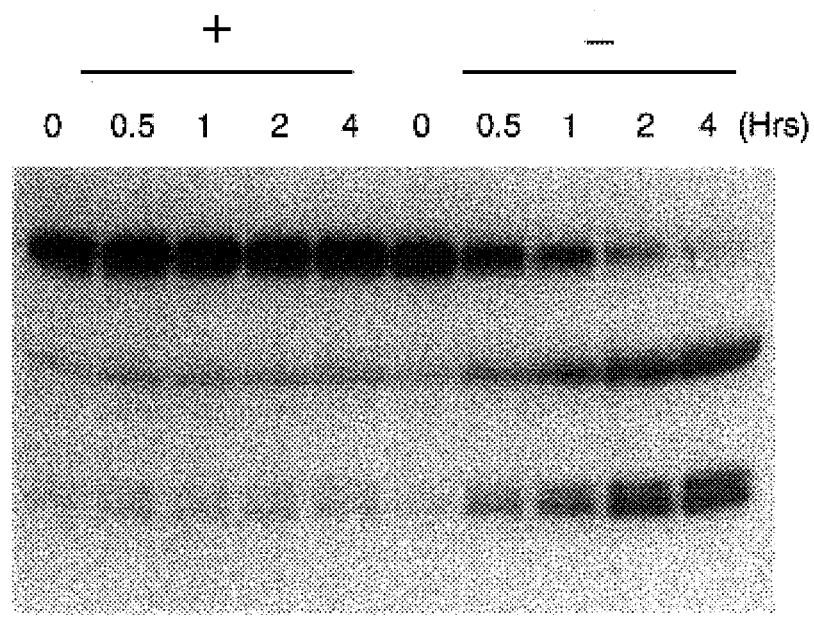
FIG._3A
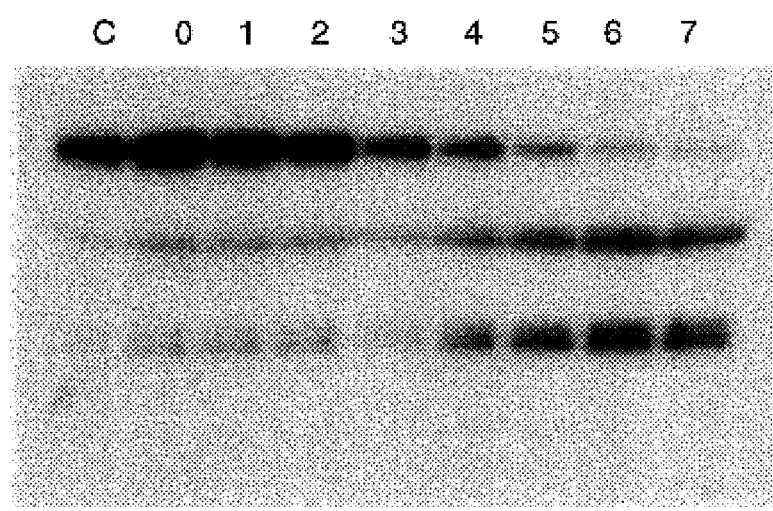
FIG._3B

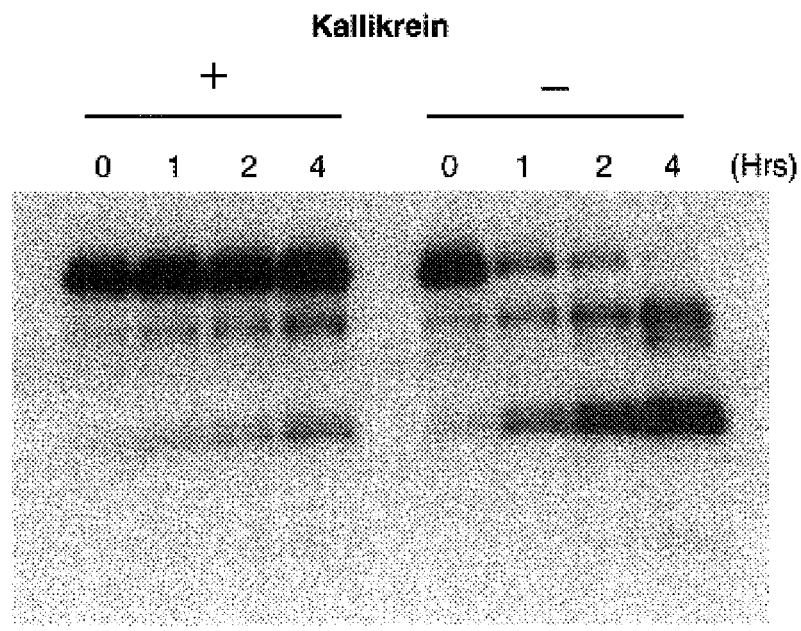
FIG._4A
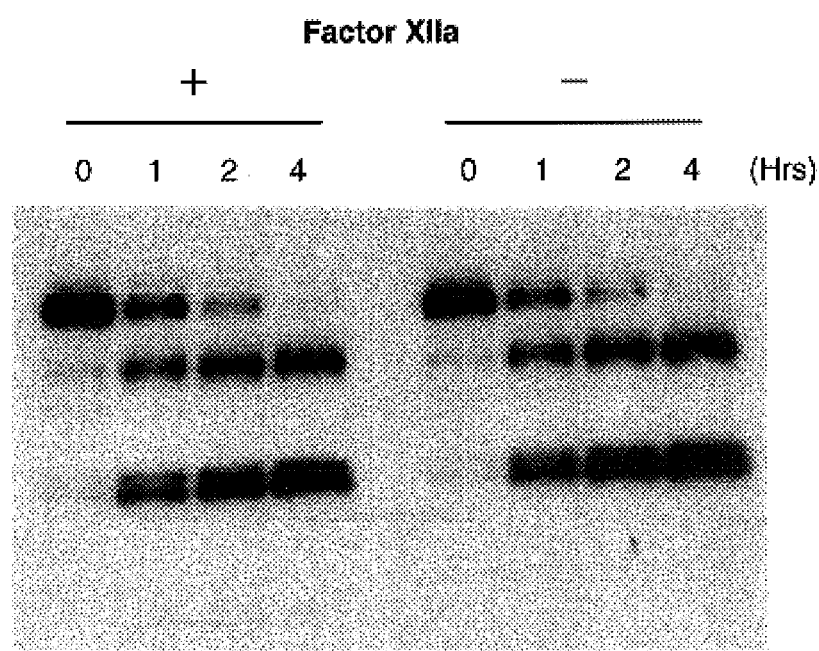
FIG._4B

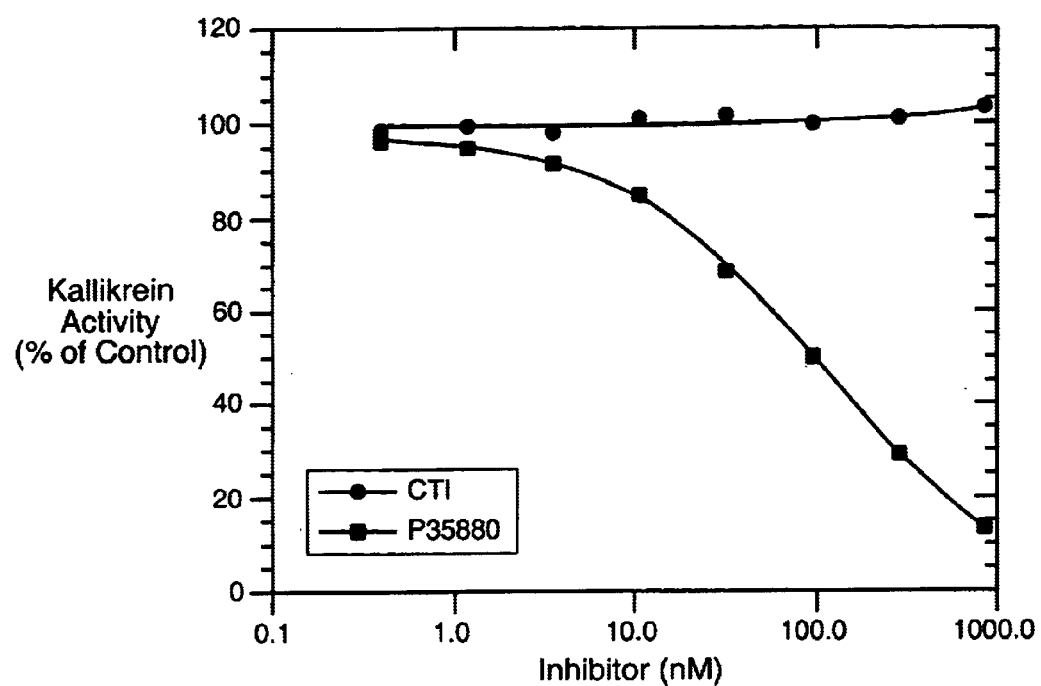
FIG._5

SEQUENCE LISTING

<160> NUMBER OF SEQ ID NOS: 6

<210> SEQ ID NO 1
<211> LENGTH: 2482
<212> TYPE: DNA
<213> ORGANISM: Homo sapiens

<400> SEQUENCE: 1

| | | | | |
| --- | --- | --- | --- | --- |
| gggggagaag | gcggccgagc | cccagctctc | cgagcaccgg | gtcggaagcc | 50 |
| gcgacccgag | ccgcgcagga | agctgggacc | ggaacctcgg | cggacccggc | 100 |
| cccacccaac | tcacctgcgc | aggtcaccag | caccctcgga | acccagaggc | 150 |
| ccgcgctctg | aaggtgaccc | ccctggggag | gaaggcgatg | gccctgcga | 200 |
| ggacgatggc | ccgcgcccgc | ctcgcccgg | ccggcatccc | tgccgtcgcc | 250 |
| ttgtggcttc | tgtgcacgct | cggcctccag | ggcacccagg | ccgggccacc | 300 |
| gcccgcgccc | cctgggctgc | ccgcgggagc | cgactgcctg | aacagcttta | 350 |
| ccgccggggt | gcctggcttc | gtgctggaca | ccaacgcctc | ggtcagcaac | 400 |
| ggagctacct | tcctggagtc | ccccaccgtg | cgccggggct | gggactgcgt | 450 |
| gcgcgcctgc | tgcaccaccc | agaactgcaa | cttggcgcta | gtggagctgc | 500 |

| | |
|---|---|
| agcccgaccg cggggaggac gccatcgccg cctgcttcct catcaactgc | 550 |
| ctctacgagc agaacttcgt gtgcaagttc gcgcccaggg agggcttcat | 600 |
| caactacctc acgagggaag tgtaccgctc ctaccgccag ctgcggaccc | 650 |
| agggctttgg agggtctggg atccccaagg cctgggcagg catagacttg | 700 |
| aagtacaac cccaggaacc cctggtgctg aaggatgtgg aaaacacaga | 750 |
| ttggcgccta ctgcggggtg acacggatgt cagggtagag aggaaagacc | 800 |
| caaaccaggt ggaactgtgg ggactcaagg aaggcaccta cctgttccag | 850 |
| ctgacagtga ctagctcaga ccacccagag gacacggcca acgtcacagt | 900 |
| cactgtgctg tccaccaagc agacagaaga ctactgcctc gcatccaaca | 950 |
| aggtgggtcg ctgccgggc tctttcccac gctggtacta tgaccccacg | 1000 |
| gagcagatct gcaagagttt cgtttatgga ggctgcttgg caacaagaa | 1050 |
| caactacctt cggaagaag agtgcattct agcctgtcgg ggtgtgcaag | 1100 |
| gtgggccttt gagaggcagc tctggggctc aggcgacttt cccccagggc | 1150 |
| ccctccatgg aaaggcgcca tccagtgtgc tctggcacct gtcagcccac | 1200 |
| ccagttccgc tgcagcaatg gctgctgcat cgacagtttc ctggagtgtg | 1250 |
| acgacacccc caactgcccc gacgcctccg acgaggctgc ctgtgaaaaa | 1300 |
| tacacgagtg gctttgacga gctccagcgc atccatttcc ccagtgacaa | 1350 |
| agggcactgg gtggacctgc cagacacagg actctgcaag gagagcatcc | 1400 |
| cgcgctggta ctacaacccc ttcagcgaac actgcgcccg ctttacctat | 1450 |
| ggtggttgtt atggcaacaa gaacaacttt gaggaagagc agcagtgcct | 1500 |
| cgagtcttgt cgcggcatct ccaagaagga tgtgtttggc ctgaggcggg | 1550 |
| aaatccccat tccagcaca ggctctgtgg agatggctgt cacagtgttc | 1600 |
| ctggtcatct gcattgtggt ggtggtagcc atcttgggtt actgcttctt | 1650 |
| caagaaccag agaaaggact tccacggaca ccaccaccac ccaccaccca | 1700 |
| cccctgccag ctccactgtc tccactaccg aggacacgga gcacctggtc | 1750 |
| tataaccaca ccaccccggcc cctctgagcc tgggtctcac cggctctcac | 1800 |
| ctggccctgc ttcctgcttg ccaaggcaga ggcctgggct gggaaaaact | 1850 |
| ttggaaccag actcttgcct gtttcccagg cccactgtgc ctcagagacc | 1900 |
| agggctccag cccctcttgg agaagtctca gctaagctca cgtcctgaga | 1950 |
| aagctcaaag gttggaagg agcagaaaac ccttgggcca gaagtaccag | 2000 |
| actagatgga cctgcctgca taggagtttg gaggaagttg gagttttgtt | 2050 |
| tcctctgttc aaagctgcct gtccctaccc catggtgcta ggaagaggag | 2100 |
| tggggtggtg tcagaccctg gaggccccaa ccctgtcctc ccgagctcct | 2150 |
| cttccatgct gtgcgcccag ggctgggagg aaggacttcc ctgtgtagtt | 2200 |
| tgtgctgtaa agagttgctt tttgtttatt taatgctgtg gcatgggtga | 2250 |
| agaggagggg aagaggcctg tttggcctct ctgtcctctc ttcctcttcc | 2300 |
| cccaagattg agctctctgc ccttgatcag ccccaccctg gcctagacca | 2350 |
| gcagacagag ccaggagagg ctcagctgca ttccgcagcc cccacccca | 2400 |
| aggttctcca acatcacagc ccagcccacc cactgggtaa taaaagtggt | 2450 |
| ttgtggaaaa aaaaaaaaa aaaaaaaaa aa | 2482 |

```
<210> SEQ ID NO 2
<211> LENGTH: 529
<212> TYPE: PRT
<213> ORGANISM: Homo sapiens

<400> SEQUENCE: 2

Met Ala Pro Ala Arg Thr Met Ala Arg Ala Arg Leu Ala Pro Ala
 1               5                  10                  15

Gly Ile Pro Ala Val Ala Leu Trp Leu Leu Cys Thr Leu Gly Leu
                20                  25                  30

Gln Gly Thr Gln Ala Gly Pro Pro Ala Pro Pro Gly Leu Pro
             35                  40                  45

Ala Gly Ala Asp Cys Leu Asn Ser Phe Thr Ala Gly Val Pro Gly
             50                  55                  60

Phe Val Leu Asp Thr Asn Ala Ser Val Ser Asn Gly Ala Thr Phe
             65                  70                  75

Leu Glu Ser Pro Thr Val Arg Arg Gly Trp Asp Cys Val Arg Ala
             80                  85                  90

Cys Cys Thr Thr Gln Asn Cys Asn Leu Ala Leu Val Glu Leu Gln
             95                 100                 105

Pro Asp Arg Gly Glu Asp Ala Ile Ala Ala Cys Phe Leu Ile Asn
            110                 115                 120

Cys Leu Tyr Glu Gln Asn Phe Val Cys Lys Phe Ala Pro Arg Glu
            125                 130                 135

Gly Phe Ile Asn Tyr Leu Thr Arg Glu Val Tyr Arg Ser Tyr Arg
            140                 145                 150

Gln Leu Arg Thr Gln Gly Phe Gly Gly Ser Gly Ile Pro Lys Ala
            155                 160                 165

Trp Ala Gly Ile Asp Leu Lys Val Gln Pro Gln Glu Pro Leu Val
            170                 175                 180

Leu Lys Asp Val Glu Asn Thr Asp Trp Arg Leu Leu Arg Gly Asp
            185                 190                 195

Thr Asp Val Arg Val Glu Arg Lys Asp Pro Asn Gln Val Glu Leu
            200                 205                 210

Trp Gly Leu Lys Glu Gly Thr Tyr Leu Phe Gln Leu Thr Val Thr
            215                 220                 225

Ser Ser Asp His Pro Glu Asp Thr Ala Asn Val Thr Val Thr Val
            230                 235                 240

Leu Ser Thr Lys Gln Thr Glu Asp Tyr Cys Leu Ala Ser Asn Lys
            245                 250                 255

Val Gly Arg Cys Arg Gly Ser Phe Pro Arg Trp Tyr Tyr Asp Pro
            260                 265                 270

Thr Glu Gln Ile Cys Lys Ser Phe Val Tyr Gly Gly Cys Leu Gly
            275                 280                 285

Asn Lys Asn Asn Tyr Leu Arg Glu Glu Glu Cys Ile Leu Ala Cys
            290                 295                 300

Arg Gly Val Gln Gly Pro Leu Arg Gly Ser Ser Gly Ala Gln
            305                 310                 315

Ala Thr Phe Pro Gln Gly Pro Ser Met Glu Arg Arg His Pro Val
            320                 325                 330

Cys Ser Gly Thr Cys Gln Pro Thr Gln Phe Arg Cys Ser Asn Gly
            335                 340                 345

Cys Cys Ile Asp Ser Phe Leu Glu Cys Asp Asp Thr Pro Asn Cys
```

```
                    350                 355                 360
Pro Asp Ala Ser Asp Glu Ala Ala Cys Glu Lys Tyr Thr Ser Gly
                365                 370                 375
Phe Asp Glu Leu Gln Arg Ile His Phe Pro Ser Asp Lys Gly His
                380                 385                 390
Cys Val Asp Leu Pro Asp Thr Gly Leu Cys Lys Glu Ser Ile Pro
                395                 400                 405
Arg Trp Tyr Tyr Asn Pro Phe Ser Glu His Cys Ala Arg Phe Thr
                410                 415                 420
Tyr Gly Gly Cys Tyr Gly Asn Lys Asn Asn Phe Glu Glu Glu Gln
                425                 430                 435
Gln Cys Leu Glu Ser Cys Arg Gly Ile Ser Lys Lys Asp Val Phe
                440                 445                 450
Gly Leu Arg Arg Glu Ile Pro Ile Pro Ser Thr Gly Ser Val Glu
                455                 460                 465
Met Ala Val Thr Val Phe Leu Val Ile Cys Ile Val Val Val Val
                470                 475                 480
Ala Ile Leu Gly Tyr Cys Phe Phe Lys Asn Gln Arg Lys Asp Phe
                485                 490                 495
His Gly His His His His Pro Pro Pro Thr Pro Ala Ser Ser Thr
                500                 505                 510
Val Ser Thr Thr Glu Asp Thr Glu His Leu Val Tyr Asn His Thr
                515                 520                 525
Thr Arg Pro Leu

<210> SEQ ID NO 3
<211> LENGTH: 21
<212> TYPE: DNA
<213> ORGANISM: Artificial sequence
<220> FEATURE:
<223> OTHER INFORMATION: forward PCR primer

<400> SEQUENCE: 3
tgtccaccaa gcagacagaa g                                            21

<210> SEQ ID NO 4
<211> LENGTH: 21
<212> TYPE: DNA
<213> ORGANISM: Artificial sequence
<220> FEATURE:
<223> OTHER INFORMATION: reverse PCR primer

<400> SEQUENCE: 4
actggatggc gcctttccat g                                            21

<210> SEQ ID NO 5
<211> LENGTH: 50
<212> TYPE: DNA
<213> ORGANISM: Artificial sequence
<220> FEATURE:
<223> OTHER INFORMATION: hybridization probe

<400> SEQUENCE: 5
ctgacagtga ctagctcaga ccacccagag gacacggcca acgtcacagt            50

<210> SEQ ID NO 6
<211> LENGTH: 45
<212> TYPE: DNA
<213> ORGANISM: Artificial sequence
<220> FEATURE:
```

-continued

<223> OTHER INFORMATION: hybridization probe

<400> SEQUENCE: 6
gggctctttc ccacgctggt actatgaccc cacggagcag atctg                45

POLYPEPTIDES THAT INHIBIT HUMAN SERUM-INDUCED CLEAVAGE OF HEPATOCYTE GROWTH FACTOR

This is a non-provisional application claiming priority to provisional application Ser. No. 60/253,665, filed Nov. 28, 2000, and International application No's: PCT/US00/03565, filed Feb. 11, 2000, and PCT/US00/06884, filed Mar. 15, 2000, the entire disclosure of which is hereby incorporated by reference.

BACKGROUND OF THE INVENTION

1. Field of the Invention

The present invention relates to compositions and methods useful for promoting or inhibiting angiogenesis and/or cardiovascularization in mammals in need of such biological effect. This includes the diagnosis and treatment of cardiovascular disorders as well as oncological disorders.

2. Description of Background

A. Cardiac Disorders and Factors

Heart failure affects approximately five million Americans, and new cases of heart failure number about 400,000 each year. It is the single most frequent cause of hospitalization for people age 65 and older in the United States. Recent advances in the management of acute cardiac diseases, including acute myocardial infarction, are resulting in an expanding patient population that will eventually develop chronic heart failure. From 1979 to 1995, hospitalizations for congestive heart failure (CHF) rose from 377,000 to 872,000 (a 130 percent increase) and CHF deaths increased 116 percent.

CHF is a syndrome characterized by left ventricular dysfunction, reduced exercise tolerance, impaired quality of life, and markedly shortened life expectancy. The sine qua non of heart failure is an inability of the heart to pump blood at a rate sufficient to meet the metabolic needs of the body's tissues (in other words, there is insufficient cardiac output).

At least four major compensatory mechanisms are activated in the setting of heart failure to boost cardiac output, including peripheral vasoconstriction, increased heart rate, increased cardiac contractility, and increased plasma volume. These effects are mediated primarily by the sympathetic nervous system and the renin-angiotensin system. See, Eichhorn, *American Journal of Medicine*, 104: 163–169 (1998). Increased output from the sympathetic nervous system increases vascular tone, heart rate, and contractility. Angiotensin II elevates blood pressure by 1) directly stimulating vascular smooth muscle contraction, 2) promoting plasma volume expansion by stimulating aldosterone and antidiuretic hormone secretion, 3) stimulating sympathetic-mediated vascular tone, and 4) catalyzing the degradation of bradykinin, which has vasodilatory and natriuretic activity. See, review by Brown and Vaughan, *Circulation*, 97: 1411–1420 (1998). As noted below, angiotensin II may also have directly deleterious effects on the heart by promoting myocyte necrosis (impairing systolic function) and intracardiac fibrosis (impairing diastolic and in some cases systolic function). See, Weber, *Circulation*, 96: 4065–4082 (1997).

A consistent feature of congestive heart failure (CHF) is cardiac hypertrophy, an enlargement of the heart that is activated by both mechanical and hormonal stimuli and enables the heart to adapt to demands for increased cardiac output. Morgan and Baker, *Circulation*, 83: 13–25 (1991). This hypertrophic response is frequently associated with a variety of distinct pathological conditions such as hypertension, aortic stenosis, myocardial infarction, cardiomyopathy, valvular regurgitation, and intracardiac shunt, all of which result in chronic hemodynamic overload.

Hypertrophy is generally defined as an increase in size of an organ or structure independent of natural growth that does not involve tumor formation. Hypertrophy of the heart is due either to an increase in the mass of the individual cells (myocytes), or to an increase in the number of cells making up the tissue (hyperplasia), or both. While the enlargement of an embryonic heart is largely dependent on an increase in myocyte number (which continues until shortly after birth), post-natal cardiac myocytes lose their proliferative capacity. Further growth occurs through hypertrophy of the individual cells.

Adult myocyte hypertrophy is initially beneficial as a short term response to impaired cardiac function by permitting a decrease in the load on individual muscle fibers. With severe, long-standing overload, however, the hypertrophied cells begin to deteriorate and die. Katz, "Heart Failure", in: Katz A. M. ed., *Physiology of the Heart* (New York: Raven Press, 1992) pp. 638–668. Cardiac hypertrophy is a significant risk factor for both mortality and morbidity in the clinical course of heart failure. Katz, *Trends Cardiovasc. Med.* 5: 37–44 (1995). For further details of the causes and pathology of cardiac hypertrophy see, e.g., *Heart Disease. A Textbook of Cardiovascular Medicine*, Braunwald, E. ed. (W. B. Saunders Co., 1988), Chapter 14, "Pathophysiology of Heart Failure."

On a cellular level, the heart is composed of myocytes and surrounding support cells, generically called non-myocytes. While non-myocytes are primarily fibroblast/mesenchymal cells, they also include endothelial and smooth muscle cells. Indeed, although myocytes make up most of the adult myocardial mass, they represent only about 30% of the total cell numbers present in heart. In response to hormonal, physiological, hemodynamic, and pathological stimuli, adult ventricular muscle cells can adapt to increased workloads through the activation of a hypertrophic process. This response is characterized by an increase in myocyte cell size and contractile protein content of individual cardiac muscle cells, without concomitant cell division and activation of embryonic genes, including the gene for atrial natriuretic peptide (ANP). Chien et al., *FASEB J.*, 5: 3037–3046 (1991); Chien et al., *Annu. Rev. Physiol.*, 55: 77–95 (1993). An increment in myocardial mass as a result of an increase in myocyte size that is associated with an accumulation of interstitial collagen within the extracellular matrix and around intramyocardial coronary arteries has been described in left ventricular hypertrophy secondary to pressure overload in humans. Caspari et al., *Cardiovasc. Res.*, 11: 554–558 (1977); Schwarz et al., *Am. J. Cardiol.*, 42: 895–903 (1978); Hess et al., *Circulation*, 63:360–371 (1981); Pearlman et al., *Lab. Invest.*, 46: 158–164 (1982).

It has also been suggested that paracrine factors produced by non-myocyte supporting cells may additionally be involved in the development of cardiac hypertrophy, and various non-myocyte derived hypertrophic factors, such as, leukocyte inhibitory factor (LIF) and endothelin, have been identified. Metcalf, *Growth Factors*, 7: 169–173 (1992); Kurzrock et al., *Endocrine Reviews*, 12: 208–217 (1991); Inoue et al., *Proc. Natl. Acad. Sci. USA*, 86:2863–2867 (1989); Yanagisawa and Masaki, *Trends Pharm. Sci.*, 10: 374–378 (1989); U.S. Patent No. 5,573,762 (issued Nov. 12, 1996). Further exemplary factors that have been identified as potential mediators of cardiac hypertrophy include cardiotrophin-1 (CT-1) (Pennica et al., *Proc. Nat. Acad. Sci.*

USA, 92: 1142–1146 (1995)), catecholamines, adrenocorticosteroids, angiotensin, and prostaglandins.

At present, the treatment of cardiac hypertrophy varies depending on the underlying cardiac disease. Catecholamines, adrenocorticosteroids, angiotensin, prostaglandins, LIF, endothelin (including endothelin-1, -2, and -3 and big endothelin), and CT-1 are among the factors identified as potential mediators of hypertrophy. For example, beta-adrenergic receptor blocking drugs (beta-blockers, e.g., propranolol, timolol, tertalolol, carteolol, nadolol, betaxolol, penbutolol, acetobutolol, atenolol, metoprolol, carvedilol, etc.) and verapamil have been used extensively in the treatment of hypertrophic cardiomyopathy. The beneficial effects of beta-blockers on symptoms (e.g., chest pain) and exercise tolerance are largely due to a decrease in the heart rate with a consequent prolongation of diastole and increased passive ventricular filling. Thompson et al., *Br. Heart J.*, 44: 488–98 (1980); Harrison et al., *Circulation*, 29: 84–98 (1964). Verapamil has been described to improve ventricular filling and probably reducing myocardial ischemia. Bonow et al., *Circulation*, 72: 853–64 (1985).

Nifedipine and diltiazem have also been used occasionally in the treatment of hypertrophic cardiomyopathy. Lorell et al., *Circulation* 65: 499–507 (1982); Betocchi et al., *Am. J. Cardiol.*, 78: 451–457 (1996). However, because of its potent vasodilating properties, nifedipine may be harmful, especially in patients with outflow obstruction. Disopyramide has been used to relieve symptoms by virtue of its negative inotropic properties. Pollick, *N. Engl. J. Med.*, 307: 997–999 (1982). In many patients, however, the initial benefits decrease with time. Wigle et al., *Circulation*, 92: 1680–1692 (1995). Antihypertensive drug therapy has been reported to have beneficial effects on cardiac hypertrophy associated with elevated blood pressure. Examples of drugs used in antihypertensive therapy, alone or in combination, are calcium antagonists, e.g., nitrendipine; adrenergic receptor blocking agents, e.g., those listed above; angiotensin converting enzyme (ACE) inhibitors such as quinapril, captopril, enalapril, ramipril, benazepril, fosinopril, and lisinopril; diuretics, e.g., chlorothiazide, hydrochlorothiazide, hydroflumethazide, methylchlothiazide, benzthiazide, dichlorphenamide, acetazolamide, and indapamide; and calcium channel blockers, e.g., diltiazem, nifedipine, verapamil, and nicardipine.

For example, treatment of hypertension with diltiazem and captopril showed a decrease in left ventricular muscle mass, but the Doppler indices of diastolic function did not normalize. Szlachcic et al., *Am. J. Cardiol.*, 63: 198–201 (1989); Shahi et al., *Lancet* 336: 458–461 (1990). These findings were interpreted to indicate that excessive amounts of interstitial collagen may remain after regression of left ventricular hypertrophy. Rossi et al., *Am. Heart J.* 124: 700–709 (1992). Rossi et al., supra, investigated the effect of captopril on the prevention and regression of myocardial cell hypertrophy and interstitial fibrosis in pressure overload cardiac hypertrophy, in experimental rats.

Agents that increase cardiac contractility directly (inotropic agents) were initially thought to benefit patients with heart failure because they improved cardiac output in the short term. However, all positive inotropic agents except digoxigenin have been found to result in increased long-term mortality, in spite of short-term improvements in cardiac performance. Massie, *Curr. Op. in Cardiology*, 12: 209–217 (1997); Reddy er al., *Curr. Opin. Cardiol.*, 12: 233–241 (1997). Beta-adrenergic receptor blockers have recently been advocated for use in heart failure. Evidence from clinical trials suggests that improvements in cardiac function can be achieved without increased mortality, though documented improvements patient survival have not yet been demonstrated. See also, U.S. Pat. Nos. 5,935,924; 5,624,806: 5,661,122; and 5,610,134 and WO 95/28173 regarding the use of cardiotropin-1 or antagonists thereof, or growth hormone and/or insulin-like growth factor-I in the treatment of CHF. Another treatment modality is heart transplantation, but this is limited by the availability of donor hearts.

Endothelin is a vasoconstricting peptide comprising 21 amino acids, isolated from swine arterial endothelial culture supernatant and structurally determined. Yanagisawa et al., *Nature*, 332: 411–415 (1988). Endothelin was later found to exhibit various actions, and endothelin antibodies as endothelin antagonists have proven effective in the treatment of myocardial infarction, renal failure, and other diseases. Since endothelin is present in live bodies and exhibits vasoconstricting action, it is expected to be an endogenous factor involved in the regulation of the circulatory system, and may be associated with hypertension, cardiovascular diseases such as myocardial infarction, and renal diseases such as acute renal failure. Endothelin antagonists are described, for example, in U.S. Pat. No. 5,773,414; JP Pat. Publ. 3130299/1991, EP 457,195; EP 460,679; and EP 552,489. A new endothelin B receptor for identifying endothelin receptor antagonists is described in U.S. Pat. No. 5,773,223.

Current therapy for heart failure is primarily directed to using angiotensin-converting enzyme (ACE) inhibitors, such as captopril, and diuretics. These drugs improve hemodynamic profile and exercise tolerance and reduce the incidence of morbidity and mortality in patients with CHF. Kramer et al., *Circulation*, 67 (4): 807–816 (1983); Captopril Multicenter Research Group, *J.A.C.C.*, 2(4): 755–763 (1983); The CONSENSUS Trial Study Group, *N. Engl. J. Med.*, 316(23): 1429–1435 (1987); The SOLVD Investigators, *N. Engl. J. Med.*, 325(5): 293–302 (1991). Further, they are useful in treating hypertension, left ventricular dysfunction, atherosclerotic vascular disease, and diabetic nephropathy. Brown and Vaughan, supra. However, despite proven efficacy, response to ACE inhibitors has been limited. For example, while prolonging survival in the setting of heart failure, ACE inhibitors appear to slow the progression towards end-stage heart failure, and substantial numbers of patients on ACE inhibitors have functional class III heart failure.

Moreover, improvement of functional capacity and exercise time is only small and mortality, although reduced, continues to be high. The CONSENSUS Trial Study Group, *N. Engl. J. Med.*, 316 (23): 1429–1453 (1987); The SOLVD Investigators, *N. Engl. J. Med.*, 325 (5): 293–302 (1991); Cohn et al., *N. Engl. J. Med.*, 325(5): 303–310 (1991); The Captopril-Digoxin Multicenter Research Group, *JAMA*, 259 (4): 539–544 (1988). Hence, ACE inhibitors consistently appear unable to relieve symptoms in more than 60% of heart failure patients and reduce mortality of heart failure only by approximately 15–20%. For further adverse effects, see Brown and Vaughan, supra.

An alternative to ACE inhibitors is represented by specific AT1 receptor antagonists. Clinical studies are planned to compare the efficacy of these two modalities in the treatment of cardiovascular and renal disease. However, animal model data suggests that the ACE/Ang II pathway, while clearly involved in cardiac hypertrophy, is not the only, or even the primary pathway active in this role. Mouse genetic "knock-out" models have been made to test individual components of the pathway. In one such model, the primary cardiac receptor for Ang II, AT sub 1A, has been genetically deleted; these mice do not develop hypertrophy when Ang II is given experimentally (confirming the basic success of the model in eliminating hypertrophy secondary to Ang II). However, when the aorta is constricted in these animals (a model of hypertensive cardiac stress), the hearts still become hypertrophic. This suggests that alternative signaling pathways, not depending on this receptor (AT sub 1A), are activated in hypertension. ACE inhibitors would presumably not be able to inhibit these pathways. See, Harada et al., *Circulation,* 97: 1952–1959 (1998). See also, Homcy, *Circulation,* 97: 1890–1892 (1998) regarding the enigma associated with the process and mechanism of cardiac hypertrophy.

About 750,000 patients suffer from acute myocardial infarction (AMI) annually, and approximately one-fourth of all deaths in the United States are due to AMI. In recent years, thrombolytic agents, e.g., streptokinase, urokinase, and in particular tissue plasminogen activator (t-PA) have significantly increased the survival of patients who suffered myocardial infarction. When administered as a continuous intravenous infusion over 1.5 to 4 hours, t-PA produces coronary patency at 90 minutes in 69% to 90% of the treated patients. Topol et al., *Am. J. Cardiol.,* 61: 723–728 (1988); Neuhaus et al., *J. Am. Coll. Cardiol.,* 12: 581–587 (1988); Neuhaus et al., *J. Am. Coll. Cardiol.,* 14: 1566–1569 (1989). The highest patency rates have been reported with high dose or accelerated dosing regimens. Topol, *J. Am. Coll. Cardiol* 15: 922–924 (1990). t-PA may also be administered as a single bolus, although due to its relatively short half-life, it is better suited for infusion therapy. Tebbe et al., *Am. J. Cardiol.,* 64: 448–453 (1989). A t-PA variant, specifically designed to have longer half-life and very high fibrin specificity, TNK t-PA (a T103N, N117Q, KHRR(296–299) AAAA t-PA variant, Keyt et al., *Proc. Natl. Acad. Sci. USA,* 91: 3670–3674 (1994)) is particularly suitable for bolus administration. However, despite all these advances, the long-term prognosis of patient survival depends greatly on the post-infarction monitoring and treatment of the patients, which should include monitoring and treatment of cardiac hypertrophy.

B. Growth Factors

Various naturally occurring polypeptides reportedly induce the proliferation of endothelial cells. Among those polypeptides are the basic and acidic fibroblast growth factors (FGF) (Burgess and Maciag, *Annual Rev. Biochem.,* 58: 575 (1989)), platelet-derived endothelial cell growth factor (PD-ECGF) (Ishikawa et al., *Nature* 338: 557 (1989)), and vascular endothelial growth factor (VEGF). Leung et al., *Science,* 246: 1306 (1989); Ferrara and Henzel, *Biochem. Biophys. Res. Commun.,* 161: 851 (1989); Tischer et al., *Biochem. Biophys. Res. Commun.,* 165: 1198 (1989); EP 471,754B granted Jul. 31, 1996.

Media conditioned by cells transfected with the human VEGF (hVEGF) cDNA promoted the proliferation of capillary endothelial cells, whereas control cells did not. Leung et al., *Science* 246: 1306 (1989). Several additional cDNAs were identified in human cDNA libraries that encode 121-, 189-, and 206-amino acid isoforms of hVEGF (also collectively referred to as hVEGF-related proteins). The 121-amino acid protein differs from hVEGF by virtue of the deletion of the 44 amino acids between residues 116 and 159 in hVEGF. The 189-amino acid protein differs from hVEGF by virtue of the insertion of 24 amino acids at residue 116 in hVEGF, and apparently is identical to human vascular permeability factor (hVPF). The 206-amino acid protein differs from hVEGF by virtue of an insertion of 41 amino acids at residue 116 in hVEGF. Houck et al., *Mol. Endocrin.,* 5: 1806 (1991); Ferrara et al., *J. Cell. Biochem.,* 47: 211 (1991); Ferrara et al., *Endocrine Reviews,* 13: 18 (1992); Keck et al., *Science,* 246: 1309 (1989); Connolly et al., *J. Biol. Chem.* 264: 20017 (1989); EP 370,989 published May 30, 1990.

It is now well established that angiogenesis, which involves the formation of new blood vessels from preexisting endothelium, is implicated in the pathogenesis of a variety of disorders. These include solid tumors and metastasis, atherosclerosis, retrolental fibroplasia, hemangiomas, chronic inflammation, intraocular neovascular syndromes such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Folkman et al., *J. Biol. Chem.,* 267: 10931–10934 (1992); Klagsbrun et al., *Annu. Rev. Physiol.,* 53: 217–239 (1991); and Garner A., "Vascular diseases", In: *Pathobiology of Ocular Disease, A Dynamic Approach,* Garner A., Klintworth G K, eds., 2nd Edition (Marcel Dekker, NY, 1994), pp 1625–1710.

In the case of tumor growth, angiogenesis appears to be crucial for the transition from hyperplasia to neoplasia, and for providing nourishment to the growing solid tumor. Folkman et al., *Nature,* 339: 58 (1989). The neovascularization allows the tumor cells to acquire a growth advantage and proliferative autonomy compared to the normal cells. Accordingly, a correlation has been observed between density of microvessels in tumor sections and patient survival in breast cancer as well as in several other tumors. Weidner et al., *N. Engl. J. Med,* 324: 1–8 (1991); Horak et al., *Lancet,* 340: 1120–1124 (1992); Macchiarini et al., *Lancet,* 340: 145–146 (1992).

The search for positive regulators of angiogenesis has yielded many candidates, including aFGF, bFGF, TGF-α, TGF-β, hepatocyte growth factor (HGF), TNF-α, angiogenin, IL-8, etc. Folkman et al., *J.B.C.,* supra, and Klagsbrun et al., supra. The negative regulators so far identified include thrombospondin (Good et al., *Proc. Natl. Acad. Sci. USA.,* 87: 6624–6628 (1990)), the 16-kilodalton N-terminal fragment of prolactin (Clapp et al., *Endocrinology,* 133: 1292–1299 (1993)), angiostatin (O'Reilly et al., *Cell,* 79: 315–328 (1994)), and endostatin. O'Reilly et al., *Cell,* 88: 277–285 (1997).

Work done over the last several years has established the key role of VEGF, not only in stimulating vascular endothelial cell proliferation, but also in inducing vascular permeability and angiogenesis. Ferrara et al., *Endocr. Rev.,* 18: 4–25 (1997). The finding that the loss of even a single VEGF allele results in embryonic lethality points to an irreplaceable role played by this factor in the development and differentiation of the vascular system. Furthermore, VEGF has been shown to be a key mediator of neovascularization associated with tumors and intraocular disorders. Ferrara et al., *Endocr. Rev.,* supra. The VEGF mRNA is overexpressed by the majority of human tumors examined. Berkman et al., *J. Clin. Invest.,* 91: 153–159 (1993); Brown et al., *Human Pathol.,* 26: 86–91 (1995); Brown et al., *Cancer Res.,* 53: 4727–4735 (1993); Mattern et al., *Brit. J. Cancer,* 73: 931–934 (1996); Dvorak et al., *Am. J. Pathol.,* 146: 1029–1039 (1995).

Also, the concentration levels of VEGF in eye fluids are highly correlated to the presence of active proliferation of blood vessels in patients with diabetic and other ischemia-related retinopathies. Aiello et al., *N. Engl. J. Med.,* 331:

1480–1487 (1994). Furthermore, recent studies have demonstrated the localization of VEGF in choroidal neovascular membranes in patients affected by AMD. Lopez et al., *Invest. Ophthalmol. Vis. Sci.*, 37: 855–868 (1996).

Anti-VEGF neutralizing antibodies suppress the growth of a variety of human tumor cell lines in nude mice (Kim et al., *Nature*, 362: 841–844 (1993); Warren et al., *J. Clin. Invest.*, 95: 1789–1797 (1995); Borgstrom et al., *Cancer Res.*, 56: 4032–4039 (1996); Melnyk et al., *Cancer Res.*, 56: 921–924 (1996)) and also inhibit intraocular angiogenesis in models of ischemic retinal disorders. Adamis et al., *Arch. Ophthalmol.*, 114: 66–71 (1996). Therefore, anti-VEGF monoclonal antibodies or other inhibitors of VEGF action are promising candidates for the treatment of solid tumors and various intraocular neovascular disorders. Such antibodies are described, for example, in EP 817,648 published Jan. 14, 1998 and in WO98/45331 and WO98/45332 both published Oct. 15, 1998.

There exist several other growth factors and mitogens, including transforming oncogenes, that are capable of rapidly inducing a complex set of genes to be expressed by certain cells. Lau and Nathans, *Molecular Aspects of Cellular Regulation*, 6: 257–293 (1991). These genes, which have been named immediate-early- or early-response genes, are transcriptionally activated within minutes after contact with a growth factor or mitogen, independent of de nova protein synthesis. A group of these intermediate-early genes encodes secreted, extracellular proteins that are needed for coordination of complex biological processes such as differentiation and proliferation, regeneration, and wound healing. Ryseck et al., *Cell Growth Differ.*, 2: 225–233 (1991).

Highly-related proteins that belong to this group include cef 10 (Simmons et al., *Proc. Natl. Acad. Sci. USA*, 86: 1178–1182 (1989)), cyr 61, which is rapidly activated by serum- or platelet-derived growth factor (PDGF) (O'Brien et al., *Mol. Cell Biol.*, 10: 3569–3577 (1990), human connective tissue growth factor (CTGF) (Bradham et al., *J. Cell. Biol.*, 114:1285–1294 (1991)), which is secreted by human vascular endothelial cells in high levels after activation with transforming growth factor beta (TGF-β), exhibits PDGF-like biological and immunological activities, and competes with PDGF for a particular cell surface receptor, fisp-12 (Ryseck et al., *Cell Growth Differ.*, 2: 225–233 (1991)), human vascular IBP-like growth factor (VIGF) (WO 96/17931), and nov, normally arrested in adult kidney cells, which was found to be overexpressed in mycloblastosis-associated-virus-type-1-induced nephroblastomas. Joloit et al., *Mol. Cell. Biol.*, 12: 10–21 (1992).

The expression of these immediate-early genes acts as "third messengers" in the cascade of events triggered by growth factors. It is also thought that they are needed to integrate and coordinate complex biological processes, such as differentiation and wound healing in which cell proliferation is a common event.

As additional mitogens, insulin-like growth factor binding proteins (IGFBPs) have been shown, in complex with insulin-like growth factor (IGF), to stimulate increased binding of IGF to fibroblast and smooth muscle cell surface receptors. Clemmons et al., *J. Clin. Invest.*, 77: 1548 (1986). Inhibitory effects of IGFBP on various IGF actions in vitro include stimulation of glucose transport by adipocytes, sulfate incorporation by chondrocytes, and thymidine incorporation in fibroblast. Zapf et al., *J. Clin. Invest.*, 63: 1077 (1979). In addition, inhibitory effects of IGFBPs on growth factor-mediated mitogen activity in normal cells have been shown.

Another important mitogen, hepatocyte growth factor (HGF), has been reported to function as a complete mitogen for hepatocytes in primary culture and to play a physiological role in liver regeneration, both in humans and in rodents (for a review see Michalopoulos, G., *FASEB*, 4:176–187 (1990)). Most recently, hepatocyte growth factor (HGF) has been shown to be a mitogen for a variety of cell types including melanocytes, renal tubular cells, keratinocytes, certain endothelial cells and cells of epithelial origin (Igawa et al., *Biochem. Biophys. Res. Commun.*, 174:831–838 (1991); Kan et al., *Biochem. Biophys. Res. Commun*, 174:331–337 (1991); Matsumoto et al., *Biochem. Biophys. Res. Commun.*, 176:45–51 (1991); Rubin et al., *Proc. Natl. Acad. Sci. U.S.A.*, 88:415–419 (1991)). Hepatocyte growth factor (HGF) can also act as a 'scatter factor', an activity that promotes the dissociation of epithelial and vascular endothelial cells in vitro (Stoker et al., *Nature*, 327:239–242 (1987); Weidner et al., *J. Cell Biol.*, 111:2097–2108 (1990); Naldini et al., *EMBO J.*, 10:2867–2878 (1991)). Moreover, hepatocyte growth factor (HGF) has been described as an epithelial morphogen (Montesano et al., *Cell*, 67:901–908 (19991). Therefore, HGF has been postulated to be important in tumor invasion and in embryonic development. HGF is a mesenchymally derived heparin-binding gylcoprotein that is secreted as an inactive single chain precursor from producing cells, and normally it remains in this form, probably associated with the extracellular matrix in the producing tissues. In response to tissue damage such as hepatic and renal injury, the inactive single chain form is converted to an activated heterodimeric molecule exclusively in the injured tissue by limited proteolysis at a single site. Miyazawa et al., *J. Biol. Chem.*, 269: 8966–8970 (1994). Because HGF is a potent mitogen for a variety of cells such as hepatocytes and renal tubular epithelial cells, the proteolytically activated HGF may be involved in regeneration of the injured tissue. Gohda et al., *J. Clin. Invest.*, 81: 414–419 (1988); Igawa et al., *Biochem. Biophys. Res. Commun.*, 174; 831–838 (1991), and Rubin et al., *Proc. Natl. Acad. Sci. U.S.A.*, 88: 415–419 (1991). The activation potential of HGF activator may be neutralized by the activity of a tissue derived inhibitor known as HAI or inhibitor of HGF activator. Characterization of HAI in injured tissues is needed to understand mechanisms for regulating the activation of HGF. Shimomura et al., *J. Biol. Chem.*, 272:6370–6376 (1997). In addition, agonists of the HGF activator inhibitor (HAI) may play a role in inhibiting angiogenesis and can be useful for creating solid tumors by suppressing human tumor growth. Moreover, antagonists to the HGF activator inhibitor (HAI) may play a role in promoting angiogenesis or tissue repair and therefore may be important for either therapeutic revascularization in peripheral vascular disease, in hepatic or renal injury, or restenosis indications.

C. Need for Further Treatments

In view of the role of vascular endothelial cell growth and angiogenesis in many diseases and disorders, it is desirable to have a means of reducing or inhibiting one or more of the biological effects causing these processes. It is also desirable to have a means of assaying for the presence of pathogenic polypeptides in normal and diseased conditions, and especially cancer. Further, in a specific aspect, as there is no generally applicable therapy for the treatment of cardiac hypertrophy, the identification of factors that can prevent or reduce cardiac myocyte hypertrophy is of primary importance in the development of new therapeutic strategies to inhibit pathophysiological cardiac growth. While there are several treatment modalities for various cardiovascular and oncologic disorders, there is still a need for additional therapeutic approaches.

SUMMARY OF THE INVENTION

A. Embodiments

Accordingly, the present invention concerns compositions and methods for promoting or inhibiting angiogenesis and/or cardiovascularization in mammals. The present invention is based on the identification of a novel polypeptide inhibitor of hepatocyte growth factor activator herein designated PRO256. Accordingly, the protein inhibitor and agonists or antagonists thereof, are believed to be useful drugs for the diagnosis and/or treatment (including prevention) of disorders where such effects are desired, such as the promotion or inhibition of angiogenesis, inhibition or stimulation of vascular endothelial cell growth, stimulation of growth or proliferation of vascular endothelial cells, inhibition of tumor growth, inhibition of angiogenesis-dependent tissue growth, or stimulation of angiogenesis-dependent tissue growth.

In one embodiment, the present invention provides a composition comprising a PRO256 polypeptide in admixture with a pharmaceutically acceptable carrier. In one aspect, the composition comprises a therapeutically effective amount of the polypeptide. In another aspect, the composition comprises a further active ingredient, namely, a cardiovascular, endothelial or an angiostatic agent, preferably an angiogenic or angiostatic agent. Preferably, the composition is sterile. The PRO256 polypeptide may be administered in the form of a liquid pharmaceutical formulation, which may be preserved to achieve extended storage stability. Preserved liquid pharmaceutical formulations might contain multiple doses of PRO256 polypeptide, and might, therefore, be suitable for repeated use.

In a further embodiment, the present invention provides a method for preparing such a composition useful for the treatment of a cardiovascular, endothelial or angiogenic disorder comprising admixing a therapeutically effective amount of a PRO256 polypeptide with a pharmaceutically acceptable carrier. Preferably the cardiovascular, endothelial or angiogenic disorder is a tumor.

In another embodiment, the present invention provides a composition comprising an agonist or antagonist of a PRO256 polypeptide in admixture with a pharmaceutically acceptable carrier. Preferably the agonist or antagonist of a PRO256 polypeptide is an anti-PRO256 antibody. In one aspect, the composition comprises a therapeutically effective amount of the agonist or antagonist. In another aspect, the composition comprises a further active ingredient, namely, a cardiovascular, endothelial or angiogenic agent or an angiostatic agent, preferably an angiogenic or angiostatic agent. Preferably, the composition is sterile. The PRO256 polypeptide agonist or antagonist may be administered in the form of a liquid pharmaceutical formulation, which may be preserved to achieve extended storage stability. Preserved liquid pharmaceutical formulations might contain multiple doses of a PRO256 polypeptide agonist or antagonist, and might, therefore, be suitable for repeated use.

In a further embodiment, the present invention provides a method for preparing such a composition useful for the treatment of a cardiovascular, endothelial or angiogenic disorder comprising admixing a therapeutically effective amount of a PRO256 polypeptide or agonist or antagonist thereof with a pharmaceutically acceptable carrier. Preferably the cardiovascular, endothelial or angiogenic disorder is a tumor.

In yet another embodiment, the present invention concerns a composition comprising an anti-PRO256 antibody in admixture with a pharmaceutically acceptable carrier. In one aspect, the composition comprises a therapeutically effective amount of the antibody. In another aspect, the composition comprises a further active ingredient, namely, a cardiovascular, endothelial or angiogenic agent or an angiostatic agent, preferably an angiogenic or angiostatic agent. Preferably, the composition is sterile. The composition may be administered in the form of a liquid pharmaceutical formulation, which may be preserved to achieve extended storage stability. Preserved liquid pharmaceutical formulations might contain multiple doses of the anti-PRO256 antibody, and might, therefore, be suitable for repeated use. In preferred embodiments, the antibody is a monoclonal antibody, an antibody fragment, a humanized antibody, or a single-chain antibody.

In a further embodiment, the present invention provides a method for preparing such a composition useful for the treatment of a cardiovascular, endothelial or angiogenic disorder comprising admixing a therapeutically effective amount of an anti-PRO256 antibody with a pharmaceutically acceptable carrier. Preferably the cardiovascular, endothelial or angiogenic disorder is a tumor.

In a still further aspect, the present invention provides an article of manufacture comprising:

(a) a composition of matter comprising a PRO256 polypeptide or agonist or antagonist thereof;

(b) a container containing said composition; and (c) a label affixed to said container, or a package insert included in said container referring to the use of said PRO256 polypeptide or agonist or antagonist thereof in the treatment of a cardiovascular, endothelial or angiogenic disorder, wherein the agonist or antagonist may be an antibody which binds to the PRO256 polypeptide. The composition may comprise a therapeutically effective amount of the PRO256 polypeptide or the agonist or antagonist thereof.

In another embodiment, the present invention provides a method for identifying an agonist of a PRO256 polypeptide comprising:

(a) contacting cells and a test compound to be screened under conditions suitable for the induction of a cellular response normally induced by a PRO256 polypeptide; and (b) determining the induction of said cellular response to determine if the test compound is an effective agonist, wherein the induction of said cellular response is indicative of said test compound being an effective agonist.

In another embodiment, the present invention provides a method for identifying an agonist of a PRO256 polypeptide comprising:

(a) contacting cells and a test compound to be screened under conditions suitable for the stimulation of cell proliferation by a PRO256 polypeptide; and (b) measuring the proliferation of said cells to determine if the test compound is an effective agonist, wherein the inhibition of cell proliferation is indicative of said test compound being an effective agonist.

In another embodiment, the invention provides a method for identifying a compound that inhibits the activity of a PRO256 polypeptide comprising contacting a test compound with a PRO256 polypeptide under conditions and for a time sufficient to allow the test compound and polypeptide to interact and determining whether the activity of the PRO256 polypeptide is inhibited. In a specific preferred aspect, either the test compound or the PRO256 polypeptide is immobilized on a solid support. In another preferred aspect, the non-immobilized component carries a detectable label. In a preferred aspect, this method comprises the steps of:

(a) contacting cells and a test compound to be screened in the presence of a PRO256 polypeptide under conditions suitable for the induction of a cellular response normally induced by a PRO256 polypeptide; and (b) determining the induction of said cellular response to determine if the test compound is an effective antagonist.

In another preferred aspect, this process comprises the steps of:

(a) contacting cells and a test compound to be screened in the presence of a PRO256 polypeptide under conditions suitable for the stimulation of cell proliferation by a PRO256 polypeptide; and (b) measuring the proliferation of said cells to determine if the test compound is an effective antagonist, wherein the stimulation of cell proliferation is indicative of said test compound being an effective antagonist.

In another embodiment, the invention provides a method for identifying a compound that inhibits the expression of a PRO256 polypeptide in cells that normally expresses the polypeptide, wherein the method comprises contacting the cells with a test compound and determining whether the expression of the PRO256 polypeptide is inhibited. In a preferred aspect, this method comprises the steps of:

(a) contacting cells and a test compound to be screened under conditions suitable for allowing expression of the PRO256 polypeptide; and (b) determining the inhibition of expression of said polypeptide.

In a still further embodiment, the invention provides a compound that inhibits the expression of a PRO256 polypeptide, such as a compound that is identified by the methods set forth above.

Another aspect of the present invention is directed to an agonist or an antagonist of a PRO256 polypeptide which may optionally be identified by the methods described above.

One type of antagonist of a PRO256 polypeptide that inhibits one or more of the functions or activities of the PRO256 polypeptide is an antibody. Hence, in another aspect, the invention provides an isolated antibody that binds a PRO256 polypeptide. In a preferred aspect, the antibody is a monoclonal antibody, which preferably has non-human complementarity-determining-region (CDR) residues and human framework-region (FR) residues. The antibody may be labeled and may be immobilized on a solid support. In a further aspect, the antibody is an antibody fragment, a single-chain antibody, or a humanized antibody. Preferably, the antibody specifically binds to the polypeptide.

In a still further aspect, the present invention provides a method for diagnosing a disease or susceptibility to a disease which is related to a mutation in a PRO256 polypeptide-encoding nucleic acid sequence comprising determining the presence or absence of said mutation in the PRO256 polypeptide nucleic acid sequence, wherein the presence or absence of said mutation is indicative of the presence of said disease or susceptibility to said disease.

In a still further aspect, the invention provides a method of diagnosing a cardiovascular, endothelial or angiogenic disorder in a mammal which comprises analyzing the level of expression of a gene encoding a PRO256 polypeptide (a) in a test sample of tissue cells obtained from said mammal, and (b) in a control sample of known normal tissue cells of the same cell type, wherein a higher or lower expression level in the test sample as compared to the control sample is indicative of the presence of a cardiovascular, endothelial or angiogenic disorder in said mammal. The expression of a gene encoding a PRO256 polypeptide may optionally be accomplished by measuring the level of mRNA or the polypeptide in the test sample as compared to the control sample. Preferably the cardiovascular, endothelial or angiogenic disorder is a tumor.

In a still further aspect, the present invention provides a method of diagnosing a cardiovascular, endothelial or angiogenic disorder in a mammal which comprises detecting the presence or absence of a PRO256 polypeptide in a test sample of tissue cells obtained from said mammal, wherein the presence or absence of said PRO256 polypeptide in said test sample is indicative of the presence of a cardiovascular, endothelial or angiogenic disorder in said mammal. Preferably the cardiovascular, endothelial or angiogenic disorder is a tumor.

In a still further embodiment, the invention provides a method of diagnosing a cardiovascular, endothelial or angiogenic disorder in a mammal comprising (a) contacting an anti-PRO256 antibody with a test sample of tissue cells obtained from the mammal, and (b) detecting the formation of a complex between the antibody and the PRO256 polypeptide in the test sample, wherein the formation of said complex is indicative of the presence of a cardiovascular, endothelial or angiogenic disorder in the mammal. The detection may be qualitative or quantitative, and may be performed in comparison with monitoring the complex formation in a control sample of known normal tissue cells of the same cell type. A larger or smaller quantity of complexes formed in the test sample indicates the presence of a cardiovascular, endothelial or angiogenic dysfunction in the mammal from which the test tissue cells were obtained. The antibody preferably carries a detectable label. Complex formation can be monitored, for example, by light microscopy, flow cytometry, fluorimetry, or other techniques known in the art. The test sample is usually obtained from an individual suspected to have a cardiovascular, endothelial or angiogenic disorder.

In another embodiment, the invention provides a method for determining the presence of a PRO256 polypeptide in a sample comprising exposing a sample suspected of containing the PRO256 polypeptide to an anti-PRO256 antibody and determining binding of said antibody to a component of said sample. In a specific aspect, the sample comprises a cell suspected of containing the PRO256 polypeptide and the antibody binds to the cell. The antibody is preferably detectably labeled and/or bound to a solid support.

In further aspects, the invention provides a cardiovascular, endothelial or angiogenic disorder diagnostic kit comprising an anti-PRO256 antibody and a carrier in suitable packaging. Preferably, such kit further comprises instructions for using said antibody to detect the presence of the PRO256 polypeptide. Preferably, the carrier is a buffer, for example. Preferably, the cardiovascular, endothelial or angiogenic disorder is a tumor.

In yet another embodiment, the present invention provides a method for treating a cardiovascular, endothelial or angiogenic disorder in a mammal comprising administering to the mammal an effective amount of a PRO256 polypeptide. Preferably, the disorder is a tumor. In a further aspect, the mammal is further exposed to a drug that treats endothelial or angiogenic disorders such chemotherapeutic agents if the cardiovascular, endothelial or angiogenic disorder is a tumor. Preferably, the mammal is human.

In another preferred embodiment, the cardiovascular, endothelial or angiogenic disorder is a tumor and the PRO256 polypeptide is administered in combination with a chemotherapeutic agent, a growth inhibitory agent or a cytotoxic agent.

In a further embodiment, the invention concerns a method for treating a cardiovascular, endothelial or angiogenic disorder in a mammal comprising administering to the mammal an effective amount of an agonist of a PRO256 polypeptide. Preferably, the cardiovascular, endothelial or angiogenic disorder is a tumor. Also preferred is where the mammal is human, and where an effective amount of an angiogenic or angiostatic agent is administered in conjunction with the agonist.

In a further embodiment, the invention concerns a method for treating a cardiovascular, endothelial or angiogenic disorder in a mammal comprising administering to the mammal an effective amount of an antagonist of a PRO256 polypeptide. Preferably, the cardiovascular, endothelial or angiogenic disorder is a peripheral vascular disease, hepatic or renal injury, or restenosis indications. Also preferred is where the mammal is human, and where an effective amount of an angiogenic or angiostatic agent is administered in conjunction with the antagonist.

In a further embodiment, the invention concerns a method for treating a cardiovascular, endothelial or angiogenic disorder in a mammal comprising administering to the mammal an effective amount of an anti-PRO256 antibody. Preferably, the cardiovascular, endothelial or angiogenic disorder is a tumor when administering an agonist anti-PRO256 antibody, or a peripheral vascular disease, hepatic or renal injury, or restenosis indications when administering an antagonist anti-PRO256 antibody. Also preferred is where the mammal is human, and where an effective amount of an angiogenic or angiostatic agent is administered in conjunction with the agonist or antagonist antibody.

In still further embodiments, the invention provides a method for treating a cardiovascular, endothelial or angiogenic disorder in a mammal that suffers therefrom comprising administering to the mammal a nucleic acid molecule that codes for either (a) a PRO256 polypeptide, (b) an agonist of a PRO256 polypeptide or (c) an antagonist of a PRO256 polypeptide, wherein said agonist or antagonist may be an anti-PRO256 antibody. In a preferred embodiment, the mammal is human. In another preferred embodiment, the gene is administered via ex vivo gene therapy. In a further preferred embodiment, the gene is comprised within a vector, more preferably an adenoviral, adeno-associated viral, lentiviral, or retroviral vector.

In yet another aspect, the invention provides a recombinant retroviral particle comprising a retroviral vector consisting essentially of a promoter, nucleic acid encoding (a) a PRO256 polypeptide, (b) an agonist polypeptide of a PRO256 polypeptide, or (c) an antagonist polypeptide of a PRO256 polypeptide, and a signal sequence for cellular secretion of the polypeptide, wherein the retroviral vector is in association with retroviral structural proteins. Preferably, the signal sequence is from a mammal, such as from a native PRO256 polypeptide.

In a still further embodiment, the invention supplies an ex vivo producer cell comprising a nucleic acid construct that expresses retroviral structural proteins and also comprises a retroviral vector consisting essentially of a promoter, nucleic acid encoding (a) a PRO256 polypeptide, (b) an agonist polypeptide of a PRO256 polypeptide or (c) an antagonist polypeptide of a PRO256 polypeptide, and a signal sequence for cellular secretion of the polypeptide, wherein said producer cell packages the retroviral vector in association with the structural proteins to produce recombinant retroviral particles.

In yet another embodiment, the invention provides a method for inhibiting endothelial cell growth in a mammal comprising administering to the mammal (a) a PRO256 polypeptide, or (b) an agonist of a PRO256 polypeptide, wherein endothelial cell growth in said mammal is inhibited, and wherein said agonist may be an anti-PRO256 antibody. Preferably, the mammal is human and the endothelial cell growth is associated with a tumor or a retinal disorder.

In yet another embodiment, the invention provides a method for stimulating endothelial cell growth in a mammal comprising administering to the mammal an antagonist of a PRO256 polypeptide, wherein endothelial cell growth in said mammal is stimulated, and wherein said antagonist may be an anti-PRO256 antibody. Preferably, the mammal is human.

In yet another embodiment, the invention provides a method for inhibiting angiogenesis in a mammal comprising administering to the mammal a therapeutically effective amount of (a) a PRO256 polypeptide, or (b) an agonist of a PRO256 polypeptide, wherein angiogenesis in said mammal is inhibited. Preferably, the mammal is a human, and more preferably the mammal has a tumor or a retinal disorder.

In yet another embodiment, the invention provides a method for stimulating angiogenesis in a mammal comprising administering to the mammal a therapeutically effective amount of an antagonist to a PRO256 polypeptide, wherein angiogenesis in said mammal is stimulated. Preferably, the mammal is a human, and more preferably angiogenesis would promote tissue regeneration, wound healing, or would be useful in therapeutic revascularization in peripheral vascular disease, in hepatic or renal injury, or restenosis indications.

In yet another embodiment, the invention provides a method for inhibiting the protease activity of hepatocyte growth factor activator in a mammal comprising administering to the mammal (a) a PRO256 polypeptide, or (b) an agonist of a PRO256 polypeptide, wherein said protease activity is inhibited, and wherein said agonist may be an anti-PRO256 antibody. Preferably, the mammal is human and more preferably the mammal has a tumor or a retinal disorder.

In yet another embodiment, the invention provides a method for stimulating the protease activity of hepatocyte growth factor activator in a mammal comprising administering to the mammal an antagonist of a PRO256 polypeptide, wherein said protease activity is stimulated, and wherein said antagonist may be an anti-PRO256 antibody. Preferably, the mammal is human and more preferably the mammal has a peripheral vascular disease, hepatic or renal injury or restenosis indications.

B. Additional Embodiments

In other embodiments of the present invention, the invention provides an isolated nucleic acid molecule comprising a nucleotide sequence that encodes a PRO256 polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO256 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about97% nucleic acid sequence identity, alternatively at least about 98% nucleic acid sequence identity and alternatively at least about 99% nucleic acid sequence identity to (a) a DNA molecule comprising the coding sequence of a full-length PRO256 polypeptide cDNA as disclosed herein, the coding sequence of a PRO256 polypeptide lacking the signal peptide as disclosed herein, the coding sequence of an extracellular domain of a transmembrane PRO256 polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by the human protein cDNA deposited with the ATCC as disclosed herein, or (b) the complement of the DNA molecule of (a).

Another aspect of the present invention provides an isolated nucleic acid molecule comprising a nucleotide sequence encoding a PRO256 polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO256 polypeptide is contemplated.

Another embodiment is directed to fragments of a PRO256 polypeptide coding sequence, or the complement thereof, that may find use as, for example, hybridization probes, for encoding fragments of a PRO256 polypeptide that may optionally encode a polypeptide comprising a binding site for an anti-PRO256 antibody or as antisense oligonucleotide probes. Such nucleic acid fragments are usually at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a PRO256 polypeptide-encoding nucleotide sequence may be determined in a routine manner by aligning the PRO256 polypeptide-encoding nucleotide sequence with other known nucleotide sequences using any of a number of well known sequence alignment programs and determining which PRO256 polypeptide-encoding nucleotide sequence fragment(s) are novel. All of such PRO256 polypeptide-encoding nucleotide sequences are contemplated herein. Also contemplated are the PRO256 polypeptide fragments encoded by these nucleotide molecule fragments, preferably those PRO256 polypeptide fragments that comprise a binding site for an anti-PRO256 antibody.

In another embodiment, the invention provides an isolated PRO256 polypeptide encoded by any of the isolated nucleic acid sequences hereinabove identified.

In a certain aspect, the invention concerns an isolated PRO256 polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO256 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO256 polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alterna- tively at least about 98% amino acid sequence identity and alternatively at least about 99% amino acid sequence identity to an amino acid sequence encoded by the human protein cDNA deposited with the ATCC as disclosed herein.

In a specific aspect, the invention provides an isolated PRO256 polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO256 polypeptide and recovering the PRO256 polypeptide from the cell culture.

Another aspect of the invention provides an isolated PRO256 polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO256 polypeptide and recovering the PRO256 polypeptide from the cell culture.

In yet another embodiment, the invention concerns agonists and antagonists of a native PRO256 polypeptide as defined herein. In a particular embodiment, the agonist or antagonist is an anti-PRO256 antibody or a small molecule.

In a further embodiment, the invention concerns a method of identifying agonists or antagonists to a PRO256 polypeptide which comprise contacting the PRO256 polypeptide with a candidate molecule and monitoring a biological activity mediated by said PRO256 polypeptide. Preferably, the PRO256 polypeptide is a native PRO256 polypeptide.

In a still further embodiment, the invention concerns a composition of matter comprising a PRO256 polypeptide, or an agonist or antagonist of a PRO256 polypeptide as herein described, or an anti-PRO256 antibody, in combination with a carrier. Optionally, the carrier is a pharmaceutically acceptable carrier.

Another embodiment of the present invention is directed to the use of a PRO256 polypeptide, or an agonist or antagonist thereof as hereinbefore described, or an anti-PRO256 antibody, for the preparation of a medicament useful in the treatment of a condition which is responsive to the PRO256 polypeptide, an agonist or antagonist thereof or an anti-PRO256 antibody.

In additional embodiments of the present invention, the invention provides vectors comprising DNA encoding any of the herein described polypeptides. Host cells comprising any such vector are also provided. By way of example, the host cells may be CHO cells, *E. coli*, yeast, or Baculovirus-infected insect cells. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In yet another embodiment, the invention provides an antibody which specifically binds to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences or as antisense probes, wherein those probes may be derived from any of the above or below described nucleotide sequences.

BRIEF DESCRIPTION OF THE DRAWINGS

FIG. 1 shows a nucleotide sequence (SEQ ID NO:1) of a native sequence PRO256 cDNA, wherein SEQ ID NO:1 is a clone designated herein as "DNA35880-1160".

FIG. 2 shows the amino acid sequence (SEQ ID NO:2) derived from the coding sequence of SEQ ID NO:1shown in FIG. 1.

FIGS. 3(a) to 3(b) show human serum-mediated conversion of $^{125}$I-single-chain hepatocyte growth factor (scHGF) into its two chain form and time course of inhibition by PRO256.FIG. 3(a) shows the time course of inhibition. $^{125}$I-scHGF was incubated with human serum (10%) at 37° C. and aliquots taken at different time points were analyzed by SDS-PAGE under reducing conditions. The bands from the top to the bottom of the gel are scHGF, HGF heavy chain (α-chain) and the HGF light chains (doublet; β-chain). Left lanes (+) are with PRO256 (1 μM) and right lanes (–) are without PRO256.FIG. 3(b) shows the PRO256concentration-dependent inhibition of serum mediated $^{125}$I-scHGF activation after 4 hr incubation.; lane C corresponds to uninhibited $^{125}$I-scHGF conversion; lane 0is time point 0min; lanes 1–7show aliquots taken after 4 hr incubation in the presence of decreasing concentrations of PRO256 (1.27 μM, 0.42 μM, 0.14 μM, 0.047 μM, 0.016 μM, 0.005 μM, and 0.0017 μM).

FIGS. 4(a) to 4(b) show the proteolytic cleavage of $^{125}$I-scHGF by human kallikrein and human factor XIIa. FIG. 4(a) shows the cleavage of $^{125}$I-scHGF (50 μg/ml) by human kallikrein (40 nM) and inhibition by inhibitor PRO256 (1 μM). Kallikrein was pre-incubated for 15 min at 37° C. with inhibitor PRO256 before $^{125}$I-scHGF was added. The reactions were carried out at 37° C. where (+) indicates the presence of inhibitor PRO256and (–) absence of inhibitor PRO256 (=control). FIG. 4(b) shows the conversion of $^{125}$I-scHGF by human factor XIIa (40nM) and lack of inhibition by inhibitor PRO256.

FIG. 5 shows the inhibition of human kallikrein enzymatic activity toward small synthetic substrate (S2305) by inhibitor PRO256. Kallikrein (final concentration of 1.25 nM) and inhibitor PRO256or the specific factor inhibitor corn trypsin inhibitor (CTI) were incubated for 20 min at room temperature. S2305 (final concentration of 1.8 mM) was added and the change in absorbance measured at 405 nM. Inhibition of enzymatic activity was expressed in percent of control rates (mOD$_{405}$/min) of two experiments. The determined IC$_{50}$ for inhibitor PRO256 was 104 nM and the calculated K$_1$* was 37 nM.

DETAILED DESCRIPTION OF THE INVENTION

I. Definitions

The phrases "cardiovascular, endothelial and angiogenic disorder", "cardiovascular, endothelial and angiogenic dysfunction", "cardiovascular, endothelial or angiogenic disorder" and "cardiovascular, endothelial or angiogenic dysfunction" are used interchangeably and refer in part to systemic disorders that affect vessels, such as diabetes mellitus, as well as diseases of the vessels themselves, such as of the arteries, capillaries, veins, and/or lymphatics. This would include indications that stimulate angiogenesis and/or cardiovascularization, and those that inhibit angiogenesis and/or cardiovascularization. Preferably the cardiovascular, endothelial or angiogenic disorder is a tumor. Cardiovascular, endothelial or angiogenic disorders would include, for example, arterial disease, such as atherosclerosis, hypertension, inflammatory vasculitides, Reynaud's disease and Reynaud's phenomenon, aneurysms, and arterial restenosis; venous and lymphatic disorders such as thrombophlebitis, lymphangitis, and lymphedema; and other vascular disorders such as peripheral vascular disease, a type of tumor such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma, tumor angiogenesis, trauma such as wounds, burns, and other injured tissue, implant fixation, scarring, ischemia reperfusion injury, rheumatoid arthritis, cerebrovascular disease, renal diseases such as acute renal failure, and osteoporosis. This would also include angina, myocardial infarctions such as acute myocardial infarctions, cardiac hypertrophy, and heart failure such as CHF.

"Hypertrophy", as used herein, is defined as an increase in mass of an organ or structure independent of natural growth that does not involve tumor formation. Hypertrophy of an organ or tissue is due either to an increase in the mass of the individual cells (true hypertrophy), or to an increase in the number of cells making up the tissue (hyperplasia), or both. Certain organs, such as the heart, lose the ability to divide shortly after birth. Accordingly, "cardiac hypertrophy" is defined as an increase in mass of the heart, which, in adults, is characterized by an increase in myocyte cell size and contractile protein content without concomitant cell division. The character of the stress responsible for inciting the hypertrophy, (e.g., increased preload, increased afterload, loss of myocytes, as in myocardial infarction, or primary depression of contractility), appears to play a critical role in determining the nature of the response. The early stage of cardiac hypertrophy is usually characterized morphologically by increases in the size of myofibrils and mitochondria, as well as by enlargement of mitochondria and nuclei. At this stage, while muscle cells are larger than normal, cellular organization is largely preserved. At a more advanced stage of cardiac hypertrophy, there are preferential increases in the size or number of specific organelles, such as mitochondria, and new contractile elements are added in localized areas of the cells, in an irregular manner. Cells subjected to long-standing hypertrophy show more obvious disruptions in cellular organization, including markedly enlarged nuclei with highly lobulated membranes, which displace adjacent myofibrils and cause breakdown of normal Z-band registration. The phrase "cardiac hypertrophy" is used to include all stages of the progression of this condition, characterized by various degrees of structural damage of the heart muscle, regardless of the underlying cardiac disorder. Hence, the term also includes physiological conditions instrumental in the development of cardiac hypertrophy, such as elevated blood pressure, aortic stenosis, or myocardial infarction.

"Heart failure" refers to an abnormality of cardiac function where the heart does not pump blood at the rate needed for the requirements of metabolizing tissues. The heart failure can be caused by a number of factors, including ischemic, congenital, rheumatic, or idiopathic forms.

"Congestive heart failure" (CHF) is a progressive pathologic state where the heart is increasingly unable to supply adequate cardiac output (the volume of blood pumped by the heart over time) to deliver the oxygenated blood to peripheral tissues. As CHF progresses, structural and hemodynamic damages occur. While these damages have a variety of manifestations, one characteristic symptom is ventricular hypertrophy. CHF is a common end result of a number of various cardiac disorders.

"Myocardial infarction" generally results from atherosclerosis of the coronary arteries, often with superimposed coronary thrombosis. It may be divided into two major types: transmural infarcts, in which myocardial necrosis involves the full thickness of the ventricular wall, and subendocardial (nontransmural) infarcts, in which the necrosis involves the subendocardium, the intramural myocardium, or both, without extending all the way through the ventricular wall to the epicardium. Myocardial infarction is known to cause both a change in hemodynamic effects and an alteration in structure in the damaged and healthy zones of the heart. Thus, for example, myocardial infarction reduces the maximum cardiac output and the stroke volume of the heart. Also associated with myocardial infarction is a stimulation of the DNA synthesis occurring in the interstice as well as an increase in the formation of collagen in the areas of the heart not affected.

As a result of the increased stress or strain placed on the heart in prolonged hypertension due, for example, to the increased total peripheral resistance, cardiac hypertrophy has long been associated with "hypertension". A characteristic of the ventricle that becomes hypertrophic as a result of chronic pressure overload is an impaired diastolic performance. Fouad et al., *J. Am. Coll. Cardiol.,* 3: 1500–1506 (1984); Smith et al., *J. Am. Coll. Cardiol.,* 5: 869–874 (1985). A prolonged left ventricular relaxation has been detected in early essential hypertension, in spite of normal or supranormal systolic function. Hartford et al., *Hypertension,* 6: 329–338 (1984). However, there is no close parallelism between blood pressure levels and cardiac hypertrophy. Although improvement in left ventricular function in response to antihypertensive therapy has been reported in humans, patients variously treated with a diuretic (hydrochlorothiazide), a β-blocker (propranolol), or a calcium channel blocker (diltiazem), have shown reversal of left ventricular hypertrophy, without improvement in diastolic function. Inouye et al., *Am. J. Cardiol.,* 53: 1583–7 (1984).

Another complex cardiac disease associated with cardiac hypertrophy is "hypertrophic cardiomyopathy". This condition is characterized by a great diversity of morphologic, functional, and clinical features (Maron et al., *N. Engl. J. Med.,* 316: 780–789 (1987); Spirito et al., *N. Engl. J. Med.,* 320: 749–755 (1989); Louie and Edwards, *Prog. Cardiovasc. Dis.,* 36: 275–308 (1994); Wigle et al., *Circulation,* 92: 1680–1692 (1995)), the heterogeneity of which is accentuated by the fact that it afflicts patients of all ages. Spirito et al., *N. Engl. J. Med.,* 336 775–785 (1997). The causative factors of hypertrophic cardiomyopathy are also diverse and little understood. In general, mutations in genes encoding sarcomeric proteins are associated with hypertrophic cardiomyopathy. Recent data suggest that β-myosin heavy chain mutations may account for approximately 30 to 40 percent of cases of familial hypertrophic cardiomyopathy. Watkins et al., *N. Engl. J. Med.,* 326: 1108–1114 (1992); Schwartz et al., *Circulation,* 91: 532–540 (1995); Marian and Roberts, *Circulation,* 92: 1336–1347 (1995); Thierfelder et al., *Cell,* 77: 701–712 (1994); Watkins et al., *Nat. Gen.,* 11:434–437 (1995). Besides β-myosin heavy chain, other locations of genetic mutations include cardiac troponin T, alpha topomyosin, cardiac myosin binding protein C, essential myosin light chain, and regulatory myosin light chain. See, Shazad et al., *Curr. Opin. Cardiol.,* 12: 295–302 (1997).

Supravalvular "aortic stenosis" is an inherited vascular disorder characterized by narrowing of the ascending aorta, but other arteries, including the pulmonary arteries, may also be affected. Untreated aortic stenosis may lead to increased intracardiac pressure resulting in myocardial hypertrophy and eventually heart failure and death. The pathogenesis of this disorder is not fully understood, but hypertrophy and possibly hyperplasia of medial smooth muscle are prominent features of this disorder. It has been reported that molecular variants of the elastin gene are involved in the development and pathogenesis of aortic stenosis. U.S. Pat. No. 5,650,282 issued Jul. 22, 1997.

"Valvular regurgitation" occurs as a result of heart diseases resulting in disorders of the cardiac valves. Various diseases, like rheumatic fever, can cause the shrinking or pulling apart of the valve orifice, while other diseases may result in endocarditis, an inflammation of the endocardium or lining membrane of the atrioventricular orifices and operation of the heart. Defects such as the narrowing of the valve stenosis or the defective closing of the valve result in an accumulation of blood in the heart cavity or regurgitation of blood past the valve. If uncorrected, prolonged valvular stenosis or insufficiency may result in cardiac hypertrophy and associated damage to the heart muscle, which may eventually necessitate valve replacement.

The treatment of all these, and other cardiovascular, endothelial and angiogenic disorders, which may or may not be accompanied by cardiac hypertrophy, is encompassed by the present invention.

The term "tumor" refers to an abnormal mass of tissue that is not inflammatory, and arises from cells of preexistent tissue. Tumors may be benign (but serving no physiological purpose), pre-cancerous or cancerous.

The terms "cancer", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. The preferred cancers for treatment herein are breast, colon, lung, melanoma, ovarian, and others involving vascular tumors as noted above.

The term "cytotoxic agent" as used herein refers to a substance that inhibits or prevents the function of cells and/or causes destruction of cells. The term is intended to include radioactive isotopes (e.g., $^{131}$I, $^{125}$I, $^{90}$Y, and $^{186}$Re), chemotherapeutic agents, and toxins such as enzymatically active toxins of bacterial, fungal, plant, or animal origin, or fragments thereof.

A "chemotherapeutic agent" is a chemical compound useful in the treatment of cancer. Examples of chemotherapeutic agents include alkylating agents, folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids. Specific examples include Adriamycin, Doxorubicin, 5-Fluorouracil, Cytosine arabinoside ("Ara-C"), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan, and other related nitrogen mustards. Also included in this definition are hormonal agents that act to regulate or inhibit hormone action on tumors, such as tamoxifen and onapristone.

A "growth-inhibitory agent" when used herein refers to a compound or composition that inhibits growth of a cell, such as an Wnt-overexpressing cancer cell, either in vitro or in vivo. Thus, the growth-inhibitory agent is one which significantly reduces the percentage of malignant cells in S phase. Examples of growth-inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. Additional examples include tumor necrosis factor (TNF), an antibody capable of inhibiting or neutralizing the angiogenic activity of acidic or basic FGF or hepatocyte growth factor (HGF), an antibody capable of inhibiting or neutralizing the coagulant activities of tissue factor, protein C, or protein S (see, WO 91/01753, published Feb. 21, 1991), or an antibody capable of binding to HER2receptor (WO 89/06692), such as the 4D5 antibody (and functional equivalents thereof) (e.g., WO 92/22653).

"Treatment" is an intervention performed with the intention of preventing the development or altering the pathology of a cardiovascular, endothelial, and angiogenic disorder. The concept of treatment is used in the broadest sense, and specifically includes the prevention (prophylaxis), moderation, reduction, and curing of cardiovascular, endothelial, and angiogenic disorders of any stage. Accordingly, "treatment" refers to both therapeutic treatment and prophylactic or preventative measures, wherein the object is to prevent or slow down (lessen) a cardiovascular, endothelial, and angiogenic disorder such as hypertrophy. Those in need of treatment include those already with the disorder as well as those prone to have the disorder or those in whom the disorder is to be prevented. The disorder may result from any cause, including idiopathic, cardiotrophic, or myotrophic causes, or ischemia or ischemic insults, such as myocardial infarction.

"Chronic" administration refers to administration of the agent(s) in a continuous mode as opposed to an acute mode, so as to maintain the initial effect, such as an anti-hypertrophic effect, for an extended period of time.

"Mammal" for purposes of treatment refers to any animal classified as a mammal, including humans, domestic and farm animals, and zoo, sports, or pet animals, such as dogs, horses, cats, cows, sheep, pigs, etc. Preferably, the mammal is human.

Administration "in combination with" one or more further therapeutic agents includes simultaneous (concurrent) and consecutive administration in any order.

The phrase "cardiovascular, endothelial or angiogenic agents" refers generically to any drug that acts in treating cardiovascular, endothelial, and angiogenic disorders. Examples of cardiovascular agents are those that promote vascular homeostasis by modulating blood pressure, heart rate, heart contractility, and endothelial and smooth muscle biology, all of which factors have a role in cardiovascular disease. Specific examples of these include angiotensin-II receptor antagonists; endothelin receptor antagonists such as, for example, BOSENTAN™ and MOXONODIN™; interferon-gamma (IFN-γ); des-aspartate-angiotensin I; thrombolytic agents, e.g., streptokinase, urokinase, t-PA, and a t-PA variant specifically designed to have longer half-life and very high fibrin specificity, TNK t-PA (a T103N, N117Q, KHRR(296–299) AAAA t-PA variant, Keyt et al., *Proc. Natl. Acad. Sci. USA,* 91: 3670–3674 (1994)); inotropic or hypertensive agents such as digoxigenin and β-adrenergic receptor blocking agents, e.g., propranolol, timolol, tertalolol, carteolol, nadolol, betaxolol, penbutolol, acetobutolol, atenolol, metoprolol, and carvedilol; angiotensin converting enzyme (ACE) inhibitors, e.g., quinapril, captopril, enalapril, ramipril, benazepril, fosinopril, and lisinopril; diuretics, e.g., chlorothiazide, hydrochlorothiazide, hydroflumethazide, methylchlothiazide, benzthiazide, dichlorphenamide, acetazolamide, and indapamide; and calcium channel blockers, e.g., diltiazem, nifedipine, verapamil, nicardipine. One preferred category of this type is a therapeutic agent used for the treatment of cardiac hypertrophy or of a physiological condition instrumental in the development of cardiac hypertrophy, such as elevated blood pressure, aortic stenosis, or myocardial infarction.

"Angiogenic agents" and "endothelial agents" are active agents that promote angiogenesis and/or endothelial cell growth, or, if applicable, vasculogenesis. This would include factors that accelerate wound healing, such as growth hormone, insulin-like growth factor-I (IGF-I), VEGF, VIGF, PDGF, hepatocyte growth factor (HGF), epidermal growth factor (EGF), CTGF and members of its family, FGF, and TGF-α and TGP-β.

"Hepatocyte growth factor (HGF)" is a potent mitogen, motogen and morphogen for parenchymal liver, epithelial and endothelial cells.

"Mature hepatocyte growth factor (HGF)" is a heterodimeric protein consisting of a heavy chain (α-chain) and a light chain (β-chain) held together by a disulfide bond. The two chains are produced from a single-chain precursor (scHGF) by proteolytic processing. This processing, which is mediated by a serine protease, is required for HGF to exert both its mitogenic and morphogenic effects.

"Hepatocyte growth factor (HGF) activator" refers to a serine protease that is produced and secreted in the liver and circulates in the blood as an inactive zymogen. In response to tissue injury, the HGF activator zymogen is converted to the active form by limited proteolysis. The activated HGF activator converts an inactive single chain precursor of HGF (scHGF) to a biologically active heterodimer in injured tissue.

"Angiostatic agents" are active agents that inhibit angiogenesis or vasculogenesis or otherwise inhibit or prevent growth of cancer cells. Examples include antibodies or other antagonists to angiogenic agents as defined above, such as antibodies to VEGF. They additionally include cytotherapeutic agents such as cytotoxic agents, chemotherapeutic agents, growth-inhibitory agents, apoptotic agents, and other agents to treat cancer, such as anti-HER-2, anti-CD20, and other bioactive and organic chemical agents.

In a pharmacological sense, in the context of the present invention, a "therapeutically effective amount" of an active agent such as a PRO256 polypeptide or agonist or antagonist thereto or an anti-PRO256 antibody, refers to an amount effective in the treatment of a cardiovascular, endothelial or angiogenic disorder in a mammal and can be determined empirically.

As used herein, an "effective amount" of an active agent such as a PRO256polypeptide or agonist or antagonist thereto or an anti-PRO256 antibody, refers to an amount effective for carrying out a stated purpose, wherein such amounts may be determined empirically for the desired effect.

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO256polypeptides described herein may be isolated from a variety of sources, such as from human tissue types or from another source, or prepared by recombinant or synthetic methods.

A "native sequence PRO256 polypeptide" comprises a polypeptide having the same amino acid sequence as the corresponding PRO256 polypeptide derived from nature. Such native sequence PRO256 polypeptides can be isolated from nature or can be produced by recombinant or synthetic means. The term "native sequence PRO256 polypeptide" specifically encompasses naturally-occurring truncated or secreted forms of the specific PRO256 polypeptide (e.g., an extracellular domain sequence), naturally-occurring variant forms (e.g., alternatively spliced forms) and naturally-occurring allelic variants of the polypeptide. In various embodiments of the invention, the native sequence PRO256 polypeptides disclosed herein are mature or full-length native sequence polypeptides comprising the full-length amino acids sequences shown in the accompanying figures. Start and stop codons are shown in bold font and underlined in the figures. However, while the PRO256 polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO256 polypeptides.

The PRO256polypeptide "extracellular domain" or "ECD" refers to a form of the PRO256 polypeptide which is essentially free of the transmembrane and cytoplasmic domains. Ordinarily, a PRO256 polypeptide ECD will have less than 1% of such transmembrane and/or cytoplasmic domains and preferably, will have less than 0.5% of such domains. It will be understood that any transmembrane domains identified for the PRO256 polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO256 polypeptide may contain from about 5 or fewer amino acids on either side of the transmembrane domain/extracellular domain boundary as identified in the Examples or specification and such polypeptides, with or without the associated signal peptide, and nucleic acid encoding them, are comtemplated by the present invention.

The approximate location of the "signal peptides" of the various PRO256 polypeptides disclosed herein are shown in the present specification and/or the accompanying figures. It is noted, however, that the C-terminal boundary of a signal peptide may vary, but most likely by no more than about 5amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.*, 10: 1–6 (1997) and von Heinje et al., *Nucl. Acids Res.*, 14:4683–4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO256 polypeptide variant" means an active PRO256 polypeptide as defined above or below having at least about 80% amino acid sequence identity with a full-length native sequence PRO256 polypeptide sequence as disclosed herein, a PRO256 polypeptide sequence lacking the signal peptide as disclosed herein, an extracellular domain of a PRO256 polypeptide, with or without the signal peptide, as disclosed herein or any other fragment of a full-length PRO256 polypeptide sequence as disclosed herein. Such PRO256 polypeptide variants include, for instance, PRO256 polypeptides wherein one or more amino acid residues are added, or deleted, at the N- or C-terminus of the full-length native amino acid sequence. Ordinarily, a PRO256 polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence PRO256 polypeptide sequence as disclosed herein, a PRO256 polypeptide sequence lacking the signal peptide as disclosed herein, an extracellular domain of a PRO256 polypeptide, with or without the signal peptide, as disclosed herein or any other specifically defined fragment of a full-length PRO256 polypeptide sequence as disclosed herein. Ordinarily, PRO256 variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the PRO256 polypeptide sequences identified herein is defined as the percentage of amino acid residues in a candidate sequence that are identical with the amino acid residues in a PRO256 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2, wherein the complete source code for the ALIGN-2 program is provided in Table 1. The ALIGN-2 sequence comparison computer program was authored by Genentech, Inc., and the source code shown in Table 1 has been filed with user documentation in the U.S. Copyright Office, Washington D.C., 20559,where it is registered under U.S. Copyright Registration No. TXU510087. The ALIGN-2 program is publicly available through Genentech, Inc., South San Francisco, Calif. or may be compiled from the source code provided in Table 1. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations, Tables 2–3 demonstrate how to calculate the % amino acid sequence identity of the amino acid sequence designated "Comparison Protein" to the amino acid sequence designated "PRO256".

Unless specifically stated otherwise, all % amino acid sequence identity values used herein are obtained as described above using the ALIGN-2 sequence comparison computer program. However, % amino acid sequence identity may also be determined using the sequence comparison program NCBI-BLAST2 (Altschul et al., *Nucleic Acids Res.*, 25:3389–3402 (1997)). The NCBI-BLAST2 sequence comparison program may be downloaded from the National Institute of Health, Bethesda. Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In addition, % amino acid sequence identity may also be determined using the WU-BLAST-2 computer program (Altschul et al., *Methods in Enzymology*, 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. For purposes herein, a % amino acid sequence identity value is determined by dividing (a) the number of matching identical amino acids residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

"PRO256 variant polynucleotide" or "PRO256 variant nucleic acid sequence" means a nucleic acid molecule which encodes an active PRO256 polypeptide as defined below and which has at least about 80% nucleic acid sequence identity with a nucleotide acid sequence encoding a full-length native sequence PRO256 polypeptide sequence as disclosed herein, a full-length native sequence PRO256 polypeptide sequence lacking the signal peptide as disclosed herein, an extracellular domain of a PRO256 polypeptide, with or without the signal peptide, as disclosed herein or any other fragment of a full-length PRO256 polypeptide sequence as disclosed herein. Ordinarily, a PRO256 variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence PRO256 polypeptide sequence as disclosed herein, a full-length native sequence PRO256 polypeptide sequence lacking the signal peptide as disclosed herein, an extracellular domain of a PRO256 polypeptide, with or without the signal sequence, as disclosed herein or any other fragment of a full-length PRO256 polypeptide sequence as disclosed herein. Variants do not encompass the native nucleotide sequence.

Ordinarily, PRO256 variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to the PRO256 polypeptide-encoding nucleic acid sequences identified herein is defined as the percentage of nucleotides in a candidate sequence that are identical with the nucleotides in a PRO256 polypeptide-encoding nucleic acid sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % nucleic acid sequence identity values are obtained as described below by using the sequence comparison computer program ALIGN-2, wherein the complete source code for the ALIGN-2 program is provided in Table 1. The ALIGN-2 sequence comparison computer program was authored by Genentech, Inc., and the source code shown in Table 1 has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1. The ALIGN-2 program should be compiled for use on a UNIX operating system, preferably digital UNIX V4.0 D. All sequence comparison parameters are set by the ALIGN-2 program and do not vary.

For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4–5 demonstrate how to calculate the % nucleic acid sequence identity of the nucleic acid sequence designated "Comparison DNA" to the nucleic acid sequence designated "PRO-DNA".

Unless specifically stated otherwise, all % amino acid sequence identity values used herein are obtained as described above using the ALIGN-2 sequence comparison computer program. However, % amino acid sequence identity may also be determined using the sequence comparison program NCBI-BLAST2 (Altschul et al., *Nucleic Acids Res.*, 25:3389–3402 (1997) The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scorine matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In addition, % nucleic acid sequence identity values may also be generated using the WU-BLAST-2 computer program (Altschul et al., *Methods in Enzymology*, 266:460–480

(1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. For purposes herein, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

In other embodiments, PRO256 variant polynucleotides are nucleic acid molecules that encode an active PRO256 polypeptide and which are capable of hybridizing, preferably under stringent hybridization and wash conditions, to nucleotide sequences encoding the full-length PRO256 polypeptide as shown in the specification herein and accompanying figures. PRO256 variant polypeptides may be those that are encoded by a PRO256 variant polynucleotide.

"Isolated", when used to describe the various polypeptides disclosed herein, means a polypeptide that has been identified and separated and/or recovered from a component of its natural environment. Preferably, the isolated polypeptide is free of association with all components with which it is naturally associated. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO256 natural environment will not be present. Ordinarily, however, isolated polypeptide will be prepared by at least one purification step.

An "isolated" nucleic acid molecule encoding a PRO256 polypeptide or an "isolated" nucleic acid molecule encoding an anti-PRO256 antibody is a nucleic acid molecule that is identified and separated from at least one contaminant nucleic acid molecule with which it is ordinarily associated in the natural source of the PRO256-encoding nucleic acid or the natural source of the anti-PRO256-encoding nucleic acid. Preferably, the isolated nucleic acid is free of association with all components with which it is naturally associated. An isolated PRO256-encoding nucleic acid molecule or an isolated anti-PRO256-encoding nucleic acid molecule is other than in the form or setting in which it is found in nature. Isolated nucleic acid molecules therefore are distinguished from the PRO256-encoding nucleic acid molecule or from the anti-PRO256-encoding nucleic acid molecule as it exists in natural cells. However, an isolated nucleic acid molecule encoding a PRO256 polypeptide or an isolated nucleic acid molecule encoding an anti-PRO256 antibody includes PRO256-nucleic acid molecules or anti-PRO256-nucleic acid molecules contained in cells that ordinarily express PRO256 polypeptides or anti-PRO256 antibodies where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a PRO256 polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see, Ausubel et al., *Current Protocols in Molecular Biology* (Wiley Interscience Publishers, 1995).

"Stringent conditions" or "high-stringency conditions", as defined herein, may be identified by those that: (1) employ low ionic strength and high temperature for washing, for example, 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately-stringent conditions" may be identified as described by Sambrook et al., *Molecular Cloning: A Labo-*

*ratory Manual* (New York: Cold Spring Harbor Press, 1989), and include the use of washing solution and hybridization conditions (e.g., temperature, ionic strength, and % SDS) less stringent than those described above. An example of moderately stringent conditions is overnight incubation at 37° C in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The modifier "epitope-tagged" when used herein refers to a chimeric polypeptide comprising a PRO256 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" in the context of PRO256 variants refers to form(s) of PRO256 proteins that retain the biologic and/or immunologic activities of a native or naturally-occurring PRO256 polypeptide.

"Biological activity" in the context of a molecule that antagonizes a PRO256 polypeptide that can be identified by the screening assays disclosed herein (e.g., an organic or inorganic small molecule, peptide, etc.) is used to refer to the ability of such molecules to bind or complex with the PRO256 polypeptide identified herein, or otherwise interfere with the interaction of the PRO256 polypeptide with other cellular proteins or otherwise inhibits the transcription or translation of the PRO256 polypeptide. Particularly preferred biological activity includes cardiac hypertrophy, activity that acts on systemic disorders that affect vessels, such as diabetes mellitus, as well as diseases of the arteries, capillaries, veins, and/or lymphatics, and cancer.

The term "antagonist" is used in the broadest sense, and includes any molecule that partially or fully blocks, inhibits, or neutralizes one or more of the biological activities of a native PRO256 polypeptide disclosed herein, for example, inhibition of the activation of the HGF activator polypeptide thereby promoting the mitogenic or angiogenic activity which results from activation of HGF. Antagonists of a PRO256 polypeptide may act by inhibiting the binding of a PRO256 polypeptide to its target HGF activator protein which is responsible for converting the zymogen hepatocyte growth factor into its active form, thereby promoting the mitogenic, angiogenic, or other biological activity of activated HGF. Antagonists of a PRO256 polypeptide may play a role in promoting angiogenesis or tissue repair and therefore may be important for therapeutic revascularization in peripheral vascular disease, in hepatic or renal injury, or restenosis indications.

In a similar manner, the term "agonist" is used in the broadest sense and includes any molecule that mimics a biological activity of a native PRO256 polypeptide disclosed herein. Such agonists are useful for the treatment of diseases or disorders characterized by undesirable excessive neovascularization, including by way of example tumors, and especially solid malignant tumors, rheumatoid arthritis, psoriasis, atherosclerosis, diabetic and other retinopathies, retrolental fibroplasia, age-related macular degeneration, neovascular glaucoma, hemangiomas, thyroid hyperplasias (including Grave's disease), corneal and other tissue transplantation, and chronic inflammation. The agonists also are useful for the treatment of diseases or disorders characterized by undesirable excessive vascular permeability, such as edema associated with brain tumors, ascites associated with malignancies, Meigs' syndrome, lung inflammation, nephrotic syndrome, pericardial effusion (such as that associated with pericarditis), and pleural effusion. Suitable agonist or antagonist molecules specifically include agonist or antagonist antibodies or antibody fragments, fragments, or amino acid sequence variants of native PRO256 polypeptides, peptides, small organic molecules, etc.

A "small molecule" is defined herein to have a molecular weight below about 500 daltons.

The term "PRO256 polypeptide receptor" as used herein refers to a cellular receptor for a PRO256 polypeptide, ordinarily a cell-surface receptor found on vascular endothelial cells, as well as variants thereof that retain the ability to bind a PRO256 polypeptide.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas. The term "antibody" is used in the broadest sense and specifically covers, without limitation, intact monoclonal antibodies, polyclonal antibodies, multispecific antibodies (e.g., bispecific antibodies) formed from at least two intact antibodies, and antibody fragments, so long as they exhibit the desired biological activity.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different imunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody to and for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework regions (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. See, Kabat et al., NIH Publ. No.91–3242, Vol. I, pages 647–669 (1991). The constant domains are not involved directly in binding an antibody to an antigen, but exhibit various effector functions, such as participation of the antibody in antibody-dependent cellular toxicity.

"Antibody fragments" comprise a portion of an intact antibody, preferably the antigen-binding or variable region of the intact antibody. Examples of antibody fragments include Fab, Fab', F(ab')$_2$, and Fv fragments; diabodies; linear antibodies (Zapata et al., Protein Eng., 8(10): 1057–1062 (1995)); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM; and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature,352: 624–628 (1991) and Marks et al., J. Mol. Biol. 222: 581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. U.S. Pat. No. 4,816,567; Morrison et al., Proc. Natl. Acad. Sci. USA, 81: 6851–6855 (1984).

"Humanized" forms of non-human (e.g., murine) antibodies are chimeric immunoglobulins, immunoglobulin chains, or fragments thereof (such as Fv, Fab, Fab', F(ab')$_2$, or other antigen-binding subsequences of antibodies) that contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues that are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody preferably also will comprise at least a portion of an immunoglobulin constant region (Fc), typically that of a human immunoglobulin. For further details, see Jones et al., Nature, 321: 522–525 (1986); Reichmann et al., Nature, 332: 323–329 (1988); and Presta, Curr. Op. Struct. Biol., 2: 593–596 (1992). The humanized antibody includes a PRIMATIZED™ antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of an antibody, wherein these domains are present in a single polypeptide chain. Preferably, the Fv polypeptide further comprises a polypeptide linker between the $V_H$ and $V_L$ domains that enables the sFv to form the desired structure for antigen binding. For a review of sFv see, Pluckthun in *The Pharmacology of Monoclonal Antibodies,* Vol. 113, Rosenburg and Moore, eds. (Springer-Verlag: New York, 1994), pp. 269–315.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90: 6444–6448 (1993).

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells, since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The word "label" when used herein refers to a detectable compound or other composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable. Radionuclides that can serve as detectable labels include, for example, I-131, I-123,I-125, Y-90, Re-188, At-211, Cu-67, Pd-109. The label may also be a non-detectable entity such as a toxin.

By "solid phase" is meant a non-aqueous matrix to which an antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant that is useful for delivery of a drug (such as the PRO256 polypeptide or antibodies thereto disclosed herein) to a mammal. The components of the liposome are commonly arranged in a bilayer formation, similar to the lipid arrangement of biological membranes.

As used herein, the term "immunoadhesin" designates antibody-like molecules that combine the binding specificity of a heterologous protein (an "adhesin") with the effector functions of immunoglobulin constant domains. Structurally, the immunoadhesins comprise a fusion of an amino acid sequence with the desired binding specificity that is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD, or IgM.

As shown below, Table 1 Provides the complete source code for the ALIGN-2 sequence comparison computer program. This source code may be routinely compiled for use on a UNIX operating system to provide the ALIGN-2 sequence comparison computer program.

In addition, Tables 2–5 show hypothetical exemplifications for using the below described method to determine % amino acid sequence identity (Tables 2–3) and % nucleic acid sequence identity (Tables 4–5) using the ALIGN-2 sequence comparison computer program, wherein "PRO" represents the amino acid sequence of a hypothetical PRO polypeptide of interest, "Comparison protein" represents the amino acid sequence of a polypeptide against which the "PRO" polypeptide of interest is being compared, "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, "X", "Y", and "Z" each represent different hypothetical amino acid residues and "N", "L" and "V" each represent different hypothetical nucleotides.

TABLE 1

```
/*
 *
 * C-C increased from 12 to 15
 * Z is average of EQ
/ * B is average of ND
 * match with stop is _M; stop-stop = 0; J (joker) match = 0
 */
#define _M      -8      /* value of a match with a stop */
int _day[26][26] = {
/*      A B C D E F G H I J K L M N O P Q R S T U V W X Y Z */
/*A*/   { 2, 0,-2, 0, 0,-4, 1,-1,-1, 0,-1,-2,-1, 0,_M, 1, 0,-2, 1, 1, 0, 0,-6, 0,-3, 0},
/*B*/   { 0, 3,-4, 3, 2,-5, 0, 1,-2, 0, 0,-3,-2, 2,_M,-1, 1, 0, 0, 0, 0,-2,-5, 0,-3, 1},
```

TABLE 1-continued

```
/*C*/   {-2,-4,15,-5,-5,-4,-3,-3,-2, 0,-5,-6,-5,-4,_M,-3,-5,-4, 0,-2, 0,-2,-8, 0, 0,-5},
/*D*/   { 0, 3,-5, 4, 3,-6, 1, 1,-2, 0, 0,-4,-3, 2,_M,-1, 2,-1, 0, 0, 0,-2,-7, 0,-4, 2},
/*E*/   { 0, 2,-5, 3, 4,-5, 0, 1,-2, 0, 0,-3,-2, 1,_M,-1, 2,-1, 0, 0, 0,-2,-7, 0,-4, 3},
/*F*/   {-4,-5,-4,-6,-5, 9,-5,-2, 1, 0,-5, 2, 0,-4,_M,-5,-5,-4,-3,-3, 0,-1, 0, 0, 7,-5},
/*G*/   { 1, 0,-3, 1, 0,-5, 5,-2,-3, 0,-2,-4,-3, 0,_M,-1,-1,-3, 1, 0, 0,-1,-7, 0,-5, 0},
/*H*/   {-1, 1,-3, 1, 1,-2,-2, 6,-2, 0, 0,-2,-2, 2,_M, 0, 3, 2,-1,-1, 0,-2,-3, 0, 0, 2},
/*I*/   {-1,-2,-2,-2,-2, 1,-3,-2, 5, 0,-2, 2, 2,-2,_M,-2,-2,-2,-1, 0, 0, 4,-5, 0,-1,-2},
/*J*/   { 0, 0, 0, 0, 0, 0, 0, 0, 0, 0, 0, 0, 0, 0,_M, 0, 0, 0, 0, 0, 0, 0, 0, 0, 0, 0},
/*K*/   {-1, 0,-5, 0, 0,-5,-2, 0,-2, 0, 5,-3, 0, 1,_M,-1, 1, 3, 0, 0, 0,-2,-3, 0,-4, 0},
/*L*/   {-2,-3,-6,-4,-3, 2,-4,-2, 2, 0,-3, 6, 4,-3,_M,-3,-2,-3,-3,-1, 0, 2,-2, 0,-1,-2},
/*M*/   {-1,-2,-5,-3,-2, 0,-3,-2, 2, 0, 0, 4, 6,-2,_M,-2,-1, 0,-2,-1, 0, 2,-4, 0,-2,-1},
/*N*/   { 0, 2,-4, 2, 1,-4, 0, 2,-2, 0, 1,-3,-2, 2,_M,-1, 1, 0, 1, 0, 0,-2,-4, 0,-2, 1},
/*O*/   {_M,_M,_M,_M,_M,_M,_M,_M,_M,_M,_M,_M,_M,_M, 0,_M,_M,_M,_M,_M,_M,_M,_M,_M,_M,_M},
/*P*/   { 1,-1,-3,-1,-1,-5,-1, 0,-2, 0,-1,-3,-2,-1,_M, 6, 0, 0, 1, 0, 0,-1,-6, 0,-5, 0},
/*Q*/   { 0, 1,-5, 2, 2,-5,-1, 3,-2, 0, 1,-2,-1, 1,_M, 0, 4, 1,-1,-1, 0,-2,-5, 0,-4, 3},
/*R*/   {-2, 0,-4,-1,-1,-4,-3, 2,-2, 0, 3,-3, 0, 0,_M, 0, 1, 6, 0,-1, 0,-2, 2, 0,-4, 0},
/*S*/   { 1, 0, 0, 0, 0,-3, 1,-1,-1, 0, 0,-3,-2, 1,_M, 1,-1, 0, 2, 1, 0,-1,-2, 0,-3, 0},
/*T*/   { 1, 0,-2, 0, 0,-3, 0,-1, 0, 0, 0,-1,-1, 0,_M, 0,-1,-1, 1, 3, 0, 0,-5, 0,-3, 0},
/*U*/   { 0, 0, 0, 0, 0, 0, 0, 0, 0, 0, 0, 0, 0, 0,_M, 0, 0, 0, 0, 0, 0, 0, 0, 0, 0, 0},
/*V*/   { 0,-2,-2,-2,-2,-1,-1,-2, 4, 0,-2, 2, 2,-2,_M,-1,-2,-2,-1, 0, 0, 4,-6, 0,-2,-2},
/*W*/   {-6,-5,-8,-7,-7, 0,-7,-3,-5, 0,-3,-2,-4,-4,_M,-6,-5, 2,-2,-5, 0,-6,17, 0,-6},
/*X*/   { 0, 0, 0, 0, 0, 0, 0, 0, 0, 0, 0, 0, 0, 0,_M, 0, 0, 0, 0, 0, 0, 0, 0, 0, 0, 0},
/*Y*/   {-3,-3, 0,-4,-4, 7,-5, 0,-1, 0,-4,-1,-2,-2,_M,-5,-4,-4,-3,-3, 0,-2, 0, 0,10,-4},
/*Z*/   { 0, 1,-5, 2, 3,-5, 0, 2,-2, 0, 0,-2,-1, 1,_M, 0, 3, 0, 0, 0, 0,-2,-6, 0,-4, 4}
};
/*
 */
#include    <stdio.h>
#include    <ctype.h>
#define     MAXJMP      16          /* max jumps in a diag */
#define     MAXGAP      24          /* don't continue to penalize gaps larger than this */
#define     JMPS        1024        /* max jmps in an path */
#define     MX          4           /* save if there's at least MX-1 bases since last jmp */
#define     DMAT        3           /* value of matching bases */
#define     DMIS        0           /* penalty for mismatched bases */
#define     DINS0       8           /* penalty for a gap */
#define     DINS1       1           /* penalty per base */
#define     PINS0       8           /* penalty for a gap */
#define     PINS1       4           /* penalty per residue */
struct jmp {
    short               n[MAXJMP];       /* size of jmp (neg for dely) */
    unsigned short      x[MAXJMP];       /* base no. of jmp in seq x */
};                                       /* limits seq to 2^16 -1 */
struct diag {
    int         score;              /* score at last jmp */
    long        offset;             /* offset of prev block */
    short       ijmp;               /* current jmp index */
    struct jmp  jp;                 /* list of jmps */
};
struct path {
    int spc;                        /* number of leading spaces */
    short       n[JMPS];            /* size of jmp (gap) */
    int         x[JMPS];            /* loc of jmp (last elem before gap) */
};
char    *ofile;                     /* output file name */
char    *namex[2];                  /* seq names: getseqs() */
char    *prog;                      /* prog name for err msgs */
char    *seqx[2];                   /* seqs: getseqs() */
int     dmax;                       /* best diag: nw() */
int     dmax0;                      /* final diag */
int     dna;                        /* set if dna: main() */
int     endgaps;                    /* set if penalizing end gaps */
int     gapx, gapy;                 /* total gaps in seqs */
int     len0, len1;                 /* seq lens */
int     ngapx, ngapy;               /* total size of gaps */
int     smax;                       /* max score: nw() */
int     *xbm;                       /* bitmap for matching */
long    offset;                     /* current offset in jmp file */
struct  diag    *dx;                /* holds diagonals */
struct  path    pp[2];              /* holds path for seqs */
char    *calloc(), *malloc(), *index(), *strcpy();
char    *getseq(), *g_calloc();
/* Needleman-Wunsch alignment program
 *
 * usage: progs file1 file2
 * where file1 and file2 are two dna or two protein sequences.
 * The sequences can be in upper- or lower-case an may contain ambiguity
 * Any lines beginning with ';','>' or '<' are ignored
 * Max file length is 65535 (limited by unsigned short x in the jmp struct)
```

TABLE 1-continued

```
* A sequence with 1/3 or more of its elements ACGTU is assumed to be DNA
* Output is in the file "align.out"
*
* The program may create a tmp file in /tmp to hold info about traceback.
* Original version developed under BSD 4.3 on a vax 8650
*/
#include "nw.h"
#include "day.h"
static       _dbval[26] = {
    1,14,2,13,0,0,4,11,0,0,12,0,3,15,0,0,0,5,6,8,8,7,9,0,10,0
};
static       _pbval[26] = {
    1, 2|(1<<('D'-'A'))|(1<<('N'-'A')), 4, 8, 16, 32, 64,
    128, 256, 0xFFFFFFFF, 1<<10, 1<<11, 1<<12, 1<<13, 1<<14,
    1<<15, 1<<16, 1<<17, 1<<18, 1<<19, 1<<20, 1<<21, 1<<22,
    1<<23, 1<<24, 1<<25|(1<<('E'-'A'))|(1<<('Q'-'A'))
};
main(ac, av)                                                                    main
    int   ac;
    char  *av[ ];
{
    prog = av[0];
    if (ac != 3) {
        fprintf(stderr,"usage: %s file1 file2\n", prog);
        fprintf(stderr,"where file1 and file2 are two dna or two protein sequences.\n");
        fprintf(stderr,"The sequences can be in upper- or lower-case\n");
        fprintf(stderr,"Any lines beginning with ';' or '<' are ignored\n");
        fprintf(stderr,"Output is in the file \"align.out\"\n");
        exit(1);
    }
    namex[0] = av[1];
    namex[1] = av[2];
    seqx[0] = getseq(namex[0], &len0);
    seqx[1] = getseq(namex[1], &len1);
    xbm = (dna)? _dbval : _pbval;
    endgaps = 0;                /* 1 to penalize endgaps */
    ofile = "align.out";        /* output file */
    nw( );                      /* fill in the matrix, get the possible jmps */
    readjmps( );  /* get the actual jmps */
    print( );                   /* print stats, alignment */
    cleanup(0);   /* unlink any tmp files */
}
/* do the alignment, return best score: main( )
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw( )                                                                           nw
{
    char          *px, *py;         /* seqs and ptrs */
    int     *ndely, *dely;          /* keep track of dely */
    int     ndelx, delx;            /* keep track of delx */
    int     *tmp;                   /* for swapping row0, row1 */
    int     mis;                    /* score for each type */
    int     ins0, ins1;             /* insertion penalties */
    register          id;           /* diagonal index */
    register          ij;           /* jmp index */
    register    *col0, *col1;       /* score for curr, last row */
    register    xx, yy;             /* index into seqs */
    dx = (struct diag *)g_calloc("to get diags", len0+len1+1, sizeof(struct diag));
    ndely = (int *)g_calloc("to get ndely", len1+1, sizeof(int));
    dely = (int *)g_calloc("to get dely", len1+1, sizeof(int));
    col0 = (int *)g_calloc("to get col0", len1+1, sizeof(int));
    col1 = (int *)g_calloc("to get col1", len1+1, sizeof(int));
    ins0 = (dna)? DINS0 : PINS0;
    ins1 = (dna)? DINS1 : PINS1;
    smax = -10000;
    if (endgaps) {
        for (col0[0] = dely[0] = -ins0, yy = 1; yy <= len1; yy++) {
            col0[yy] = dely[yy] = col0[yy-1] -ins1;
            ndely[yy] = yy;
        }
        col0[0] = 0;   /* Waterman Bull Math Biol 84 */
    }
    else
        for (yy = 1; yy <= len1; yy++)
            dely[yy] = -ins0;
```

TABLE 1-continued

```
        /* fill in match matrix
         */
        for (px = seqx[0], xx = 1; xx <= len0; px++, xx++) {
            /* initialize first entry in col
             */
            if (endgaps) {
                if (xx == 1)
                    col1[0] = delx = -(ins0+ins1);
                else
                    col1[0] = delx = col0[0] - ins1;
                ndelx = xx;
            }
            else {
                col1[0] = 0;
                delx = -ins0;
                ndelx = 0;
            }
                                                                                            ...nw
for (py = seqx[1], yy = 1; yy <= len1; py++, yy++) {
    mis = col0[yy-1];
    if (dna)
        mis += (xbm[*px-'A']&xbm[*py-'A'])? DMAT : DMIS;
    else
        mis += (_day[*px-'A'][*py-'A'];
    /* update penalty for del in x seq;
     * favor new del over ongong del
     * ignore MAXGAP if weighting endgaps
     */
    if (endgaps || ndely[yy] < MAXGAP) {
        if (col0[yy] -ins0 >= dely[yy]) {
            dely[yy] = col0[yy] - (ins0+ins1);
            ndely[yy] = 1;
        } else {
            dely[yy] -= ins1;
            ndely[yy]++;
        }
    } else {
        if (col0[yy] - (ins0+ins1) >= dely[yy]) {
            dely[yy]= col0[yy] - (ins0+ins1);
            ndely[yy] = 1;
        } else
            ndely[yy]++;
    }
    /* update penalty for del in y seq;
     * favor new del over ongong del
     */
    if (endgaps || ndelx < MAXGAP) {
        if (col1[yy-1] - ins0 >= delx) {
            delx = col1[yy-1] - (ins0+ins1);
            ndelx = 1;
        } else {
            delx -= ins1;
            ndelx++;
        }
    } else {
        if (col1[yy-1] - (ins0+ins1) >= delx) {
            delx = col1[yy-1] - (ins0+ins1);
            ndelx = 1;
        } else
            ndelx++;
    }
    /* pick the maximum score; we're favoring
     * mis over any del and delx over dely
     */
                                                                                            ...nw
        id = xx - yy + len1 -1;
        if (mis >= delx && mis >= dely[yy])
            col1[yy] = mis;
        else if (delx >= dely[yy]) {
            col1[yy] = delx;
            ij = dx[id].ijmp;
            if (dx[id].jp.n[0]&& (!dna || (ndelx >= MAXJMP
                && xx > dx[id].jp.x[ij]+MX) || mis > dx[id].score+DINS0)) {
                    dx[id].ijmp++
                    if (++ij >= MAXJMP) {
                        writejmps(id);
                        ij = dx[id].ijmp = 0;
                        dx[id].offset = offset;
                        offset += sizeof(struct jmp) + sizeof(offset);
```

TABLE 1-continued

```
                        }
                    }
                    dx[id].jp.n[ij] = ndelx;
                    dx[id].jp.x[ij] = xx;
                    dx[id].score = delx;
                }
                else {
                    col1[yy] = dely[yy];
                    ij = dx[id].ijmp;
if (dx[id].jp.n[0] && (!dna || (ndely[yy] >= MAXJMP
                && xx > dx[id].jp.x[ij]+MX) || mis > dx[id].score+DINS0)) {
                        dx[id].ijmp++;
                            if (++ij >= MAXJMP) {
                                writejmps(id);
                                ij = dx[id].ijmp = 0;
                                dx[id].offset = offset;
                                offset += sizeof(struct jmp) + sizeof(offset);
                            }
                    }
                    dx[id].jp.n[ij] = -ndely[yy];
                    dx[id].jp.x[ij] = xx;
                    dx[id].score = dely[yy];
                }
            if (xx == len0 && yy < len1) {
                /* last col
                 */
                if (endgaps)
                    col1[yy] -= ins0+ins1*(len1-yy);
                if (col1[yy] > smax) {
                    smax = col1[yy];
                    dmax = id;
                }
            }
        }
        if (endgaps && xx < len0)
            col1[yy-1] -= ins0+ins1*(len0-xx);
        if (col1[yy-1] > smax) {
            smax = col1[yy-1];
            dmax = id;
        }
        tmp = col0; col0 = col1; col1 = tmp;
    }
    (void) free((char *)ndely);
    (void) free((char *)dely);
    (void) free((char *)col0);
    (void) free((char *)col1);                          }
/*
 *
 * print( ) -- only routine visible outside this module
 *
 * static:
 * getmat( ) -- trace back best path, count matches: print( )
 * pr_align( ) -- print alignment of described in array p[ ]: print( )
 * dumpblock( ) -- dump a block of lines with numbers, stars: pr_align( )
 * nums( ) -- put out a number line: dumpblock( )
 * putline( ) -- put out a line (name, [num], seq, [num]): dumpblock( )
 * stars( ) -- put a line of stars: dumpblock( )
 * stripname( ) -- strip any path and prefix from a seqname
 */
#include "nw.h"
#define SPC     3
#define P_LINE  256     /* maximum output line */
#define P_SPC   3       /* space between name or num and seq */
extern   _day[26][26];
int   olen;             /* set output line length */
FILE  *fx;              /* output file */
print( )                                                                    print
{
    int lx, ly, firstgap, lastgap;     /* overlap */
    if ((fx = fopen(ofile, "w")) == 0) {
        fprintf(stderr,"%s: can't write %s\n", prog, ofile);
        cleanup(1);
    }
    fprintf(fx, "<first sequence: %s (length = %d)\n", namex[0], len0);
    fprintf(fx, "<second sequence: %s (length = %d)\n", namex[1], len1);
    olen = 60;
    lx = len0;
    ly = len1;
    firstgap = lastgap = 0;
```

TABLE 1-continued

```
        if (dmax < len1 - 1) {        /* leading gap in x */
            pp[0].spc = firstgap = len1 - dmax - 1;
            ly -= pp[0].spc;
        }
        else if (dmax > len1 - 1) {   /* leading gap in y */
            pp[1].spc = firstgap = dmax - (len1 - 1);
            lx -= pp[1].spc;
        }
        if (dmax0 < len0 - 1) {       /* trailing gap in x */
            lastgap = len0 - dmax0 - 1;
            lx -= lastgap;
        }
        else if (dmax0 > len0 - 1) {  /* trailing gap in y */
            lastgap = dmax0 - (len0 - 1);
            ly -= lastgap;
        }
        getmat(lx, ly, firstgap, lastgap);
        pr_align( );
}
/*
 * trace back the best path, count matches
 */
static
getmat(lx, ly, firstgap, lastgap)                                                    getmat
    int     lx, ly;              /* "core" (minus endgaps) */
    int     firstgap, lastgap;   /* leading trailing overlap */
{
    int         nm, i0, i1, siz0, siz1;
    char        outx[32];
    double      pct;
    register    n0, n1;
    register char  *p0, *p1;
    /* get total matches, score
     */
    i0 = i1 = siz0 = siz1 = 0;
    p0 = seqx[0] + pp[1].spc;
    p1 = seqx[1] + pp[0].spc;
    n0 = pp[1].spc + 1;
    n1 = pp[0].spc + 1;
    nm = 0;
    while ( *p0 && *p1 ) {
        if (siz0) {
            p1 ++;
            n1 ++;
            siz0--;
        }
        else if (siz1) {
            p0 ++;
            n0 ++;
            siz1--;
        }
        else {
            if (xbm[*p0-'A']&xbm[*p1-'A'])
                nm++;
            if (n0++ == pp[0].x[i0])
                siz0 = pp[0].n[i0++];
            if (n1 ++ == pp[1].x[i1])
                siz1 = pp[1].n[i1++];
            p0++;
            p1++:
        }
    }
    /* pct homology:
     * if penalizing endgaps, base is the shorter seq
     * else, knock off overhangs and take shorter core
     */
    if (endgaps)
        lx = (len0 < len1)? len0 : len1;
    else
        lx = (lx < ly)? lx : ly;
    pct = 100.*(double)nm/(double)lx;
    fprintf(fx, "\n");
    fprintf(fx, "<%d match%s in an overlap of %d: % .2f percent similarity\n",
        nm, (nm == 1)? " " : "es", lx, pct);
    fprintf(fx, "<gaps in first sequence: %d", gapx);                                ...getmat
    if (gapx) {
        (void) sprintf(outx, " (%d %s%s)",
            ngapx, (dna)? "base": "residue", (ngapx == 1)? " " : "s");
        fprintf(fx, "%s", outx);
```

TABLE 1-continued

```
        fprintf(fx, ", gaps in second sequence: %d", gapy);
        if (gapy) {
            (void) sprintf(outx, " (%d %s%s)",
                ngapy, (dna)? "base":"residue", (ngapy == 1)? " ":"s");
            fprintf(fx, "%s", outx);
        }
        if (dna)
            fprintf(fx,
                "\n<score: %d (match = %d, mismatch = %d, gap penalty = %d + %d per base)\n",
                smax, DMAT, DMIS, DINS0, DINS1);
        else
            fprintf(fx,
                "\n<score: %d (Dayhoff PAM 250 matrix, gap penalty = %d + %d per residue)\n",
                smax, PINS0, PINS1);
        if (endgaps)
            fprintf(fx,
                "<endgaps penalized. left endgap: %d %s%s, right endgap: %d %s%s\n",
                firstgap, (dna)? "base" : "residue", (firstgap == 1)? " " : "s",
                lastgap, (dna)? "base" : "residue", (lastgap == 1)? " " : "s");
        else
            fprintf(fx, "<endgaps not penalized\n");
}
static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars( ) */
/*
* print alignment of described in struct path pp[ ]
*/
static
pr_align( )                                                                         pr_align
{
    int     nn;         /* char count */
    int     more;
    register        i;
    for (i = 0, lmax = 0; i < 2; i++) {
        nn = stripname(namex[i]);
        if (nn > lmax)
            lmax = nn;
        nc[i] = 1;
        ni[i] = 1;
        siz[i] = ij[i] = 0;
        ps[i] = seqx[i];
        po[i] = out[i];         }
    for (nn = nm = 0, more = 1; more; ) {                                           ...pr_align
        for (i = more = 0; i < 2; i++) {
            /*
            * do we have more of this sequence?
            */
            if (!*ps[i])
                continue;
            more++;
            if (pp[i].spc) {    /* leading space */
                *po[i]++ = ' ';
                pp[i].spc--;
            }
            else if (siz[i]) {  /* in a gap */
                *po[i]++ = '-';
                siz[i]--;
            }
            else {              /* we're putting a seq element
                                */
                *po[i] = *ps[i];
                if (islower(*ps[i]))
                    *ps[i] = toupper(*ps[i]);
                po[i]++;
                ps[i]++;
                /*
                * are we at next gap for this seq?
                */
                if (ni[i] == pp[i].x[ij[i]]) {
                    /*
                    * we need to merge all gaps
```

TABLE 1-continued

```
                                    * at this location
                                    */
                                   siz[i] = pp[i].n[ij[i]++];
                                   while (ni[i] == pp[i].x[ij[i]])
                                           siz[i] += pp[i].n[ij[i]++];
                           }
                           ni[i]++;
                   }
           }
           if(++nn == olen || !more && nn) {
                   dumpblock( );
                   for (i = 0; i < 2; i++)
                           po[i] = out[i];
                   nn = 0;
           }
       }
}
/*
 * dump a block of lines, including numbers, stars: pr_align( )
 */
static
dumpblock( )                                                                            dumpblock
{
    register      i;
    for(i = 0; i < 2; i++)
        *po[i]-- = '\0';
                                                                                        ...dumpblock
    (void) putc('\n', fx);
    for (i =0; i <2; i++){
        if (*out[i] && (*out[i] != ' ' || *(po[i]) != ' ')) {
            if (i == 0)
                    nums(i);
            if (i == 0 && *out[1])
                    stars( );
            putline(i);
            if (i == 0 && *out[1])
                    fprintf(fx, star);
            if (i == 1)
                    nums(i);
        }
    }
}
/*
 * put out a number line: dumpblock( )
 */
static
nums(ix)                                                                                nums
        int ix;    /* index in out[ ] holding seq line */
{
    char           nline[P_LINE];
    register       i, j;
    register char  *pn, *px, *py;
    for (pn = nline, i = 0; i < lmax+P_SPC; i++, pn++)
        *pn = ' ';
    for (i = nc[ix], py = out[ix]; *py; py++, pn++) {
        if (*py == ' ' || *py == '-')
            *pn = ' ';
        else {
            if(i%10 == 0 || (i == 1 && nc[ix] != 1)) {
                    j = (i < 0)? -i :i;
                    for (px = pn; j; j /= 10, px--)
                            *px = j%10 + '0';
                    if (i < 0)
                            *px = '-';
            }
            else
                    *pn = ' ';
            i++;
        }
    }
    *pn = '\0';
    nc[ix] = i;
    for (pn = nline; *pn; pn++)
        (void) putc(*pn, fx);
    (void) putc('\n', fx);
}
/*
 * put out a line (name, [num], seq, [num]): dumpblock( )
 */
```

TABLE 1-continued

```
static
putline(ix)                                                                                      putline
    int ix;                    {
                                                                                                 ...putline
        int     i;
        register char   *px;
        for (px = namex[ix], i = 0; *px && *px != ':'; px++, i++)
            (void) putc(*px, fx);
        for (; i < lmax+P_SPC; i++)
            (void) putc(' ', fx);
        /* these count from 1:
         * ni[ ]is current element (from 1)
         * nc[ ]is number at start of current line
         */
        for (px = out[ix]; *px; px++)
            (void) putc(*px&0x7F, fx);
        (void) putc('\n', fx);
}
/*
 * put a line of stars (seqs always in out[0], out[1]): dumpblock( )
 */
static
stars( )                                                                                         stars
{
    int     i;
    register char   *p0, *p1, cx, *px;
    if(!*out[0] || (*out[0] == ' ' && *(po[0]) == ' ') ||
       !*out[1] || (*out[1] == ' ' && *(po[1]) == ' '))
        return;
    px = star;
    for (i = lmax+P_SPC; i; i--)
        *px++ = ' ';
    for (p0 = out[0],p1 = out[1]; *p0 && *p1; p0++, p1++) {
        if (isalpha(*p0) && isalpha(*p1)) {
            if (xbm[*p0-'A']&xbm[*p1-'A']) {
                cx = '*';
                nm++;
            }
            else if (!dna && _day[*p0-'A'][*p1-'A'] > 0)
                cx = '.';
            else
                cx = ' ';
        }
        else
            cx = ' ';
        *px ++ = cx;
    }
    *px ++ = '\n';
    *px = '\0';
}
/*
 * strip path or prefix from pn, return len: pr_align( )
 */
static
stripname(pn)                                                                                    stripname
    char    *pn;    /* file name (may be path) */
{
    register char   *px, *py;
    py = 0;
    for (px = pn; *px; px++)
        if(*px == '/')
            py = px + 1;
    if (py)
        (void) strcpy(pn, py);
    return(strlen(pn));
}
/*
 * cleanup( ) -- cleanup any tmp file
 * getseq( ) -- read in seq, set dna, len, maxlen
 * g_calloc( ) -- calloc( ) with error checkin
 * readjmps( ) -- get the good jmps, from tmp file if necessary
 * writejmps( ) -- write a filled array of jmps to a tmp file: nw( )
 */
#include "nw.h"
#include <sys/file.h>
char    *jname = "/tmp/homgXXXXXX";     /* tmp file for jmps */
FILE    *fj;
int     cleanup( );             /* cleanup tmp file */
long    lseek( );
```

TABLE 1-continued

```
/*
 * remove any tmp file if we blow
 */
cleanup(i)                                                                                          cleanup
        int i;
{
        if (fj)
                (void) unlink(jname);
        exit(i);
}
/*
 * read, return ptr to seq, set dna, len, maxlen
 * skip lines starting with ';', '<', or '>'
 * seq in upper or lower case
 */
char *
getseq(file, len)                                                                                   getseq
        char       *file;   /* file name */
        int *len;  /* seq len */
{
        char              line[1024], *pseq;
        register char     *px, *py;
        int       natgc, tlen;
        FILE              *fp;
        if ((fp = fopen(file,"r")) == 0) {
                fprintf(stderr, "%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for(px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc( ) failed to get %d bytes for %s\n", prog, tlen+6, file);
                exit(1);
        }
        pseq[0] = pseq[1] = pseq[2] = pseq[3] = '\0';
                                                                                                    ...getseq
        py = pseq + 4;
        *len = tlen;
        rewind(fp);
        while (fgets(line, 1024, fp)) {
                if (*line == ';' || *line == '<' || *line == '>')
                        continue;
                for (px = line; *px != '\n'; px++) {
                        if (isupper(*px))
                                *py ++ = *px;
                        else if (islower(*px))
                                *py ++ = toupper(*px);
                        if (index("ATGCU",*(py-1)))
                                natgc ++;
                }
        }
        *py ++ = '\0';
        *py = '\0';
        (void) fclose(fp);
        dna = natgc > (tlen/3);
        return(pseq+4);
}
char *
g_calloc(msg, nx, sz)                                                                               g_calloc
        char       *msg;    /* program, calling routine */
        int, nx, sz;        /* number and size of elements */
{
        char       *px, *calloc( );
        if ((px = calloc((unsigned)nx, (unsigned)sz)) == 0) {
                if (*msg) {
                        fprintf(stderr, "%s: g_calloc( ) failed %s (n=%d, sz=%d)\n", prog, msg, nx, sz);
                        exit(1);
                }
        }
        return(px);
}
/*
 * get final jmps from dx[ ] or tmp file, set pp[ ], reset dmax: main( )
```

TABLE 1-continued

```
*/
readjmps( )                                                                                    readjmps
{
        int     fd = -1;
        int     siz, i0, i1;
        register i, j, xx;
        if (fj) {
                (void) fclose(fj);
                if ((fd = open(jname, O_RDONLY, 0)) < 0) {
                        fprintf(stderr, "%s: can't open( ) %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
                                                                                            ...readjmps
                        if (j < 0 && dx[dmax].offset && fj) {
                                (void) lseek(fd, dx[dmax].offset, 0);
                                (void) read(fd, (char *)&dx[dmax].jp, sizeof(struct jmp));
                                (void) read(fd, (char *)&dx[dmax]offset, sizeof(dx[dmax].offset));
                                dx[dmax].ijmp = MAXJMP-1;
                        }
                        else
                                break;
                }
                if (i >= JMPS) {
                        fprintf(stderr, "%s: too many gaps in alignment\n", prog);
                        cleanup(1);
                }
                if (j >= 0) {
                        siz = dx[dmax].jp.n[j];
                        xx = dx[dmax].jp.x[j];
                        dmax += siz;
                        if (siz < 0) {          /* gap in second seq */
                                pp[1].n[i1] = -siz;
                                xx += siz;
                                /* id = xx - yy + len1 - 1
                                 */
                                pp[1].x[i1]= xx - dmax + len1 - 1;
                                gapy ++;
                                ngapy -= siz;
/* ignore MAXGAP when doing endgaps */
                                siz = (-siz < MAXGAP || endgaps)? -siz : MAXGAP;
                                i1 ++;
                        }
                        else if (siz > 0) {    /* gap in first seq */
                                pp[0].n[i0] = siz;
                                pp[0].x[i0] = xx;
                                gapx ++;
                                ngapx += siz;
/* ignore MAXGAP when doing endgaps */
                                siz = (siz < MAXGAP || endgaps)? siz : MAXGAP;
                                i0++;
                        }
                }
                else
                        break;
        }
        /* reverse the order of jmps
         */
        for (j = 0, i0--; j < i0; j++, i0--) {
                i = pp[0].n[j]; pp[0].n[j] = pp[0].n[i0]; pp[0].n[i0] = i;
                i = pp[0].x[j]; pp[0].x[j] = pp[0].x[i0]; pp[0].x[i0] = i;
        }
        for (j = 0, i1--; j < i1; j++, i1--) {
                i = pp[1].n[j]; pp[1].n[j] = pp[1].n[i1]; pp[1].n[i1] = i;
                i = pp[1].x[j]; pp[1].x[j] = pp[1].x[i1]; pp[1].x[i1] = i;
        }
        if (fd >= 0)
                (void) close(fd);
        if (fj) {
                (void) unlink(jname);
                fj = 0;
                offset = 0;     }                               }
/*
 * write a filled jmp struct offset of the prev one (if any): nw( )
 */
```

TABLE 1-continued

```
writejmps(ix)                                                                writejmps
    int ix;
{
    char    *mktemp( );
    if (!fj) {
        if (mktemp(jname) < 0) {
            fprintf(stderr, "%s: can't mktemp( ) %s\n", prog, jname);
            cleanup(1);
        }
        if ((fj = fopen(jname, "w")) == 0) {
            fprintf(stderr, "%s: can't write %s\n", prog, jname);
            exit(1);
        }
    }
    (void) fwrite((char *)&dx[ix].jp, sizeof(struct jmp), 1, fj);
    (void) fwrite((char *)&dx[ix].offset, sizeof(dx[ix].offset), 1, fj);
}
```

TABLE 2

```
PRO              XXXXXXXXXXXXXXX   (Length = 15 amino acids)

Com-             XXXXXYYYYYYY      (Length = 12 amino acids)
parison
Protein
```

% amino acid sequence identity = (the number of
identically matching amino acid residues between
the two polypeptide sequences as determined by
ALIGN-2) divided by (the total number of amino acid
residues of the PRO polypeptide) = 5 divided by
15 = 33.3%

TABLE 3

```
PRO              XXXXXXXXXX        (Length = 10 amino acids)

Com-             XXXXXYYYYYZZYZ    (Length = 15 amino acids)
parison
Protein
```

% amino acid sequence identity = (the number of
identically matching amino acid residues between
the two polypeptide sequences as determined by
ALIGN-2) divided by (the total number of amino acid
residues of the PRO polypeptide) = 5 divided by
10 = 50%

TABLE 4

```
PRO-DNA  NNNNNNNNNNNNNN   (Length = 14 nucleotides)

Com-     NNNNNNLLLLLLLLLL (Length = 16 nucleotides)
parison
DNA
```

% nucleic acid sequence identity = (the number of
identically matching nucleotides between the two
nucleic acid sequences as determined by ALIGN-2)
divided by (the total number of nucleotides of the
PRO-DNA nucleic acid sequence) = 6 divided by
14 = 42.9%

TABLE 5

```
PRO-DNA      NNNNNNNNNNNN  (Length = 12 nucleotides)

Comparison   NNNNLLLVV     (Length = 9 nucleotides)
DNA
```

% nucleic acid sequence identity = (the number of
identically matching nucleotides between the two
nucleic acid sequences as determined by ALIGN-2)
divided by (the total number of nucleotides of the
PRO-DNA nucleic acid sequence) = 4 divided by
12=33.3%

II. Compositions and Methods of the Invention

A. PRO256 Variants

In addition to the full-length native sequence PRO256 polypeptides described herein, it is contemplated that PRO256 variants can be prepared. PRO256 variants can be prepared by introducing appropriate nucleotide changes into the PRO256 DNA, and/or by synthesis of the desired PRO256 polypeptide. Those skilled in the art will appreciate that amino acid changes may alter post-translational processes of the PRO256 polypeptide such as changing the number or position of glycosylation sites or altering the membrane anchoring characteristics.

Variations in the native full-length sequence PRO256 polypeptide or in various domains of the PRO256 polypeptide described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO256 polypeptide that results in a change in the amino acid sequence of the PRO256 polypeptide as compared with the native sequence PRO256 epolypetide. Optionally the variation is by substitution of at least one amino acid with any other amino acid in one or more of the domains of the PRO256 polypeptide. Guidance in determining which amino acid residue may be inserted, substituted or deleted without adversely affecting the desired activity may be found by comparing the sequence of the PRO256 polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| PRO (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO256 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gin, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene* 34:315 (1985)], restriction selection mutagenesis [Wells et al., *Philos. Trans. R. Soc. London SerA*, 317:415 (1986)] or other known techniques can be performed on the cloned DNA to produce the PRO256 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081–1085 (1989)]. Alanine is also typically preferred because it is the most common amino acid. Further, it is frequently found in both buried and exposed positions [Creighton, *The Proteins*, (W. H. Freeman & Co., N.Y.); Chothia, *J. Mol. Biol.*, 150:1 (1976)]. If alanine substitution does not yield adequate amounts of variant, an isoteric amino acid can be used.

B. Modifications of PRO256 Polypeptides

Covalent modifications of PRO256 polypeptides are included within the scope of this invention. One type of covalent modification includes reacting targeted amino acid residues of a PRO256 polypeptide with an organic derivatizing agent that is capable of reacting with selected side chains or the N- or C-terminal residues of the PRO256 polypeptide. Derivatization with bifunctional agents is useful, for instance, for crosslinking the PRO256 polypeptide to a water-insoluble support matrix or surface for use in the method for purifying anti-PRO256 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3 '-dithiobis(succinimidylpropionate), bifunctional maleimides such as bis-N-maleimido-1,8-octane and agents such as methyl-3-[(p-azidophenyl)-dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chains [T. E. Creighton, *Proteins: Structure and Molecular Properties,* W. H. Freeman & Co., San Francisco, pp. 79–86 (1983)], acetylation of the N-terminal amine, and amidation of any C-terminal carboxyl group.

Another type of covalent modification of the PRO256 polypeptide included within the scope of this invention comprises altering the native glycosylation pattern of the polypeptide. "Altering the native glycosylation pattern" is intended for purposes herein to mean deleting one or more carbohydrate moieties found in the native sequence PRO256 polypeptide (either by removing the underlying glycosylation site or by deleting the glycosylation by chemical and/or enzymatic means), and/or adding one or more glycosylation sites that are not present in the native sequence PRO256 polypeptide. In addition, the phrase includes qualitative changes in the glycosylation of the native proteins, involving a change in the nature and proportions of the various carbohydrate moieties present.

Addition of glycosylation sites to the PRO256 polypeptide may be accomplished by altering the amino acid sequence. The alteration may be made, for example, by the addition of, or substitution by, one or more serine or threonine residues to the native sequence PRO256 polypeptide (for O-linked glycosylation sites). The PRO256 amino acid sequence may optionally be altered through changes at the DNA level, particularly by mutating the DNA encoding the PRO256 polypeptide at preselected bases such that codons are generated that will translate into the desired amino acids.

Another means of increasing the number of carbohydrate moieties on the PRO256 polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem., pp.* 259–306 (1981).

Removal of carbohydrate moieties present on the PRO256 polypeptide may be accomplished chemically or enzymatically or by mutational substitution of codons encoding for amino acid residues that serve as targets for glycosylation.

Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of the PRO256 polypeptide comprises linking the PRO256 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO256 polypeptide of the present invention may also be modified in a way to form a chimeric molecule comprising the PRO256 polypeptide fused to another, heterologous polypeptide or amino acid sequence.

In one embodiment, such a chimeric molecule comprises a fusion of the PRO256 polypeptide with a tag polypeptide which provides an epitope to which an anti-tag antibody can selectively bind. The epitope tag is generally placed at the amino- or carboxyl-terminus of the PRO256 polypeptide. The presence of such epitope-tagged forms of the PRO256 polypeptide can be detected using an antibody against the tag polypeptide. Also, provision of the epitope tag enables the PRO256 polypeptide to be readily purified by affinity purification using an anti-tag antibody or another type of affinity matrix that binds to the epitope tag. Various tag polypeptides and their respective antibodies are well known in the art. Examples include poly-histidine (poly-His) or poly-histidine-glycine (poly-His-gly) tags; the flu HA tag polypeptide and its antibody 12CA5[Field et al., *Mol. Cell. Biol.* 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553(1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

In an alternative embodiment, the chimeric molecule may comprise a fusion of the PRO256 polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO256 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also, U.S. Pat. No. 5,428,130 issued Jun. 27, 1995.

C. Preparation of the PRO256 Polypeptide

The present invention provides newly identified and isolated nucleotide sequences encoding polypeptides referred to in the present application as PRO256 polypeptides. In particular, cDNAs encoding PRO256 polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the PRO DNA as well as all further native homologues and variants included in the foregoing definition of PRO256 polypeptides, will be referred to as "PRO256" regardless of their origin or mode of preparation.

The description below relates primarily to production of PRO256 polypeptides by culturing cells transformed or transfected with a vector containing nucleic acid encoding PRO256 polypeptides. It is, of course, contemplated that alternative methods that are well known in the art may be employed to prepare the PRO256 polypeptide. For instance, the PRO256 polypeptide sequence, or portions thereof, may be produced by direct peptide synthesis using solid-phase techniques. See, e.g., Stewart et al., *Solid-Phase Peptide Synthesis* (W.H. Freeman Co.: San Francisco, Calif., 1969); Merrifield, *J. Am. Chem. Soc.*, 85: 2149–2154 (1963). In vitro protein synthesis may be performed using manual techniques or by automation. Automated synthesis may be accomplished, for instance, with an Applied Biosystems Peptide Synthesizer (Foster City, Calif.) using manufacturer's instructions. Various portions of the PRO256 polypeptide may be chemically synthesized separately and combined using chemical or enzymatic methods to produce the full-length PRO256 polypeptide.

i. Isolation of DNA Encoding PRO256 Polypeptides

DNA encoding the PRO256 polypeptide may be obtained from a cDNA library prepared from tissue believed to possess the mRNA encoding the PRO256 polypeptide and to express it at a detectable level. Accordingly, DNAs encoding the human PRO256 polypeptide can be conveniently obtained from cDNA libraries prepared from human tissues, such as described in the Examples. The gene encoding the PRO256 polypeptide may also be obtained from a genomic library or by oligonucleotide synthesis.

Libraries can be screened with probes (such as antibodies to the PRO256 polypeptide or oligonucleotides of at least about 20–80 bases) designed to identify the gene of interest or the protein encoded by it. Screening the cDNA or genomic library with the selected probe may be conducted using standard procedures, such as described in Sambrook et al., supra. An alternative means to isolate the gene encoding the PRO256 polypeptide is to use PCR methodology. Sambrook et al., supra; Dieffenbach et al., *PCR Primer: A Laboratory Manual* (New York: Cold Spring Harbor Laboratory Press, 1995).

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation, or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INHERIT, which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

ii. Selection and Transformation of Host Cells

Host cells are transfected or transformed with expression or cloning vectors described herein for PRO256 polypeptide production and cultured in conventional nutrient media modified as appropriate for inducing promoters, selecting transformants, or amplifying the genes encoding the desired sequences. The culture conditions, such as media, temperature, pH, and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of transfection are known to the ordinarily skilled artisan, for example, $CaPO_4$ treatment and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with Agrobacterium tumefaciens is used for transformation of certain plant cells, as described by Shaw et al., *Gene*, 23: 315 (1983) and WO 89/05859 published Jun. 29, 1989. For mammalian cells without such cell walls, the calcium phosphate precipitation method of Graham and van der Eb, *Virology*, 52: 456–457 (1978) can be employed. General aspects of mammalian cell host system transformations have been described in U.S. Pat. No. 4,399,216. Transformations into yeast are typically carried out according to the method of Van Solingen et al., *J. Bact.*, 130: 946 (1977) and Hsiao et al., *Proc. Natl. Acad. Sci.* (*USA*), 76: 3829 (1979). However, other methods for introducing DNA into cells, such as by nuclear microinjection, electroporation, bacterial protoplast fusion with intact cells, or polycations, e.g., polybrene or polyornithine, may also be used. For various techniques for transforming mammalian cells, see, Keown et al., *Methods in Enzymology*, 185: 527–537 (1990) and Mansour et al., *Nature*, 336: 348–352 (1988).

Suitable host cells for cloning or expressing the DNA in the vectors herein include prokaryote, yeast, or higher eukaryote cells. Suitable prokaryotes include, but are not limited to, eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325); and K5 772 (ATCC 53,635). Other suitable prokaryotic host cells include Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W31 10 may be modified to effect a genetic mutation in the genes encoding proteins endogenous to the host, with examples of such hosts including *E. coli* W3110 strain 1A2, which has the complete genotype tonA ; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6with a non-kanamycin resistent degP deletion mutation; and *E. Coli* W3110 strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for vectors encoding the PRO256 polypeptide. *Saccharomyces cerevisiae* is a commonly used lower eukaryotic host microorganism. Others include *Schizosaccharomyces pombe* (Beach and Nurse, *Nature*, 290: 140 [1981]; EP 139,383 published May 2, 1985); Kluyveromyces hosts (U.S. Pat. No. 4,943,529;Fleer et al., *Bio/Technology*, 9: 968–975 (1991)) such as, e.g., *K. lactis* (MW98–8C, CBS683,CBS4574; Louvencourt et al., *J. Bacteriol.*, 737 [1983 ]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8: 135 (1990)), *K. thermotolerans*, and *K. marxianus; yarrowia* (EP402,226); *Pichia pastoris* (EP 183,070; Sreekrishna et al.,*J. Basic Microbiol.*, 28: 265–278 [1988 ]); Candida; *Trichoderma reesia* (EP 244,234); *Neurospora crassa* (Case et al., *Proc. Natl. Acad. Sci. USA*, 76:5259–5263 [1979 ]); Schwanniomyces such as *Schwanniomyces occidentalis* (EP 394,538 published October 31, 1990); and filamentous fungi such as, e.g., Neurospora, Penicillium, Tolypocladium (WO 91/00357 published Jan. 10, 1991), and Aspergillus hosts such as *A. nidulans* (Ballance et al., *Biochem. Biophys. Res. Commun.*, 112: 284–289 [1983]; Tilburn et al., *Gene*, 26: 205–221 [1983]; Yelton et al., *Proc. Natl. Acad. Sci. USA*, 81: 1470–1474 [1984]) and *A. niger* (Kelly and Hynes, *EMBO J.*, 4: 475–479 [1985]). Methylotropic yeasts are suitable herein and include, but are not limited to, yeast capable of growth on methanol selected from the genera consisting of Hansenula, Candida, Kloeckera, Pichia, Saccharomyces, Torulopsis, and Rhodotorula. A list of specific species that are exemplary of this class of yeasts may be found in C. Anthony, *The Biochemistry of Methylotrophs*, 269 (1982).

Suitable host cells for the expression of nucleic acid encoding glycosylated PRO256 polypeptides are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen. Virol.*, 36: 59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); human lung cells (W138, ATCC CCL 75); human liver cells (Hep G2,HB 8065); and mouse mammary tumor (MMT 060562, ATCC CCL51). The selection of the appropriate host cell is deemed to be within the skill in the art.

iii. Selection and Use of a Replicable Vector

The nucleic acid (e.g., cDNA or genomic DNA) encoding the PRO256 polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence if the sequence is to be secreted, an origin of replication, one or more marker genes, an enhancer element, a promoter, and a transcription termination sequence. Construction of suitable vectors containing one or more of these components employs standard ligation techniques that are known to the skilled artisan.

The PRO256 polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the DNA encoding the PRO256 polypeptide that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV, or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the nucleic acid encoding the PRO256 polypeptide such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA* 77: 4216 (1980). A suitable selection gene for use in yeast is the trp1 gene present in the yeast plasmid YRp7. Stinchcomb et al., *Nature*, 282: 39 (1979); Kingsman et al., *Gene*, 7: 141 (1979); Tschemper et al., *Gene*, 10: 157 (1980).

The trp1 gene provides a selection marker for a mutant strain of yeast lacking the ability to grow in tryptophan, for example, ATCC No. 44076 or PEP4–1. Jones, *Genetics*, 85: 12 (1977).

Expression and cloning vectors usually contain a promoter operably linked to the nucleic acid sequence encoding the PRO256 polypeptide to direct mRNA synthesis. Promoters recognized by a variety of potential host cells are well known. Promoters suitable for use with prokaryotic hosts include the β-lactamase and lactose promoter systems (Chang et al., *Nature* 275: 615 (1978); Goeddel et al., *Nature*, 281: 544 (1979)), alkaline phosphatase, a tryptophan (trp) promoter system (Goeddel, *Nucleic Acids Res.*, 8: 4057 (1980); EP 36,776), and hybrid promoters such as the tac promoter (deBoer et al., *Proc. Natl. Acad. Sci. USA,* 80: 21–25 (1983)). promoters for use in bacterial systems also will contain a Shine-Dalgarno (S.D.) sequence operably linked to the DNA encoding the PRO256 polypeptide.

Examples of suitable promoting sequences for use with yeast hosts include the promoters for 3-phosphoglycerate kinase (Hitzeman et al., *J. Biol. Chem.*, 255: 2073 (1980)) or other glycolytic enzymes (Hess et al., *J. Adv. Enzyme Reg.*, 7: 149 (1968); Holland, *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters that are inducible promoters having the additional advantage of transcription controlled by growth conditions are the promoter regions for alcohol dehydrogenase 2, isocytochrome C, acid phosphatase, degradative enzymes associated with nitrogen metabolism, met allothionein, glyceraldehyde-3-phosphate dehydrogenase, and enzymes responsible for maltose and galactose utilization. Suitable vectors and promoters for use in yeast expression are further described in EP 73,657.

PRO256 nucleic acid transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus, and Simian Virus 40 (SV40); by heterologous mammalian promoters, e.g., the actin promoter or an immunoglobulin promoter; and by heat-shock promoters, provided such promoters are compatible with the host cell systems.

Transcription of a DNA encoding the PRO256 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the sequence coding for PRO256 polypeptides, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the PRO256 polypeptide.

Still other methods, vectors, and host cells suitable for adaptation to the synthesis of the PRO256 polypeptide in recombinant vertebrate cell culture are described in Gething et al., Nature 293:620–625 (1981); Mantei et al., Nature, 281: 40–46 (1979); EP 117,060; and EP 1 17,058.

iv. Detecting Gene Amplification/Expression

Gene amplification and/or expression may be measured in a sample directly, for example, by conventional Southern blotting, Northern blotting to quantitate the transcription of mRNA (Thomas, Proc. Natl. Acad. Sci. USA, 77:5201–5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native-sequence PRO256 polypeptide or against a synthetic peptide based on the DNA sequences provided herein or against exogenous sequence fused to DNA encoding the PRO256 polypeptide and encoding a specific antibody epitope.

v. Purification of PRO256 Polypeptides

Forms of PRO256 polypeptides may be recovered from culture medium or from host cell lysates. If membrane-bound, it can be released from the membrane using a suitable detergent solution (e.g., TRITON-X™ 100) or by enzymatic cleavage. Cells employed in expression of nucleic acid encoding the PRO256 polypeptide can be disrupted by various physical or chemical means, such as freeze-thaw cycling, sonication, mechanical disruption, or cell-lysing agents. It may be desired to purify the PRO256 polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; Protein A Sepharose columns to remove contaminants such as IgG; and met al chelating columns to bind epitope-tagged forms of the PRO256 polypeptide. Various methods of protein purification may be employed and such methods are known in the art and described, for example, in Deutscher, Methods in Enzymology,182 (1990); Scopes, Protein Purification: Principles and Practice (Springer-Verlag: New York, 1982). The purification step(s) selected will depend, for example, on the nature of the production process used and the particular PRO256 polypeptide produced.

D. Uses of PRO256 Polypeptides i. Assays for Cardiovascular, Endothelial, and Angiogenic Activity Various assays can be used to test the polypeptide herein for cardiovascular, endothelial, and angiogenic activity. Such assays include those provided in the Examples below.

Assays for testing for endothelin antagonist activity, as disclosed in U.S. Pat. No. 5,773,414, include a rat heart ventricle binding assay where the polypeptide is tested for its ability to inhibit iodinized endothelin-1 binding in a receptor assay, an endothelin receptor binding assay testing for intact cell binding of radiolabeled endothelin-1 using rabbit renal artery vascular smooth muscle cells, an inositol phosphate accumulation assay where functional activity is determined in Rat-I cells by measuring intra-cellular levels of second messengers, an arachidonic acid release assay that measures the ability of added compounds to reduce endothelin-stimulated arachidonic acid release in cultured vascular smooth muscles, in vitro (isolated vessel) studies using endothelium from male New Zealand rabbits, and in vivo studies using male Sprague-Dawley rats.

Assays for tissue generation activity include, without limitation, those described in WO 95/16035 (bone, cartilage, tendon); WO 95/05846 (nerve, neuronal), and WO 91/07491 (skin, endothelium).

Assays for wound-healing activity include, for example, those described in Winter, Epidermal Wound Healing, Maibach, H I and Rovee, D T, eds. (Year Book Medical Publishers, Inc., Chicago)(1972), pp. 71–112, as modified by the article of Eaglstein and Mertz, J. Invest. Dermatol., 71: 382–384 (1978).

An assay to screen for a test molecule relating to a PRO256 polypeptide that binds an endothelin $B_1$. ($ETB_1$) receptor polypeptide and modulates signal transduction activity involves providing a host cell transformed with a DNA encoding endothelin $B_1$ receptor polypeptide, exposing the cells to the test candidate, and measuring endothelin $B_1$ receptor signal transduction activity, as described, e.g., in U.S. Pat. No. 5,773,223.

There are several cardiac hypertrophy assays. In vitro assays include induction of spreading of adult rat cardiac myocytes. In this assay, ventricular myocytes are isolated from a single (male Sprague-Dawley) rat, essentially following a modification of the procedure described in detail by Piper et al., "Adult ventricular rat heart muscle cells" in Cell Culture Techniques in Heart and Vessel Research, H. M. Piper, ed. (Berlin: Springer-Verlag, 1990), pp.36–60. This procedure permits the isolation of adult ventricular myocytes and the long-term culture of these cells in the rod-shaped phenotype. Phenylephrine and prostaglandin $F_{2\alpha}$ ($PGF_{2\alpha}$) have been shown to induce a spreading response in these adult cells. The inhibition of myocyte spreading induced by $PGF_{2\alpha}$ or PGF2α analogs (e.g., fluprostenol) and phenylephrine by various potential inhibitors of cardiac hypertrophy is then tested.

One example of an in vivo assay is a test for inhibiting cardiac hypertrophy induced by fluprostenol in vivo. This pharmacological model tests the ability of the PRO256 polypeptide to inhibit cardiac hypertrophy induced in rats (e.g., male Wistar or Sprague-Dawley) by subcutaneous injection of fluprostenol (an agonist analog of $PGF_{2\alpha}$). It is known that rats with pathologic cardiac hypertrophy induced by myocardial infarction have chronically elevated levels of extractable $PGF_{2\alpha}$ in their myocardium. Lai et al., Am. J. Physiol. (Heart Circ. Physiol.), 271: H2197–H2208 (1996). Accordingly, factors that can inhibit the effects of fluprostenol on myocardial growth in vivo are potentially useful for treating cardiac hypertrophy. The effects of the PRO256 polypeptide on cardiac hypertrophy are determined by measuring the weight of heart, ventricles, and left ventricle (normalized by body weight) relative to fluprostenol-treated rats not receiving the PRO256 polypeptide.

Another example of an in vivo assay is the pressure-overload cardiac hypertrophy assay. For in vivo testing it is common to induce pressure-overload cardiac hypertrophy by constriction of the abdominal aorta of test animals. In a typical protocol, rats (e.g., male Wistar or Sprague-Dawley) are treated under anesthesia, and the abdominal aorta of each rat is narrowed down just below the diaphragm. Beznak M., Can. J. Biochem. Physiol., 33: 985–94 (1955). The aorta is exposed through a surgical incision, and a blunted needle is placed next to the vessel. The aorta is constricted with a ligature of silk thread around the needle, which is immediately removed and which reduces the lumen of the aorta to the diameter of the needle. This approach is described, for example, in Rossi et al., Am. Heart J. 124: 700–709 (1992) and O'Rourke and Reibel, P.S.E.M.B. 200: 95–100 (1992).

In yet another in vivo assay, the effect on cardiac hypertrophy following experimentally induced myocardial infarction (MI) is measured. Acute MI is induced in rats by left coronary artery ligation and confirmed by electrocardiographic examination. A sham-operated group of animals is also prepared as control animals. Earlier data have shown that cardiac hypertrophy is present in the group of animals with MI, as evidenced by an 18% increase in heart weight-to-body weight ratio. Lai et al., supra. Treatment of these animals with candidate blockers of cardiac hypertrophy, e.g., the PRO256 polypeptide, provides valuable information about the therapeutic potential of the candidates tested. One further such assay test for induction of cardiac hypertrophy is disclosed in U.S. Pat. No. 5,773,415, using Sprague-Dawley rats.

For cancer, a variety of well-known animal models can be used to further understand the role of the genes identified herein in the development and pathogenesis of tumors, and to test the efficacy of candidate therapeutic agents, including antibodies and other agonists of native PRO256 polypeptides. The in vivo nature of such models makes them particularly predictive of responses in human patients. Animal models of tumors and cancers (e.g., breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumor cells into syngeneic mice using standard techniques, e.g., subcutaneous injection, tail vein injection, spleen implantation, intraperitoneal implantation, implantation under the renal capsule, or orthopin implantation, e.g., colon cancer cells implanted in colonic tissue. See, e.g., PCT publication No. WO 97/33551, published Sep. 18, 1997. Probably the most often used animal species in oncological studies are immunodeficient mice and, in particular, nude mice. The observation that the nude mouse with thymic hypo/aplasia could successfully act as a host for human tumor xenografts has lead to its widespread use for this purpose. The autosomal recessive nu gene has been introduced into a very large number of distinct congenic strains of nude mouse, including, for example, ASW, A/He, AKR, BALB/c, B 10,LP, C17, C3H, C57BL, C57, CBA, DBA, DDD, I/st, NC, NFR, NFS, NFS/N, NZB, NZC, NZW, P, RIII, and SJL. In addition, a wide variety of other animals with inherited immunological defects other than the nude mouse have been bred and used as recipients of tumor xenografts. For further details see, e.g., The Nude Mouse in Oncology Research, E. Boven and B. Winograd, eds. (CRC Press, Inc., 1991).

The cells introduced into such animals can be derived from known tumor/cancer cell lines, such as any of the above-listed tumor cell lines, and, for example, the B104-1-1 cell line (stable NIH-3T3 cell line transfected with the neu protooncogene); ras-transfected NIH-3T3 cells; Caco-2 (ATCC HTB-37); or a moderately well-differentiated grade II human colon adenocarcinoma cell line, HT-29 (ATCC HTB-38); or from tumors and cancers. Samples of tumor or cancer cells can be obtained from patients undergoing surgery, using standard conditions involving freezing and storing in liquid nitrogen. Karmali et al., Br. J. Cancer 48: 689–696 (1983).

Tumor cells can be introduced into animals such as nude mice by a variety of procedures. The subcutaneous (s.c.) space in mice is very suitable for tumor implantation. Tumors can be transplanted s.c. as solid blocks, as needle biopsies by use of a trochar, or as cell suspensions. For solid-block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue.

Animal models of breast cancer can be generated, for example, by implanting rat neuroblastoma cells (from which the neu oncogene was initially isolated), or neu-transformed NIH-3T3 cells into nude mice, essentially as described by Drebin et al. Proc. Nat. Acad. Sci. USA, 83: 9129–9133 (1986).

Similarly, animal models of colon cancer can be generated by passaging colon cancer cells in animals, e.g., nude mice, leading to the appearance of tumors in these animals. An orthotopic transplant model of human colon cancer in nude mice has been described, for example, by Wang et al., Cancer Research, 54: 4726–4728 (1994) and Togo et al., Cancer Research, 55: 681–684 (1995). This model is based on the so-called "METAMOUSE™" sold by AntiCancer, Inc., (San Diego, Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines.

For example, Meth A, CMS4, CMS5, CMS21, and WEHI-164 are chemically induced fibrosarcomas of BALB/c female mice (DeLeo et al., J. Exp. Med., 146: 720 (1977)), which provide a highly controllable model system for studying the anti-tumor activities of various agents. Palladino et al., J. Immunol., 138: 4023–4032 (1987). Briefly, tumor cells are propagated in vitro in cell culture. Prior to injection into the animals, the cell lines are washed and suspended in buffer, at a cell density of about $10 \times 10^6$ to $10 \times 10^7$ cells/ml. The animals are then infected subcutaneously with 10 to 100 µl of the cell suspension, allowing one to three weeks for a tumor to appear.

In addition, the Lewis lung (3LL) carcinoma of mice, which is one of the most thoroughly studied experimental tumors, can he used as an investigational tumor model. Efficacy in this tumor model has been correlated with beneficial effects in the treatment of human patients diagnosed with small-cell carcinoma of the lung (SCCL). This tumor can be introduced in normal mice upon injection of tumor fragments from an affected mouse or of cells maintained in culture. Quivey et al., *Br. J. Cancer,* 41: suppl. 4, 30 (1980). Evidence indicates that tumors can be started from injection of even a single cell and that a very high proportion of infected tumor cells survive. For further information about this tumor model see, Zacharski, *Haemostasis,* 16: 300–320 (1986).

One way of evaluating the efficacy of a test compound in an animal model with an implanted tumor is to measure the size of the tumor before and after treatment. Traditionally, the size of implanted tumors has been measured with a slide caliper in two or three dimensions. The measure limited to two dimensions does not accurately reflect the size of the tumor; therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, *Proc. 6th Int. Workshop on Immune-Deficient Animals,* Wu and Sheng eds. (Basel, 1989), p.301. It is noted, however, that necrosis and inflammatory responses following treatment may actually result in an increase in tumor size, at least initially. Therefore, these changes need to be carefully monitored, by a combination of a morphometric method and flow cytometric analysis.

Further, recombinant (transgenic) animal models can be engineered by introducing the coding portion of the PRO256 gene identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. Techniques known in the art to introduce a transgene into such animals include pronucleic microinjection (U.S. Pat. No. 4,873,191); retrovirus-mediated gene transfer into germ lines (e.g., Van der Putten et al., *Proc. Natl. Acad. Sci. USA,* 82: 6148–6152 (1985)); gene targeting in embryonic stem cells (Thompson et al., *Cell,* 56: 313–321 (1989)); electroporation of embryos (Lo, Mol. Cell. Biol., 3: 1803–1814 (1983)); and sperm-mediated gene transfer. Lavitrano et al., *Cell,* 57: 717–723 (1989). For a review, see for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA,* 89: 6232–6236 (1992). The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals are further examined for signs of tumor or cancer development.

Alternatively, "knock-out" animals can be constructed that have a defective or altered gene encoding a PRO256 polypeptide identified herein, as a result of homologous recombination between the endogenous gene encoding the PRO256 polypeptide and altered genomic DNA encoding the same polypeptide introduced into an embryonic cell of the animal. For example, cDNA encoding a particular PRO256 polypeptide can be used to clone genomic DNA encoding that polypeptide in accordance with established techniques. A portion of the genomic DNA encoding a particular PRO256 polypeptide can be deleted or replaced with another gene, such as a gene encoding a selectable marker that can be used to monitor integration. Typically, several kilobases of unaltered flanking DNA (both at the 5' and 3' ends) are included in the vector. See, e.g., Thomas and Capecchi, *Cell,* 51: 503 (1987) for a description of homologous recombination vectors. The vector is introduced into an embryonic stem cell line (e.g., by electroporation) and cells in which the introduced DNA has homologously recombined with the endogenous DNA are selected. See, e.g., Li et al., *Cell,* 69:915 (1992). The selected cells are then injected into a blastocyst of an animal (e.g., a mouse or rat) to form aggregation chimeras. See, e.g., Bradley, in *Teratocarcinomas and Embryonic Stem Cells: A Practical Approach,* E. J. Robertson, ed. (IRL: Oxford, 1987), pp. 113–152. A chimeric embryo can then be implanted into a suitable pseudopregnant female foster animal and the embryo brought to term to create a "knock-out" animal. Progeny harboring the homologously recombined DNA in their germ cells can be identified by standard techniques and used to breed animals in which all cells of the animal contain the homologously recombined DNA. Knockout animals can be characterized, for instance, by their ability to defend against certain pathological conditions and by their development of pathological conditions due to absence of the PRO256 polypeptide.

The efficacy of antibodies specifically binding the PRO256 polypeptides identified herein, and other drug candidates, can be tested also in the treatment of spontaneous animal tumors. A suitable target for such studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis may merely be a reflection of the short survival times for cats with this tumor. These tumors are usually not amenable to surgery, primarily because of the anatomy of the feline oral cavity. At present, there is no effective treatment for this tumor. Prior to entry into the study, each cat undergoes complete clinical examination and biopsy, and is scanned by computed tomography (CT). Cats diagnosed with sublingual oral squamous cell tumors are excluded from the study. The tongue can become paralyzed as a result of such tumor, and even if the treatment kills the tumor, the animals may not be able to feed themselves. Each cat is treated repeatedly, over a longer period of time. Photographs of the tumors will be taken daily during the treatment period, and at each subsequent recheck. After treatment, each cat undergoes another CT scan. CT scans and thoracic radiograms are evaluated every 8 weeks thereafter. The data are evaluated for differences in survival, response, and toxicity as compared to control groups. Positive response may require evidence of tumor regression, preferably with improvement of quality of life and/or increased life span.

In addition, other spontaneous animal tumors, such as fibrosarcoma, adenocarcinoma, lymphoma, chondroma, or leiomyosarcoma of dogs, cats, and baboons can also be tested. Of these, mammary adenocarcinoma in dogs and cats is a preferred model as its appearance and behavior are very similar to those in humans. However, the use of this model is limited by the rare occurrence of this type of tumor in animals.

Other in vitro and in vivo cardiovascular, endothelial, and angiogenic tests known in the art are also suitable herein.

ii. Tissue Distribution

The results of the cardiovascular, endothelial, and angiogenic assays herein can be verified by further studies, such as by determining mRNA expression in various human tissues.

As noted before, gene amplification and/or gene expression in various tissues may be measured by conventional Southern blotting, Northern blotting to quantitate the transcription of mRNA (Thomas, *Proc. Natl. Acad. Sci. USA* 77:5201–5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native-sequence PRO256 polypeptide or against a synthetic peptide based on the DNA sequences provided herein or against exogenous sequence fused to PRO256 DNA and encoding a specific antibody epitope. General techniques for generating antibodies, and special protocols for in situ hybridization are provided hereinbelow.

iii. Antibody Binding Studies

The results of the cardiovascular, endothelial, and angiogenic study can be further verified by antibody binding studies, in which the ability of anti-PRO256 antibodies to inhibit the effect of the PRO256 polypeptides on endothelial cells or other cells used in the cardiovascular, endothelial, and angiogenic assays is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. Zola, *Monoclonal Antibodies: A Manual of Techniques* (CRC Press, Inc., 1987), pp.147–158.

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte that remain unbound.

Sandwich assays involve the use of two antibodies, each capable of binding to a different immunogenic portion, or epitope, of the protein to be detected. In a sandwich assay, the test sample analyte is bound by a first antibody that is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

iv. Cell-Based Tumor Assays

Cell-based assays and animal models for cardiovascular, endothelial, and angiogenic disorders, such as tumors, can be used to verify the findings of a cardiovascular, endothelial, and angiogenic assay herein, and further to understand the relationship between the genes identified herein and the development and pathogenesis of undesirable cardiovascular, endothelial, and angiogenic cell growth. The role of gene products identified herein in the development and pathology of undesirable cardiovascular, endothelial, and angiogenic cell growth, e.g., tumor cells, can be tested by using cells or cells lines that have been identified as being stimulated or inhibited by the PRO256 polypeptide herein. Such cells include, for example, those set forth in the Examples below.

In a different approach, cells of a cell type known to be involved in a particular cardiovascular, endothelial, and angiogenic disorder are transfected with the cDNAs herein, and the ability of these cDNAs to induce excessive growth or inhibit growth is analyzed. If the cardiovascular, endothelial, and angiogenic disorder is cancer, suitable tumor cells include, for example, stable tumor cell lines such as the B104-1-1 cell line (stable NIH-3T3 cell line transfected with the neu protooncogene) and ras-transfected NIH-3T3 cells, which can be transfected with the desired gene and monitored for tumorigenic growth. Such transfected cell lines can then be used to test the ability of poly- or monoclonal antibodies or antibody compositions to inhibit tumorigenic cell growth by exerting cytostatic or cytotoxic activity on the growth of the transformed cells, or by mediating antibody-dependent cellular cytotoxicity (ADCC). Cells transfected with the coding sequences of the genes identified herein can further be used to identify drug candidates for the treatment of cardiovascular, endothelial, and angiogenic disorders such as cancer.

In addition, primary cultures derived from tumors in transgenic animals (as described above) can be used in the cell-based assays herein, although stable cell lines are preferred. Techniques to derive continuous cell lines from transgenic animals are well known in the art. See, e.g., Small et al., *Mol. Cell. Biol.,* 5: 642–648 (1985).

v. Gene Therapy

The PRO256 polypeptides herein and polypeptidyl agonists and antagonists may be employed in accordance with the present invention by expression of such polypeptides in vivo, which is often referred to as gene therapy.

There are two major approaches to getting the nucleic acid (optionally contained in a vector) into the patient's cells: in vivo and ex vivo. For in vivo delivery the nucleic acid is injected directly into the patient, usually at the sites where the PRO256 polypeptide is required, i.e., the site of synthesis of the PRO256 polypeptide, if known, and the site (e.g., solid tumor) where biological activity of the PRO256 polypeptide is needed. For ex vivo treatment, the patient's cells are removed, the nucleic acid is introduced into these isolated cells, and the modified cells are administered to the patient either directly or, for example, encapsulated within porous membranes that are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (preferably retroviral) particle with a cellular receptor, followed by introduction of the nucleic acids contained by the particle into the cell. A commonly used vector for ex vivo delivery of the gene is a retrovirus.

The currently preferred in vivo nucleic acid transfer techniques include transfection with viral or non-viral vectors (such as adenovirus, lentivirus, Herpes simplex I virus, or adeno-associated virus (AAV)) and lipid-based systems (useful lipids for lipid-mediated transfer of the gene are, for example, DOTMA, DOPE, and DC-Chol; see, e.g., Tonkinson et al., *Cancer Investigation*, 14 (1): 54–65 (1996)). The most preferred vectors for use in gene therapy are viruses, most preferably adenoviruses, AAV, lentiviruses, or retroviruses. A viral vector such as a retroviral vector includes at least one transcriptional promoter/enhancer or locus-defining element(s), or other elements that control gene expression by other means such as alternate splicing, nuclear RNA export, or post-translational modification of messenger. In addition, a viral vector such as a retroviral vector includes a nucleic acid molecule that, when transcribed in the presence of a gene encoding the PRO256 polypeptide, is operably linked thereto and acts as a translation initiation sequence. Such vector constructs also include a packaging signal, long terminal repeats (LTRs) or portions thereof, and positive and negative strand primer binding sites appropriate to the virus used (if these are not already present in the viral vector). In addition, such vector typically includes a signal sequence for secretion of the PRO256 polypeptide from a host cell in which it is placed. Preferably the signal sequence for this purpose is a mammalian signal sequence, most preferably the native signal sequence for the PRO256 polypeptide. Optionally, the vector construct may also include a signal that directs polyadenylation, as well as one or more restriction sites and a translation termination sequence. By way of example, such vectors will typically include a 5 ' LTR, a tRNA binding site, a packaging signal, an origin of second-strand DNA synthesis, and a 3 ' LTR or a portion thereof. Other vectors can be used that are non-viral, such as cationic lipids, polylysine, and dendrimers.

In some situations, it is desirable to provide the nucleic acid source with an agent that targets the target cells, such as an antibody specific for a cell-surface membrane protein or the target cell, a ligand for a receptor on the target cell, etc. Where liposomes are employed, proteins that bind to a cell-surface membrane protein associated with endocytosis may be used for targeting and/or to facilitate uptake, e.g., capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.* 262: 4429–4432 (1987); and Wagner et al., *Proc. Natl. Acad. Sci. USA*, 87: 3410–3414 (1990). For a review of the currently known gene marking and gene therapy protocols, see, Anderson et al., *Science* 256: 808–813 (1992). See also WO 93/25673 and the references cited therein.

Suitable gene therapy and methods for making retroviral particles and structural proteins can be found in, e.g., U.S. Pat. No. 5,681,746.

vi. Use of Gene as a Diagnostic

This invention is also related to the use of the gene encoding the PRO256 polypeptide as a diagnostic. Detection of a mutated form of the PRO256 polypeptide will allow a diagnosis of a cardiovascular, endothelial, and angiogenic disease or a susceptibility to a cardiovascular, endothelial, and angiogenic disease, such as a tumor, since mutations in the PRO256 polypeptide may cause tumors.

Individuals carrying mutations in the genes encoding a human PRO256 polypeptide may be detected at the DNA level by a variety of techniques. Nucleic acids for diagnosis may be obtained from a patient's cells, such as from blood, urine, saliva, tissue biopsy, and autopsy material. The genomic DNA may be used directly for detection or may be amplified enzymatically by using PCR (Saiki et al., *Nature*, 324: 163–166 (1986)) prior to analysis. RNA or cDNA may also be used for the same purpose. As an example, PCR primers complementary to the nucleic acid encoding the PRO256 polypeptide can be used to identify and analyze the PRO256 polypeptide mutations. For example, deletions and insertions can be detected by a change in size of the amplified product in comparison to the normal genotype. Point mutations can be identified by hybridizing amplified DNA to radiolabeled RNA encoding the PRO256 polypeptide, or alternatively, radiolabeled antisense DNA sequences encoding the PRO256 polypeptide. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamidine gradient gels in which the mobilities of different DNA fragments are retarded in the gel at different positions according to their specific melting or partial melting temperatures. See, e.g., Myers et al., *Science*, 230: 1242 (1985).

Sequence changes at specific locations may also be revealed by nuclease protection assays, such as RNase and S1 protection or the chemical cleavage method, for example, Cotton et al., *Proc. Natl. Acad. Sci. USA*, 85: 4397–4401 (1985).

Thus, the detection of a specific DNA sequence may be achieved by methods such as hybridization, RNase protection, chemical cleavage, direct DNA sequencing, or the use of restriction enzymes, e.g., restriction fragment length polymorphisms (RFLP), and Southern blotting of genomic DNA.

vii. Use to Detect PRO256 Polpeptide Levels

In addition to more conventional gel-electrophoresis and DNA sequencing, mutations can also be detected by in situ analysis.

Expression of nucleic acid encoding the PRO256 polypeptide may be linked to peripheral vascular disease, hepatic or renal injury, or restenosis indications. If the PRO256 polypeptide has a signal sequence and the mRNA is highly expressed in endothelial cells and to a lesser extent in smooth muscle cells, this indicates that the PRO256 polypeptide is present in serum. Accordingly, an anti- PRO256 polypeptide antibody could be used to diagnose peripheral vascular disease, hepatic disorders or restenosis, since an altered level of this PRO256 polypeptide may be indicative of such disorders.

A competition assay may be employed wherein antibodies specific to the PRO256 polypeptide are attached to a solid support and the labeled PRO256 polypeptide and a sample derived from the host are passed over the solid support and the amount of label detected attached to the solid support can be correlated to a quantity of the PRO256 polypeptide in the sample.

viii. Chromosome Mapping

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis for the 3'-untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes, and preselection by hybridization to construct chromosome-specific cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the gene encoding the PRO256 polypeptide was derived, and the longer the better. For example, 2,000 bp is good, 4,000 bp is better, and more than 4,000 is probably not necessary to get good results a reasonable percentage of the time. For a review of this technique, see, Verma et al., *Human Chromosomes: a Manual of Basic Techniques* (Pergamon Press, New York, 1988).

Once a sequence has been mapped to a precise chromosomal location, the physical position of the sequence on the chromosome can be correlated with genetic map data. Such data are found, for example, in V. McKusick, *Mendelian Inheritance in Man* (available online through Johns Hopkins University Welch Medical Library). The relationship between genes and diseases that have been mapped to the same chromosomal region is then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

ix. Screening Assays for Drug Candidates

This invention encompasses methods of screening compounds to identify those that mimic the PRO256 polypeptide (agonists) or prevent the effect of the PRO256 polypeptide (antagonists). Screening assays for antagonist drug candidates are designed to identify compounds that bind or complex with the PRO256 polypeptide encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO256 polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO256 polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO256 polypeptide and drying. Alternatively, an immobilized antibody, e.g., a monoclonal antibody, specific for the PRO256 polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO256 polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (*London*), 340: 245–246 (1989); Chien et al., *Proc. Natl. Acad. Sci. USA,* 88: 9578–9582 (1991)) as disclosed by Chevray and Nathans, *Proc. Natl. Acad. Sci. USA* 89:5789–5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1 lacz reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO256 polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

The compositions useful in the treatment of cardiovascular, endothelial, and angiogenic disorders include, without limitation, antibodies, small organic and inorganic molecules, peptides, phosphopeptides, antisense and ribozyme molecules, triple-helix molecules, etc., that inhibit the expression and/or activity of the target gene product.

More specific examples of potential antagonists include an oligonucleotide that binds to the fusions of immunoglobulin with a PRO256 polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO256 polypeptide that recognizes the receptor but imparts no effect, thereby competitively inhibiting the action of the PRO256 polypeptide.

Another potential PRO256 polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5 ' coding portion of the polynucleotide sequence, which encodes the mature PRO256 polypeptides herein, is used to design an antisense RNA oligonucleotide of from about 10 to 40 base pairs in length. A DNA oligonucleotide is designed to be complementary to a region of the gene involved in transcription (triple helix—see, Lee et al., *Nucl. Acids Res.,* 6:3073 (1979); Cooney et al., *Science* 241: 456 (1988); Dervan et al., *Science,* 251:1360 (1991)), thereby preventing transcription and the production of the PRO256 polypeptide. The antisense RNA oligonucleotide hybridizes to the mRNA in vivo and blocks translation of the mRNA molecule into the PRO256 polypeptide (antisense—Okano, *Neurochem.,* 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO256 polypeptide. When antisense DNA is used, oligodeoxyribonucleotides derived from the translation-initiation site, e.g., between about −10 and +10 positions of the target gene nucleotide sequence, are preferred.

Antisense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

Potential antagonists include small molecules that bind to the active site, the receptor binding site, or growth factor or other relevant binding site of the PRO256 polypeptide, thereby blocking the normal biological activity of the PRO256 polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4: 469–471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

x. Types of Cardiovascular, Endothelial, and Angiogenic Disorders to be Treated

The PRO256 polypeptides, or agonists or antagonists thereto, that have activity in the cardiovascular, angiogenic, and endothelial assays described herein, and/or whose gene product has been found to be localized to the cardiovascular system, are likely to have therapeutic uses in a variety of cardiovascular, endothelial, and angiogenic disorders, including systemic disorders that affect vessels, such as diabetes mellitus. Their therapeutic utility could include diseases of the arteries, capillaries, veins, and/or lymphatics. Examples of treatments hereunder include treating muscle wasting disease, treating osteoporosis, aiding in implant fixation to stimulate the growth of cells around the implant and therefore facilitate its attachment to its intended site, increasing IGF stability in tissues or in serum, if applicable, and increasing binding to the IGF receptor (since IGF has been shown in vitro to enhance human marrow erythroid and granulocytic progenitor cell growth).

The PRO256 polypeptides or agonists or antagonists thereto may also be employed to stimulate erythropoiesis or granulopoiesis, to stimulate wound healing or tissue regeneration and associated therapies concerned with re-growth of tissue, such as connective tissue, skin, bone, cartilage, muscle, lung, or kidney, to promote angiogenesis, to stimulate or inhibit migration of endothelial cells, and to proliferate the growth of vascular smooth muscle and endothelial cell production. The increase in angiogenesis mediated by an antagonist of the PRO256 polypeptide would be beneficial to ischemic tissues and to collateral coronary development in the heart subsequent to coronary stenosis. PRO256 polypeptides or agonists thereof are used to inhibit angiogenesis, for example, to limit the production of excess connective tissue during wound healing or pulmonary fibrosis.

The decision of whether to use the molecule itself or an agonist thereof for any particular indication, as opposed to an antagonist to the molecule, would depend mainly on whether the molecule herein promotes cardiovascularization, genesis of endothelial cells, or angiogenesis or inhibits these conditions. For example, PRO256 polypeptides or an agonist thereof, can be shown to inhibit the activation of hepatocyte growth factor and thus also would inhibit the promotion of angiogenesis. Thus, it would be expected to be useful for treatment of disorders where it is desired to limit or prevent angiogenesis. PRO256 polypeptides or agonists thereto could be used directly for treatment of disorders associated with vascular tumors such as haemangioma, tumor angiogenesis, neovascularization in the retina, choroid, or cornea, associated with diabetic retinopathy or premature infant retinopathy or macular degeneration and proliferative vitreoretinopathy, rheumatoid arthritis, Crohn's disease, atherosclerosis, ovarian hyperstimulation, psoriasis, endometriosis associated with neovascularization, restenosis subsequent to balloon angioplasty, scar tissue overproduction, for example, that seen in a keloid that forms after surgery, fibrosis after myocardial infarction, or fibrotic lesions associated with pulmonary fibrosis.

Antagonists of PRO256 polypeptides on the other hand, would be expected to be useful for conditions where promotion of angiogenesis is desired such as peripheral vascular disease, hypertension, inflammatory vasculitides, Reynaud's disease and Reynaud's phenomenon, aneurysms, arterial restenosis, thrombophlebitis, lymphangitis, lymphedema, wound healing and tissue repair (especially hepatic and renal tissues), ischemia reperfusion injury, angina, myocardial infarctions such as acute myocardial infarctions, chronic heart conditions, heart failure such as congestive heart failure, and osteoporosis.

Specific types of diseases are described below, where the PRO256 polypeptide herein or agonists or antagonists thereof may serve as useful for vascular-related drug targeting or as therapeutic targets for the treatment or prevention of the disorders. Atherosclerosis is a disease characterized by accumulation of plaques of intimal thickening in arteries, due to accumulation of lipids, proliferation of smooth muscle cells, and formation of fibrous tissue within the arterial wall. The disease can affect large, medium, and small arteries in any organ. Changes in endothelial and vascular smooth muscle cell function are known to play an important role in modulating the accumulation and regression of these plaques.

Hypertension is characterized by raised vascular pressure in the systemic arterial, pulmonary arterial, or portal venous systems. Elevated pressure may result from or result in impaired endothelial function and/or vascular disease.

Inflammatory vasculitides include giant cell arteritis, Takayasu's arteritis, polyarteritis nodosa (including the microangiopathic form), Kawasaki's disease, microscopic polyangiitis, Wegener's granulomatosis, and a variety of infectious-related vascular disorders (including Henoch-Schonlein prupura). Altered endothelial cell function has been shown to be important in these diseases.

Reynaud's disease and Reynaud's phenomenon are characterized by intermittent abnormal impairment of the circulation through the extremities on exposure to cold. Altered endothelial cell function has been shown to be important in this disease.

Aneurysms are saccular or fusiform dilatations of the arterial or venous tree that are associated with altered endothelial cell and/or vascular smooth muscle cells.

Arterial restenosis (restenosis of the arterial wall) may occur following angioplasty as a result of alteration in the function and proliferation of endothelial and vascular smooth muscle cells.

Thrombophlebitis and lymphangitis are inflammatory disorders of veins and lymphatics, respectively, that may result from, and/or in, altered endothelial cell function. Similarly, lymphedema is a condition involving impaired lymphatic vessels resulting from endothelial cell function.

The family of benign and malignant vascular tumors are characterized by abnormal proliferation and growth of cellular elements of the vascular system. For example, lymphangiomas are benign tumors of the lymphatic system that are congenital, often cystic, malformations of the lymphatics that usually occur in newborns. Cystic tumors tend to grow into the adjacent tissue. Cystic tumors usually occur in the cervical and axillary region. They can also occur in the soft tissue of the extremities. The main symptoms are dilated, sometimes reticular, structured lymphatics and lymphocysts surrounded by connective tissue. Lymphangiomas are assumed to be caused by improperly connected embryonic lymphatics or their deficiency. The result is impaired local lymph drainage. Griener et al., *Lymphology*, 4: 140–144 (1971).

As indicated earlier, PRO256 polypeptides or agonists thereof, would be useful in the prevention of tumor angiogenesis, a process which involves vascularization of a tumor to enable it to growth and/or metastasize. This process is dependent on the growth of new blood vessels. Examples of neoplasms and related conditions that involve tumor angiogenesis include breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), and Meigs' syndrome.

Age-related macular degeneration (AMD) is a leading cause of severe visual loss in the elderly population. The exudative form of AMD is characterized by choroidal neovascularization and retinal pigment epithelial cell detachment. Because choroidal neovascularization is associated with a dramatic worsening in prognosis, the PRO256 polypeptide or agonist thereto is expected to be useful in reducing the severity of AMD.

Healing of trauma such as wound healing and tissue repair is also a targeted use for antagonists of PRO256 polypeptides. Formation and regression of new blood vessels is essential for tissue healing and repair. This category includes bone, cartilage, tendon, ligament, and/or nerve tissue growth or regeneration, as well as wound healing and tissue repair and replacement, and in the treatment of burns, incisions, and ulcers. A PRO256 polypeptide antagonist that induces cartilage and/or bone growth in circumstances where bone is not normally formed has application in the healing of bone fractures and cartilage damage or defects in humans and other animals. Such a preparation employing a PRO256 polypeptide antagonist may have prophylactic use in closed as well as open fracture reduction and also in the improved fixation of artificial joints. De nova bone formation induced by an osteogenic agent contributes to the repair of congenital, trauma-induced, or oncologic, resection-induced craniofacial defects, and also is useful in cosmetic plastic surgery.

PRO256 polypeptide antagonists may also be useful to promote better or faster closure of non-healing wounds, including without limitation pressure ulcers, ulcers associated with vascular insufficiency, surgical and traumatic wounds, and the like.

It is expected that a PRO256 polypeptide antagonist may also exhibit activity for generation or regeneration of other tissues, such as organs (including, for example, pancreas, liver, intestine, kidney, skin, or endothelium), muscle (smooth, skeletal, or cardiac), and vascular (including vascular endothelium) tissue, or for promoting the growth of cells comprising such tissues. Part of the desired effects may be by inhibition or modulation of fibrotic scarring to allow normal tissue to regenerate.

A PRO256 antagonist may also be useful for gut protection or regeneration and treatment of lung or liver fibrosis, reperfusion injury in various tissues, and conditions resulting from systemic cytokine damage. Also, the PRO256 polypeptide or agonist or antagonist thereto may be useful for promoting or inhibiting differentiation of tissues described above from precursor tissues or cells, or for inhibiting the growth of tissues described above.

A PRO256 polypeptide antagonist may also be used in the treatment of periodontal diseases and in other tooth-repair processes. Such agents may provide an environment to attract bone-forming cells, stimulate growth of bone-forming cells, or induce differentiation of progenitors of bone-forming cells. A PRO256 polypeptide antagonist may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes, since blood vessels play an important role in the regulation of bone turnover and growth.

Another category of tissue regeneration activity that may be attributable to the PRO256 polypeptide antagonist is tendon/ligament formation. A protein that induces tendon/ligament-like tissue or other tissue formation in circumstances where such tissue is not normally formed has application in the healing of tendon or ligament tears, deformities, and other tendon or ligament defects in humans and other animals. Such a preparation may have prophylactic use in preventing damage to tendon or ligament tissue, as well as use in the improved fixation of tendon or ligament to bone or other tissues, and in repairing defects to tendon or ligament tissue. De nova tendon/ligament-like tissue formation induced by a composition of the PRO256 polypeptide antagonist contributes to the repair of congenital, trauma-induced, or other tendon or ligament defects of other origin, and is also useful in cosmetic plastic surgery for attachment or repair of tendons or ligaments. The compositions herein may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions herein may also be useful in the treatment of tendinitis, carpal tunnel syndrome, and other tendon or ligament defects. The compositions may also include an appropriate matrix and/or sequestering agent as a carrier as is well known in the art.

The PRO256 polypeptide antagonist may also be useful for proliferation of neural cells and for regeneration of nerve and brain tissue, i.e., for the treatment of central and peripheral nervous system disease and neuropathies, as well as mechanical and traumatic disorders, that involve degeneration, death, or trauma to neural cells or nerve tissue. More specifically, a PRO256 polypeptide antagonist may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions that may be treated in accordance with the present invention include mechanical and traumatic disorders, such as spinal cord disorders, head trauma, and cerebrovascular diseases such as stroke. Peripheral neuropathies resulting from chemotherapy or other medical therapies may also be treatable using a PRO256 polypeptide antagonist.

Ischemia-reperfusion injury is another indication. Endothelial cell dysfunction may be important in both the initiation of, and in regulation of the sequelae of events that occur following ischemia-reperfusion injury.

Rheumatoid arthritis is a further indication. Blood vessel growth and targeting of inflammatory cells through the vasculature is an important component in the pathogenesis of rheumatoid and sero-negative forms of arthritis.

A PRO256 polypeptide antagonist may also be useful in the management of atrial fibrillation, which develops in a substantial portion of patients diagnosed with hypertrophic cardiomyopathy.

Further indications include angina, myocardial infarctions such as acute myocardial infarctions, and heart failure such as congestive heart failure. Additional non-neoplastic conditions include psoriasis, diabetic and other proliferative retinopathies including retinopathy of prematurity, retrolental fibroplasia, neovascular glaucoma, thyroid hyperplasias (including Grave's disease), corneal and other tissue transplantation, chronic inflammation, lung inflammation, nephrotic syndrome, preeclampsia, ascites, pericardial effusion (such as that associated with pericarditis), and pleural effusion.

In view of the above, the PRO256 polypeptides or agonists or antagonists thereof described herein, which are shown to alter or impact endothelial cell function, proliferation, and/or form, are likely to play an important role in the etiology and pathogenesis of many or all of the disorders noted above, and as such can serve as therapeutic targets to augment or inhibit these processes or for vascular-related drug targeting in these disorders.

xi. Administration Protocols. Schedules, Doses, and Formulations

The molecules herein and agonists and antagonists thereto are pharmaceutically useful as a prophylactic and therapeutic agent for various disorders and diseases as set forth above.

Therapeutic compositions of the PRO256 polypeptides or agonists or antagonists are prepared for storage by mixing the desired molecule having the appropriate degree of purity with optional pharmaceutically acceptable carriers, excipients, or stabilizers (*Remington's Pharmaceutical Sciences*, 16th edition, Osol, A. ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; met al complexes (e.g., Zn-protein complexes); and/or non-ionic surfactants such as TWEEN™, PLURONICS™ or polyethylene glycol (PEG).

Additional examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of agonist or antagonist include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nanocapsules, liposomes, plasters, inhalation forms, nose sprays, sublingual tablets, and sustained-release preparations. The PRO256 polypeptides or agonists or antagonists will typically be formulated in such vehicles at a concentration of about 0.1 mg/ml to 100 mg/ml.

Another formulation comprises incorporating a PRO256 polypeptide or agonist or antagonist thereof into formed articles. Such articles can be used in modulating endothelial cell growth and angiogenesis. In addition, tumor invasion and metastasis may be modulated with these articles.

PRO256 polypeptides or agonists or antagonists to be used for in vivo administration must be sterile. This is readily accomplished by filtration through sterile filtration membranes, prior to or following lyophilization and reconstitution. PRO256 polypeptides ordinarily will be stored in lyophilized form or in solution if administered systemically. If in lyophilized form, the PRO256 polypeptide or agonist or antagonist thereto is typically formulated in combination with other ingredients for reconstitution with an appropriate diluent at the time for use. An example of a liquid formulation of a PRO256 polypeptide or agonist or antagonist is a sterile, clear, colorless unpreserved solution filled in a single-dose vial for subcutaneous injection. Preserved pharmaceutical compositions suitable for repeated use may contain, for example, depending mainly on the indication and type of polypeptide:

a) PRO256 polypeptide or agonist or antagonist thereto;

b) a buffer capable of maintaining the pH in a range of maximum stability of the polypeptide or other molecule in solution, preferably about 4–8;

c) a detergent/surfactant primarily to stabilize the polypeptide or molecule against agitation-induced aggregation;

d) an isotonifier;

e) a preservative selected from the group of phenol, benzyl alcohol and a benzethonium halide, e.g., chloride; and f) water.

If the detergent employed is non-ionic, it may, for example, be polysorbates (e.g., POLYSORBATE™ (TWEEN™) 20, 80, etc.) or poloxamers (e.g., POLOXAMER™ 188). The use of non-ionic surfactants permits the formulation to be exposed to shear surface stresses without causing denaturation of the polypeptide. Further, such surfactant-containing formulations may be employed in aerosol devices such as those used in a pulmonary dosing, and needleless jet injector guns (see, e.g., EP 257,956).

An isotonifier may be present to ensure isotonicity of a liquid composition of the PRO256 polypeptide or agonist or antagonist thereto, and includes polyhydric sugar alcohols, preferably trihydric or higher sugar alcohols, such as glycerin, erythritol, arabitol, xylitol, sorbitol, and mannitol. These sugar alcohols can be used alone or in combination. Alternatively, sodium chloride or other appropriate inorganic salts may be used to render the solutions isotonic.

The buffer may, for example, be an acetate, citrate, succinate, or phosphate buffer depending on the pH desired. The pH of one type of liquid formulation of this invention is buffered in the range of about 4 to 8, preferably about physiological pH.

The preservatives phenol, benzyl alcohol and benzethonium halides, e.g., chloride, are known antimicrobial agents that may be employed.

Therapeutic PRO256 polypeptide compositions generally are placed into a container having a sterile access port, for example, an intravenous solution bag or vial having a stopper pierceable by a hypodermic injection needle. The formulations are preferably administered as repeated intravenous (i.v.), subcutaneous (s.c.), or intramuscular (i.m.) injections, or as aerosol formulations suitable for intranasal or intrapulmonary delivery (for intrapulmonary delivery see, e.g., EP 257,956).

PRO256 polypeptides can also be administered in the form of sustained-released preparations. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.*, 15: 167–277 (1981) and Langer, *Chem. Tech.*, 12: 98–105 (1982) or poly(vinylalcohol)), polylactides (U.S. Pat. No. 3,773,919, EP 58,481), copolymers of L-glutamic acid and gamma ethyl-L-glutamate (Sidman et al., *Biopolymers*, 22: 547–556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release PRO256 polypeptide compositions also include liposomally entrapped PRO256 polypeptides. Liposomes containing the PRO256 polypeptide are prepared by methods known per se: DE 3,218,121; Epstein et al., *Proc. Natl. Acad. Sci. USA*, 82: 3688–3692 (1985); Hwang et al., *Proc. Natl. Acad. Sci. USA*, 77: 4030–4034 (1980); EP 52,322; EP 36,676; EP 88,046; EP 143,949; EP 142,641; Japanese patent application 83–118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal therapy.

The therapeutically effective dose of a PRO256 polypeptide or agonist or antagonist thereto will, of course, vary depending on such factors as the pathological condition to be treated (including prevention), the method of administration, the type of compound being used for treatment, any co-therapy involved, the patient's age, weight, general medical condition, medical history, etc., and its determination is well within the skill of a practicing physician. Accordingly, it will be necessary for the therapist to titer the dosage and modify the route of administration as required to obtain the maximal therapeutic effect. If the PRO256 polypeptide has a narrow host range, for the treatment of human patients formulations comprising human PRO256 polypeptide, more preferably native-sequence human PRO256 polypeptide, are preferred. The clinician will administer the PRO256 polypeptide until a dosage is reached that achieves the desired effect for treatment of the condition in question. For example, if the objective is the treatment of CHF, the amount would be one that inhibits the progressive cardiac hypertrophy associated with this condition. The progress of this therapy is easily monitored by echo cardiography. Similarly, in patients with hypertrophic cardiomyopathy, the PRO256 polypeptide can be administered on an empirical basis.

With the above guidelines, the effective dose generally is within the range of from about 0.001 to about 1.0 mg/kg, more preferably about 0.01–1.0 mg/kg, most preferably about 0.01–0.1 mg/kg.

For non-oral use in treating human adult hypertension, it is advantageous to administer the PRO256 polypeptide in the form of an injection at about 0.01 to 50 mg, preferably about 0.05 to 20 mg, most preferably 1 to 20 mg, per kg body weight, 1 to 3 times daily by intravenous injection. For oral administration, a molecule based on the PRO256 polypeptide is preferably administered at about 5 mg to 1 g, preferably about 10to 100 mg, per kg body weight, 1 to 3 times daily. It should be appreciated that endotoxin contamination should be kept minimally at a safe level, for example, less than 0.5 ng/mg protein. Moreover, for human administration, the formulations preferably meet sterility, pyrogenicity, general safety, and purity as required by FDA Office and Biologics standards.

The dosage regimen of a pharmaceutical composition containing the PRO256 polypeptide to be used in tissue regeneration will be determined by the attending physician considering various factors that modify the action of the polypeptides, e.g., amount of tissue weight desired to be formed, the site of damage, the condition of the damaged tissue, the size of a wound, type of damaged tissue (e.g., bone), the patient's age, sex, and diet, the severity of any infection, time of administration, and other clinical factors. The dosage may vary with the type of matrix used in the reconstitution and with inclusion of other proteins in the pharmaceutical composition. For example, the addition of other known growth factors, such as IGF-I, to the final composition may also affect the dosage. Progress can be monitored by periodic assessment of tissue/bone growth and/or repair, for example, X-rays, histomorphometric determinations, and tetracycline labeling.

The route of PRO256 polypeptide or antagonist or agonist administration is in accord with known methods, e.g., by injection or infusion by intravenous, intramuscular, intracerebral, intraperitoneal, intracerobrospinal, subcutaneous, intraocular, intraarticular, intrasynovial, intrathecal, oral, topical, or inhalation routes, or by sustained-release systems as noted below. The PRO256 polypeptide or agonists or antagonists thereof also are suitably administered by intratumoral, peritumoral, intralesional, or perilesional routes, to exert local as well as systemic therapeutic effects. The intraperitoneal route is expected to be particularly useful, for example, in the treatment of ovarian tumors.

If a peptide or small molecule is employed as an antagonist or agonist, it is preferably administered orally or non-orally in the form of a liquid or solid to mammals.

Examples of pharmacologically acceptable salts of molecules that form salts and are useful hereunder include alkali met al salts (e.g., sodium salt, potassium salt), alkaline earth met al salts (e.g., calcium salt, magnesium salt), ammonium salts, organic base salts (e.g., pyridine salt, triethylamine salt), inorganic acid salts (e.g., hydrochloride, sulfate, nitrate), and salts of organic acid (e.g., acetate, oxalate, p-toluenesulfonate).

For compositions herein that are useful for bone, cartilage, tendon, or ligament regeneration, the therapeutic method includes administering the composition topically, systemically, or locally as an implant or device. When administered, the therapeutic composition for use is in a pyrogen-free, physiologically acceptable form. Further, the composition may desirably be encapsulated or injected in a viscous form for delivery to the site of bone, cartilage, or tissue damage. Topical administration may be suitable for wound healing and tissue repair. Preferably, for bone and/or cartilage formation, the composition would include a matrix capable of delivering the protein-containing composition to the site of bone and/or cartilage damage, providing a structure for the developing bone and cartilage and preferably capable of being resorbed into the body. Such matrices may be formed of materials presently in use for other implanted medical applications.

The choice of matrix material is based on biocompatibility, biodegradability, mechanical properties, cosmetic appearance, and interface properties. The particular application of the compositions will define the appropriate formulation. Potential matrices for the compositions may be biodegradable and chemically defined calcium sulfate, tricalcium phosphate, hydroxyapatite, polylactic acid, polyglycolic acid, and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, alumninates, or other ceramics. Matrices may be comprised of combinations of any of the above-mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

One specific embodiment is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the polypeptide compositions from disassociating from the matrix.

One suitable family of sequestering agents is cellulosic materials such as alkylcelluloses (including hydroxyalkylcelluloses), including methylcellulose, ethylcellulose, hydoxyethylcellulose, hydroxypropylcellulose, hydroxypropylmethylcellulose, and carboxymethylcellulose, one preferred being cationic salts of carboxymethylcellulose (CMC). Other preferred sequestering agents include hyaluronic acid, sodium alginate, poly(ethylene glycol), polyoxyethylene oxide, carboxyvinyl polymer, and poly(vinyl alcohol). The amount of sequestering agent useful herein is 0.5–20 wt%, preferably 1–10 wt. %, based on total formulation weight, which represents the amount necessary to prevent desorption of the polypeptide (or its antagonist) from the polymer matrix and to provide appropriate handling of the composition, yet not so much that the progenitor cells are prevented from infiltrating the matrix, thereby providing the polypeptide (or its antagonist) the opportunity to assist the osteogenic activity of the progenitor cells.

xii. Combination Therapies

The effectiveness of the PRO256 polypeptide or an agonist or antagonist thereof in preventing or treating the disorder in question may be improved by administering the active agent serially or in combination with another agent that is effective for those purposes, either in the same composition or as separate compositions.

For example, for treatment of cardiac hypertrophy, PRO256 polypeptide therapy can be combined with the administration of inhibitors of known cardiac myocyte hypertrophy factors, e.g., inhibitors of α-adrenergic agonists such as phenylephrine; endothelin-1 inhibitors such as BOSENTAN™ and MOXONODIN™; inhibitors to CT-1 (U.S. Pat. No. 5,679,545); inhibitors to LIF; ACE inhibitors; des-aspartate-angiotensin I inhibitors (U.S. Pat. No. 5,773,415), and angiotensin II inhibitors.

For treatment of cardiac hypertrophy associated with hypertension, the PRO256 polypeptide can be administered in combination with β-adrenergic receptor blocking agents, e.g., propranolol, timolol, tertalolol, carteolol, nadolol, betaxolol, penbutolol, acetobutolol, atenolol, metoprolol, or carvedilol; ACE inhibitors, e.g., quinapril, captopril, enalapril, ramipril, benazepril, fosinopril, or lisinopril; diuretics, e.g., chlorothiazide, hydrochlorothiazide, hydroflumethazide, methylchlothiazide, benzthiazide, dichlorphenamide, acetazolamide, or indapamide; and/or calcium channel blockers, e.g., diltiazem, nifedipine, verapamil, or nicardipine. Pharmaceutical compositions comprising the therapeutic agents identified herein by their generic names are commercially available, and are to be administered following the manufacturers' instructions for dosage, administration, adverse effects, contraindications, etc. See, e.g., *Physicians' Desk Reference* (Medical Economics Data Production Co.: Montvale, N.J., 1997), 51th Edition.

Preferred candidates for combination therapy in the treatment of hypertrophic cardiomyopathy are β-adrenergic-blocking drugs (e.g., propranolol, timolol, tertalolol, carteolol, nadolol, betaxolol, penbutolol, acetobutolol, atenolol, metoprolol, or carvedilol), verapamil, difedipine, or diltiazem. Treatment of hypertrophy associated with high blood pressure may require the use of antihypertensive drug therapy, using calcium channel blockers, e.g., diltiazem, nifedipine, verapamil, or nicardipine; β-adrenergic blocking agents; diuretics, e.g., chlorothiazide, hydrochlorothiazide, hydroflumethazide, methylchlothiazide, benzthiazide, dichlorphenamide, acetazolamide, or indapamide; and/or ACE-inhibitors, e.g., quinapril, captopril, enalapril, ramipril, benazepril, fosinopril, or lisinopril.

For other indications, PRO256 polypeptides or their agonists or antagonists may be combined with other agents beneficial to the treatment of the bone and/or cartilage defect, wound, or tissue in question. These agents include various growth factors such as EGF, PDGF, TGF-α or TGF-β, IGF, FGF, and CTGF.

In addition, PRO256 polypeptides or their agonists used to treat cancer may be combined with cytotoxic, chemotherapeutic, or growth-inhibitory agents as identified above. Also, for cancer treatment, the PRO256 polypeptide or agonist thereof is suitably administered serially or in combination with radiological treatments, whether involving irradiation or administration of radioactive substances.

The effective amounts of the therapeutic agents administered in combination with the PRO256 polypeptide or agonist or antagonist thereof will be at the physician's or veterinarian's discretion. Dosage administration and adjustment is done to achieve maximal management of the conditions to be treated. For example, for treating hypertension, these amounts ideally take into account use of diuretics or digitalis, and conditions such as hyper- or hypotension, renal impairment, etc. The dose will additionally depend on such factors as the type of the therapeutic agent to be used and the specific patient being treated. Typically, the amount employed will be the same dose as that used, if the given therapeutic agent is administered without the PRO256 polypeptide.

xiii. Articles of Manufacture

An article of manufacture such as a kit containing the PRO256 polypeptide or agonists or antagonists thereof useful for the diagnosis or treatment of the disorders described above comprises at least a container and a label. Suitable containers include, for example, bottles, vials, syringes, and test tubes. The containers may be formed from a variety of materials such as glass or plastic. The container holds a composition that is effective for diagnosing or treating the condition and may have a sterile access port (for example, the container may be an intravenous solution bag or a vial having a stopper pierceable by a hypodermic injection needle). The active agent in the composition is the PRO256 polypeptide or an agonist or antagonist thereto. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use. The article of manufacture may also comprise a second or third container with another active agent as described above.

E. Antibodies

Some of the most promising drug candidates according to the present invention are antibodies and antibody fragments that may inhibit the production or the gene product of the genes identified herein and/or reduce the activity of the gene products.

i. Polyclonal Antibodies

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO256 polypeptide or a fusion protein thereof. It may be useful to conjugate the immunizing agent to a protein known to be immunogenic in the mammal being immunized. Examples of such immunogenic proteins include, but are not limited to, keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A or synthetic trehalose dicorynomycolate). The immunization protocol may be selected by one skilled in the art without undue experimentation.

ii. Monoclonal Antibodies

The anti-PRO256 antibodies may, alternatively, be monoclonal antibodies. Monoclonal antibodies may be prepared using hybridoma methods, such as those described by Kohler and Milstein, *Nature* 256:495 (1975). In a hybridoma method, a mouse, hamster, or other appropriate host animal is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO256 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice* (New York: Academic Press, 1986), pp. 59–103. Immortalized cell lines are usually transformed mammalian cells, particularly myeloma cells of rodent, bovine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, *J. Immunol.* 133:3001 (1984); Brodeur et al., *Monoclonal Antibody Production Techniques and Applications* (Marcel Dekker, Inc.: New York, 1987) pp. 51–63.

The culture medium in which the hybridoma cells are cultured can then be assayed for the presence of monoclonal antibodies directed against the PRO256 polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods. Goding, supra. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, Protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy- and light-chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using routine techniques known in the art.

iii. Human and Humanized Antibodies

The anti-PRO256 antibodies may further comprise humanized antibodies or human antibodies. Humanized forms of non-human (e.g., murine) antibodies are chimeric immunoglobulins, immunoglobulin chains, or fragments thereof (such as Fv, Fab, Fab', F(ab')$_2$, or other antigen-binding subsequences of antibodies) that contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody preferably also will comprise at least a portion of an immunoglobulin constant region (Fc), typically that of a human immunoglobulin. Jones et al., *Nature* 321: 522–525 (1986); Riechmann et al., *Nature*, 332: 323–329 (1988); Presta, *Curr. Opp. Struct. Biol.*, 2:593–596 (1992).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature*, 321: 522–525 (1986); Riechmann et al., *Nature*, 332: 323–327 (1988); Verhoeyen et al. *Science*, 239: 1534–1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries. Hoogenboom and Winter, *J. Mol. Biol.*, 227: 381 (1991); Marks et al., *J. Mol. Biol.*, 222: 581 (1991). The techniques of Cole et al. and Boerner et al. are also available for the preparation of human monoclonal antibodies. Cole et al., *Monoclonal Antibodies and Cancer Therapy*, Alan R. Liss, p. 77 (1985) and Boerner et al., *J. Immunol.*, 147 (1): 86–95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and in the following scientific publications: Marks et al., *Bio/Technology*, 10: 779–783 (1992); Lonberg et al., *Nature*, 368: 856–859 (1994); Morrison, *Nature*, 368: 812–813 (1994); al., *Nature Biotechnology*, 14:845–851 (1996); Neuberger, *Nature Biotechnology*, 14:826 (1996); Lonberg and Huszar, *Intern. Rev. Immunol.*, 13: 65–93 (1995).

iv. Bispecific Antibodies

Bispecific antibodies are monoclonal, preferably human or humanized, antibodies that have binding specificities for at least two different antigens. In the present case, one of the binding specificities is for the PRO256 polypeptide, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities. Milstein and Cuello, *Nature*, 305: 537–539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10: 3655–3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh et al., *Methods in Enzymology*, 121: 210 (1986).

v. Heteroconjugate Antibodies

Heteroconjugate antibodies are composed of two covalently joined antibodies. Such antibodies have, for example, been proposed to target immune-system cells to unwanted cells (U.S. Pat. No. 4,676,980), and for treatment of HIV infection. WO 91/00360; WO 92/200373; EP 03089. It is contemplated that the antibodies may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

vi. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See, Caron et al., *J. Exp. Med.*, 176: 1191–1195 (1992) and Shopes, *J. Immunol.*, 148: 2918–2922 (1992). Homodimeric antibodies with enhanced anti-tumor activity may also be prepared using heterobifunctional cross-linkers as described in Wolff et al., *Cancer Research*, 53: 2560–2565 (1993). Alternatively, an antibody can be engineered that has dual Fc regions and may thereby have enhanced complement lysis and ADCC capabilities. See, Stevenson et al., *Anti-Cancer Drug Design*, 3: 219–230 (1989).

vii. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}BI$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, WO94/11026.

In another embodiment, the antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

viii. Immunoliposomes

The antibodies disclosed herein may also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl. Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286–288 (1982) via a disulfide-interchange reaction. A chemotherapeutic agent (such as Doxorubicin) is optionally contained within the liposome. See, Gabizon et al., *J. National Cancer Inst.*, 81 (19): 1484 (1989).

ix. Pharmaceutical Compositions of Antibodies

Antibodies specifically binding a PRO256 polypeptide identified herein, as well as other molecules identified by the screening assays disclosed hereinbefore, can be administered for the treatment of various disorders as noted above and below in the form of pharmaceutical compositions.

If the PRO256 polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA* 90: 7889–7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences,* supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

x. Methods of Treatment using the Antibody

It is contemplated that the antibodies to a PRO256 polypeptide may be used to treat various cardiovascular, endothelial, and angiogenic conditions as noted above.

The antibodies are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

Other therapeutic regimens may be combined with the administration of the antibodies of the instant invention as noted above. For example, if the antibodies are to treat cancer, the patient to be treated with such antibodies may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in *Chemotherapy Service,* Ed., M. C. Perry (Williams & Wilkins: Baltimore, Md., 1992). The chemotherapeutic agent may precede, or follow administration of the antibody, or may be given simultaneously therewith. The antibody may be combined with an anti-estrogen compound such as tamoxifen or EVISTA™ or an anti-progesterone such as onapristone (see, EP 616812) in dosages known for such molecules.

If the antibodies are used for treating cancer, it may be desirable also to administer antibodies against other tumor-associated antigens, such as antibodies that bind to one or more of the ErbB2, EGFR, ErbB3, ErbB4, or VEGF receptor(s). These also include the agents set forth above. Also, the antibody is suitably administered serially or in combination with radiological treatments, whether involving irradiation or administration of radioactive substances. Alternatively, or in addition, two or more antibodies binding the same or two or more different antigens disclosed herein may be co-administered to the patient. Sometimes, it may be beneficial also to administer one or more cytokines to the patient. In a preferred embodiment, the antibodies herein are co-administered with a growth-inhibitory agent. For example, the growth-inhibitory agent may be administered first, followed by an antibody of the present invention. However, simultaneous administration or administration of the antibody of the present invention first is also contemplated. Suitable dosages for the growth-inhibitory agent are those presently used and may be lowered due to the combined action (synergy) of the growth-inhibitory agent and the antibody herein.

In one embodiment, vascularization of tumors is attacked in combination therapy. The anti-PRO256 polypeptide antibody and another antibody (e.g., anti-VEGF) are administered to tumor-bearing patients at therapeutically effective doses as determined, for example, by observing necrosis of the tumor or its metastatic foci, if any. This therapy is continued until such time as no further beneficial effect is observed or clinical examination shows no trace of the tumor or any metastatic foci. Then TNF is administered, alone or in combination with an auxiliary agent such as alpha-, beta-, or gamma-interferon, anti-HER2 antibody, heregulin, anti-heregulin antibody, D-factor, interleukin-1 (IL-1), interleukin-2 (IL-2), granulocyte-macrophage colony stimulating factor (GM-CSF), or agents that promote microvascular coagulation in tumors, such as anti-Protein C antibody, anti-Protein S antibody, or C4 b binding protein (see, WO 91/01753, published Feb. 21, 1991), or heat or radiation.

Since the auxiliary agents will vary in their effectiveness, it is desirable to compare their impact on the tumor by matrix screening in conventional fashion. The administration of anti-PRO256 polypeptide antibody and TNF is repeated until the desired clinical effect is achieved. Alternatively, the anti-PRO256 polypeptide antibody is administered together with TNF and, optionally, auxiliary agent(s). In instances where solid tumors are found in the limbs or in other locations susceptible to isolation from the general circulation, the therapeutic agents described herein are administered to the isolated tumor or organ. In other embodiments, a FGF or PDGF antagonist, such as an anti-FGF or an anti-PDGF neutralizing antibody, is administered to the patient in conjunction with the anti-PRO256 polypeptide antibody. Treatment with anti-PRO256 polypeptide antibodies preferably may be suspended during periods of wound healing or desirable neovascularization.

For the prevention or treatment of cardiovascular, endothelial, and angiogenic disorder, the appropriate dosage of an antibody herein will depend on the type of disorder to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

For example, depending on the type and severity of the disorder, about 1 μg/kg to 50 mg/kg (e.g., 0.1–20 mg/kg) of antibody is an initial candidate dosage for administration to the patient, whether, for example, by one or more separate administrations, or by continuous infusion. A typical daily or weekly dosage might range from about 1 µg/kg to 100 mg/kg or more, depending on the factors mentioned above. For repeated administrations over several days or longer, depending on the condition, the treatment is repeated or sustained until a desired suppression of disorder symptoms occurs. However, other dosage regimens may be useful. The progress of this therapy is easily monitored by conventional techniques and assays, including, for example, radiographic tumor imaging.

xi. Articles of Manufacture with Antibodies

An article of manufacture containing a container with the antibody and a label is also provided. Such articles are described above, wherein the active agent is an anti-PRO256 antibody.

xii. Diagnosis and Prognosis of Tumors using Antibodies

If the indication for which the antibodies are used is cancer, while cell-surface proteins, such as growth receptors over expressed in certain tumors, are excellent targets for drug candidates or tumor (e.g., cancer) treatment, the same proteins along with PRO256 polypeptides find additional use in the diagnosis and prognosis of tumors. For example, antibodies directed against the PRO256 polypeptides may be used as tumor diagnostics or prognostics.

For example, antibodies, including antibody fragments, can be used qualitatively or quantitatively to detect the expression of genes including the gene encoding the PRO256 polypeptide. The antibody preferably is equipped with a detectable, e.g., fluorescent label, and binding can be monitored by light microscopy, flow cytometry, fluorimetry, or other techniques known in the art. Such binding assays are performed essentially as described above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent to those skilled in the art that a wide variety of histological methods are readily available for in situ detection.

The following Examples are offered for illustrative purposes only, and are not intended to limit the scope of the present invention in any way.

The disclosures of all patent and literature references cited in the present specification are hereby incorporated by reference in their entirety.

EXAMPLES

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture*, 1987; Coligan et al., *Current Protocols in Immnunology*, 1991.

Example 1

Isolation of cDNA Clones Encoding Human PRO256

The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ®, Incyte Pharmaceuticals, Palo Alto, Calif.). The search was performed using the computer program BLAST or BLAST-2 (Altschul et al., *Methods in Enzymology*, 266: 460–480 (1996)) as a comparison of the ECD protein sequences to a 6 frame translation of the EST sequences. Those comparisons with a BLAST score of 70 (or in some cases, 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

A consensus DNA sequence was assembled relative to other EST sequences using phrap as described above. This assembled consensus sequence is herein identified as DNA28725. Based on the DNA28725 consensus sequence, oligonucleotides were synthesized: 1) to identify by PCR a cDNA library that contained the sequence of interest, and 2) for use as probes to isolate a clone of the full-length coding sequence for PRO256.

A pair of PCR primers (forward and reverse) were synthesized:

```
forward PCR primer:
5'-TGTCCACCAAGCAGACAGAAG-3'  (SEQ ID NO:3)

reverse PCR primer:
5'-ACTGGATGGCGCCTTTCCATG-3'  (SEQ ID NO:4)
```

Additionally, two synthetic oligonucleotide hybridization probes were constructed from the consensus DNA28725 sequence which had the following nucleotide sequences: hybridization probes:

```
5'-CTGACAGTGACTAGCTCAGACCACCCAGAGGACACGGCCAACGTCACAGT-3'   (SEQ ID NO:5)

5'-GGGCTCTTTCCCACGCTGGTACTATGACCCCACGGAGCAGATCTG-3'        (SEQ ID NO:6)
```

In order to screen several libraries for a source of a full-length clone, DNA from the libraries was screened by PCR amplification with the PCR primer pair identified above. A positive library was then used to isolate clones encoding the PRO256 gene using one of the probe oligonucleotides and one of the PCR primers.

RNA for construction of the cDNA libraries was isolated from human placenta tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253: 1278–1280 (1991)) in the unique XhoI and NotI sites.

DNA sequencing of the clones isolated as described above gave the full-length DNA sequence for PRO256, herein designated as DNA35880–1160 [FIG. 1; SEQ ID NO:1] and the derived protein sequence for PRO256.

The entire nucleotide sequence of DNA35880–1160 is shown in FIG. 1 (SEQ ID NO:1). Clone DNA35880-1160 contains a single open reading frame with an apparent translational initiation site at nucleotide positions 188–190 and ending at the stop codon at nucleotide positions 1775–1777. The predicted polypeptide precursor is 529 amino acids long (FIG. 2). Analysis of the full-length PRO256 sequence shown in FIG. 2 (SEQ ID NO:2) evidences the presence of a variety of important polypeptide domains, wherein the locations given for those important polypeptide domains are approximate as described above. Analysis of the full-length PRO256 polypeptide shown in FIG. 2 evidences the presence of the following: a signal peptide from about amino acid 1 to about amino acid 35; a transmembrane domain from about amino acid 466 to about amino acid 483; N-glycosylation sites from about amino acid 66 to about amino acid 70, from about amino acid 235 to about amino acid 239, and from about amino acid 523 to about amino acid 527; N-myristoylation sites from about amino acid 29 to about amino acid 35, from about amino acid 43 to about amino acid 49, from about amino acid 161 to about amino acid 167, from about amino acid 212 to about amino acid 218, from about amino acid 281 to about amino acid 287, from about amino acid 282 to about amino acid 288, from about amino acid 285 to about amino acid 291, from about amino acid 310 to about amino acid 316, from about amino acid 313 to about amino acid 319, from about amino acid 422 to about amino acid 428, from about amino acid 423 to about amino acid 429, and from about amino acid 426 to about amino acid 432; a cell attachment sequence from about amino acid 193 to about amino acid 199; and pancreatic trypsin inhibitor (Kunitz) family signatures from about amino acid 278 to about amino acid 298 and from about amino acid 419 to about amino acid 438. Clone DNA35880–1160 has been deposited with ATCC on Oct. 16, 1997 and is assigned ATCC deposit no. 209379.

Analysis of the amino acid sequence of the full-length PRO256 polypeptide suggests that portions of it possess significant homology to the human bikunin protein, thereby indicating that PRO256 may be a novel proteinase inhibitor.

Example 2

Inhibition of Hepatocyte Growth Factor Activation By PRO256

A time course study of the inhibition of $^{125}$I-single-chain hepatocyte growth factor (scHGF) conversion into its two chain mature HGF form by PRO256 was conducted. In addition, the proteolytic cleavage of single-chain hepatocyte growth factor (scHGF) by kallikrein and inhibition by PRO256 were studied.

The catalytic domain of hepatocyte growth factor activator shares considerable amino acid sequence similarity with other serine proteases including blood coagulation factor XIIa (47%) and plasma kallikrein (37%)(Miyazawa et al., J. Biol. Chem, 268: 10024–10028 (1993)). Factor XIIa can activate single chain HGF in vitro, although the specific activity of factor XIIa is lower than that of HGF activator (Shimomura et al., Eur. J. Biochem, 229:257–261 (1995)). In addition, factor XII has been shown to be activated by plasma kallikrein cleavage (Dunn et al., J. Biol. Chem., 257:1779–1784 (1982)).

Expresson and Purification of Single-chain Hepatocyte Growth Factor (scHGF)

The expression system and purification protocol were carried out in a serum-free medium to avoid single chain HGF activation by serum HGF activator. Serum appears to be the major source of the hepatocyte growth factor activator enzyme (Naka et al., J. Biol. Chem., 267:20114–20119 (1992).

$^{125}$I-labelling of single-chain hepatocyte growth factor (scHGF)

250 µl of a solution of IODO-GEN® (1,3,4,6-tetrachloro-3α, 6α-diphenyl glycoluril) (Pierce Chemical Co., Rockford, Ill.) in chloroform (0.5 mg/ml) was placed into 5 ml borosilicate glass tubes. Solvent was evaporated at room temperature under a steady stream of nitrogen gas and the dried material stored in a dessicator until further use. HGF (700 µg) in 20 mM Hepes. pH 7.2, 150 mM NaCl, 5 mM CaCl$^2$ (HBS buffer) was added to the dried IODO-GEN® material. $^{125}$I-sodium solution (NEN Life Scienecs Inc., Boston, Mass.) was added (5 µCi/µg protein) and the reaction mixture was incubated on ice for 5 mm with gentle swirling. The material was then applied onto a PD-10 column (Pharmacia, Upsala, Sweden) which had been equilibrated with 20 column volumes of HBS buffer. Fractions containing the $^{251}$I-labeled scHGF were collected and pooled. The specific activity was 0.4 µCi/µg scHGF. Analysis by SDS-PAGE under reducing and non-reducing conditions inidicated that less than 10% of the single chain form of HGF has been convened to its two chain form.

Iodinated scHGF was compared with unlabeled scHGF in an activation assay using factor XIIa (20 nM; Haematologic Technologies) as an activator. The time course of scHGF conversion into its two chain form was analyzed by SDS-PAGE followed by autoradiography ($^{125}$I-HGF) or after Coomassie staining (unlabelled HGF). Both labelled and unlabelled HGF were converted identically, suggesting that the iodination of scHGF did not impair processing by its activators, such as factor XIIa.

Activation of $^{125}$I-labelled single chain HGF by human serum

Human serum (ICN Pharmaceuticals) was incubated with different concentrations of PRO256 for 15 min. at 37° C. $^{125}$I-scHGF in HBS buffer was added to start the reaction. The concentrations of $^{125}$I-scHGF and serum in this reaction mixture were 50 µg/ml and 10% serum, respectively. At different time points aliquots were removed and added to sample buffer (Bio-Rad Laboratories, Hercules, Calif.) containing the reducing agent dithiothreitol (BIO-Rad). After a brief heating, samples (approx. 10$^5$ cpm/lane) were loaded onto a 4–20% gradient polyacrylamide gel (Invitrogen Corp., Carlsbad, Calif.). After electrophoresis, the dried gels were exposed on x-ray films (X-OMAT AR, Eastman Kodak Company, Rochester, N.Y.) for 12–24 hrs. Films were developed (Kodak M35A X-OMAT Processor), scanned (Umax S-12, Umax Data Systems, Inc., Fremont, Calif.) and further processed with Adobe V.5.5 Photoshop software (Adobe Systems Inc., San Jose, Calif.).

FIGS. 3a–3b show human serum-mediated conversion of $^{125}$I-scHGF into its two chain form and inhibition of this conversion by PRO256.

FIG. 3a depicts the time course study of inhibition by PRO256 on serum-mediated conversion of $^{125}$I-scHGF into its two chain form. $^{125}$I-scHGF was incubated with human serum (10%) at 37° C. and aliquo taken at different time points were analyzed by SDS-PAGE under reducing conditions. The bands from the top to the bottom of the gel are scHGF, HGF heavy chain (α-chain) and HGF light chains (doublet; β-chain). Left lanes (+) correspond with the presence of PRO256 (1 µM) and right lanes (−) without PRO256. In the presence of the inhibitor PRO256 (at time intervals 0, 0.5 hr, 1 hr, 2 hr, and 4 hr), $^{125}$I-sc-HGF is not converted two chain form as indicated by the top heavy band on the gel. In contrast, in the absence of inhibitor PRO256, serum-mediated conversion of $^{125}$I-scHGH into its two chain form occurs within the 4 hr incubation period.

FIG. 3b depicts the PRO256 concentration-dependent inhibition of serum-mediated $^{125}$I-scHGF activation after 4 hr incubation. Lane C corresponds to uninhibited $^{125}$I-scHGF conversion; lane 0 is time point 0 min; lanes 1–7 correspond to aliquots taken after 4 hr incubation in the presence of decreasing concentrations of inhibitor PRO256 (1.27 µM, 0.42 µM, 0.14 µM, 0.047 µM, 0.016 µM, 0.005 µM, and 0.0017µM).

Proteolytic Cleavage of scHGF by Kallikrein and Inhibition by PRO256

Assays were carried out as described for $^{125}$I-scHGF activation by human serum, except that human kallikrein (Haematologic Technologies, Essex Junction, Vt.) was used instead of serum. Inhibitor PRO256 in HBS buffer was incubated with kallikrein for 15 min at 37° C. before $^{125}$I-scHGF was added. The final concentration of kallikrein, $^{125}$I-scHGF and inhibitor PRO256 in HBS buffer were 40 nM, 50 µg/ml and 1 µM, respectively. Human factor XII proteolytic activity has not been shown to be inhibited by HGF activator inhibitor. Therefore, as a control for the specificity of PRO256, human factor XIIa (F.XIIa; Haematologic Technologies) was used. Experiments were carried out identical to those described for kallikrein.

Inhibition of Kallikrein Enzymatic Activity by PRO256

Human kallikrein was incubated with PRO256 in HBS buffer containing 0.5 mg/ml BSA for 20 min at room temperature. The chromogenic substrate S2305 (Diapharma Group Inc., Columbus, Ohio) was added and the change in absorbance at 405 nm was measured on a kinetic microplate reader (Molecular Devices, Menlo Park, Calif.). The final concentrations of kallikrein and S2305 in this reaction mixture were 1.25 nM and 1.8 mM, respectively.

In a separate experiment, the $K_M$ value of S2305 in this assay system was determined to be 168 µM. Assuming a competitive inhibition mode of PRO256 with respect to the chromogenic substrate S2305, the apparent $K_1$ ($K_1^*$) was calculated according to the equation $K1^* = IC_{50}/(1+(S/K_M))$ (Cheng et al., Biochem. Pharmacol., 22:3099–3109, (1973)), where S is the employed concentration of S2305. (See FIG. 5)

FIGS. 4(a) to 4(b) show inhibiton studies of PRO256 on the proteolytic cleavage of $^{125}$I-scHGF by human kallikrein and human factor XIIa.

FIG. 4a depicts the cleavage of $^{125}$I-scHGF (50 µg/ml) by human kallikrein (40 nM) and inhibition by PRO256 (1 µM). Kallikrein was pre-incubated for 15 min at 37° C. with PRO256 before $^{125}$I-scHGF was added. The reactions were carried out at 37° C. Lanes designated (+) indicate presence of PRO256 and (−) indicate absence of PRO256 (=control). In the presence of PRO256, kallikrein conversion of $^{125}$I-scHGF into its two chain form is inhibited over the 4 hour incubation period compared with the control.

FIG. 4b shows the conversion of $^{125}$I-scHGF by human factor XIIa (40 nM) and the lack of inhibition thereof by PRO256. Factor XIIa was pre-incubated for 15 min at 37° C with PRO256 before $^{125}$I-scHGF was added. The reactions were carried out at 37° C. Lanes designated (+) indicate the presence of PRO256 and (−) the absence of PRO256 (=control). In the presence or absence of PRO256, factor XIIa converts $^{125}$I-scHGF into its two chain form, thereby indicating lack of inhibition by PRO256.

Example 3

Use of PRO256 as a Hybridization Probe

The following method describes use of a nucleotide sequence encoding PRO256 as a hybridization probe.

DNA comprising the coding sequence of full-length or mature PRO256 (as shown in accompanying figures) or a fragment thereof is employed as a probe to screen for homologous DNAs (such as those encoding naturally-occurring variants of PRO256) in human tissue cDNA libraries or human tissue genomic libraries.

Hybridization and washing of filters containing either library DNAs is performed under the following high-stringency conditions. Hybridization of radiolabeled probe derived from the gene encoding PRO256 polypeptide to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence can then be identified using standard techniques known in the art.

Example 4

Expression of PRO256 in E. coli

This example illustrates preparation of an unglycosylated form of PRO256 by recombinant expression in E. coli.

The DNA sequence encoding PRO256 is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see, Bolivar et al., Gene, 2:95 (1977)) which contains genes for ampicillin a tetracycline resistance. The vector is digested with restriction enzyme and dephosphorylated. The PCR amplified sequences are then ligated into the vector. The vector will preferably include sequences which encode for an antibiotic resistance gene, a trp promoter, a poly-His leader (including the first six STII codons, poly-His sequence, and enterokinase cleavage site), the PRO256 coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO256 protein can then be purified using a metal chelating column under conditions that allow tight binding of the protein.

PRO256 may be expressed in E. coli in a poly-His tagged form, using the following procedure. The DNA encoding PRO256 is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an E. coli host based on strain 52 (W3110 fuhA(tonA) lon galE rpoHts(htpRts) clpP(laclq). Transformants are first grown in LB containing 50 mg/ml carbenicillin at 30° C. with shaking until an $OD_{600}$ of 3–5 is reached. Cultures are then diluted 50–100 fold into CRAP media (prepared by mixing 3.57 g $(NH_4)_2SO_4$, 0.71 g sodium citrate·$2H_2O$, 1.07 g KCl, 5.36 g Difco yeast extract, 5.36 g Sheffield hycase SF in 500 ml water, as well as 110 mM MPOS, pH 7.3, 0.55% (w/v) glucose and 7 mM $MgSO_4$) and grown for approximately 20–30 hours at 30° C. with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6–10 g pellets) is resuspended in 10 volumes (w/v) in 7 M guanidine, 20 mM Tris, pH 8 buffer. Solid sodium sulfite and sodium tetrathionate is added to make final concentrations of 0.1 M and 0.02 M, respectively, and the solution is stirred overnight at 4 ° C. This step results in a denatured protein with all cysteine residues blocked by sulfitolization. The solution is centrifuged at 40,000 rpm in a Beckman Ultracentifuge for 30 min. The supernatant is diluted with 3–5 volumes of met al chelate column buffer (6 M guanidine, 20 mM Tris, pH 7.4) and filtered through 0.22 micron filters to clarify. The clarified extract is loaded onto a 5 ml Qiagen $Ni^{2+}$-NTA met al chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12–36 hours. The refolding reaction is quenched by the addition of TFA to a final concentration of 0.4% (pH of approximately 3). Before further purification of the protein, the solution is filtered through a 0.22 micron filter and acetonitrile is added to 2–10% final concentration. The refolded protein is chromatographed on a Poros R1/H reversed phase column using a mobile buffer of 0.1% TFA with elution with a gradient of acetonitrile from 10 to 80%. Aliquots of fractions with $A_{280}$ absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO256 polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 5

Expression of PRO256 in Mammalian Cells

This example illustrates preparation of a potentially glycosylated form of PRO256 by recombinant expression in mammalian cells.

The vector, pRK5 (see EP 307,247, published Mar. 15, 1989), is employed as the expression vector. Optionally, the PRO256 DNA is ligated into pRK5 with selected restriction enzymes to allow insertion of the PRO256 DNA using ligation methods such as described in Sambrook et al., supra. The resulting vector is called pRK5-PRO256.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO256 DNA is mixed with about 1 μg DNA encoding the VA RNA gene [Thimmappaya et al., Cell, 31: 543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10minutes at 25° C. precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of the PRO256 polypeptide. The cultures containing transfected cells may undergo further incubation (in serum free medium) and the medium is tested in selected bioassays.

In an alternative technique, PRO256 may be introduced into 293 cells transiently using the dextran sulfate method described by Somparyrac et al., *Proc. Natl. Acad. Sci.*, 12:7575 (1981). 293 cells are grown to maximal density in a spinner flask and 700 µg pRK5-PRO256 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed PRO256 can then be concentrated and purified by any selected method, such as dialysis and/or column chromatography.

In another embodiment, PRO256 can be expressed in CHO cells. The pRK5-PRO256 can be transfected into CHO cells using known reagents such as $CaPO_4$ or DEAE-dextran. As described above, the cell cultures can be incubated, and the medium replaced with culture medium (alone) or medium containing a radiolabel such as $^{35}S$-methionine. After determining the presence of a PRO256 polypeptide, the culture medium may be replaced with serum free medium. Preferably, the cultures are incubated for about 6 days, and then the conditioned medium is harvested. The medium containing the expressed PRO256 polypeptide can then be concentrated and purified by any selected method.

Epitope-tagged PRO256 may also be expressed in host CHO cells. The PRO256 may be subcloned out of the pRK5 vector. The subclone insert can undergo PCR to fuse in frame with a selected epitope tag such as a poly-His tag into a Baculovirus expression vector. The poly-His tagged PRO256 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO256 can then be concentrated and purified by any selected method, such as by $Ni^{2+}$-chelate affinity chromatography.

PRO256 may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g., extracellular domains) of the respective proteins are fused to an IgG1 constant region sequence containing the hinge, CH2 and CH2 domains and/or as a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used in expression in CHO cells is as described in Lucas et al., *Nucl. Acids Res.*, 24:9 (1774–1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Qiagen), Dosper® or Fugene® (Boehringer Mannheim). The cells are grown as described in Lucas et al., supra. Approximately $3\times10^7$ cells are frozen in an ampule for further growth and production as described below.

The ampules containing the plasmid DNA are thawed by placement into a water bath and mixed by vortexing. The contents are pipetted into a centrifuge tube containing 10 ml of media and centrifuged at 1000 rpm for 5 minutes. The supernatant is aspirated and the cells are resuspended in 10 ml of selective media (0.2 µm filtered PS20 with 5% 0.2 µm diafiltered fetal bovine serum). The cells are then aliquoted into a 100 ml spinner containing 90 ml of selective media. After 1–2 days, the cells are transferred into a 250 ml spinner filled with 150 ml selective growth medium and incubated at 37° C. After another 2–3days, 250 ml, 500 ml and 2000 ml spinners are seeded with $3\times10^5$ cells/ml. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2\times10^6$ cells/ml. On day 0, the cell number and pH is determined. On day 1, the spinner is sampled and sparging with filtered air is commenced. On day 2, the spinner is sampled, the temperature shifted to 33° C., and 30 ml of 500 g/L glucose and 0.6 ml of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability drops below 70%, the cell culture is harvested by centrifugation and filtering through a 0.22 µm filter. The filtrate is either stored at 4° C. or immediately loaded onto columns for purification.

For the poly-His tagged constructs, the proteins are purified using a $Ni^{2+}$-NTA column (Qiagen). Before purification, imidazole is added to the conditioned media to a concentration of 5 mM. The conditioned media is pumped onto a 6 ml $Ni^{2+}$-NTA column equilibrated in 20 mM Hepes, pH 7.4, buffer containing 0.3 M NaCl and 5 mM imidazole at a flow rate of 4–5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which has been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µl of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 6

Expression of PRO256 in Yeast

The following method describes recombinant expression of PRO256 in yeast.

First, yeast expression vectors are constructed for intracellular production or secretion of PRO256 from the ADH2/GAPDH promoter. DNA encoding PRO256 and the promoter is inserted into suitable restriction enzyme sites in the selected plasmid to direct intracellular expression of PRO256. For secretion, DNA encoding PRO256 can be cloned into the selected plasmid, together with DNA encoding the ADH2/GAPDH promoter, a native PRO256 signal peptide or other mammalian signal peptide, or, for example, a yeast alpha-factor or invertase secretory signal/leader sequence, and linker sequences (if needed) for expression of PRO256.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO256 can subsequently be isolated and purified by removing the yeast cells from the fermentation medium by centrifugation and then concentrating the medium using selected cartridge filters. The concentrate containing PRO256 may further be purified using selected column chromatography resins.

Many of the PRO256 polypeptides disclosed herein were successfully expressed as described above.

Example 7

Expression of PRO256 in Baculovirus-Infected Insect Cells

The following method describes recombinant expression in Baculovirus-infected insect cells.

The sequence coding for PRO256 is fused upstream of an epitope tag contained within a baculovirus expression vector. Such epitope tags include poly-His tags and immunoglobulin tags (like Fc regions of IgG). A variety of plasmids may be employed, including plasmids derived from commercially available plasmids such as pVL 393 (Novagen). Briefly, the sequence encoding PRO256 or the desired portion of the coding sequence of PRO256 (such as the sequence encoding the extracellular domain of a transmembrane protein or the sequence encoding the mature protein if the protein is extracellular) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression are performed as described by O'Reilley et al., *Baculovirus expression vectors: A Laboratory Manual,* Oxford: Oxford University Press (1994).

Expressed poly-His tagged PRO256 can then be purified, for example, by $Ni^{2+}$-chelate affinity chromatography as follows. Extracts are prepared from recombinant virus-infected Sf9 cells as described by Rupert et al., *Nature,* 362:175–179 (1993). Briefly, Sf9 cells are washed, resuspended in sonication buffer (25 ml Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 $\mu$m filter. A $Ni^{2+}$-NTA agarose column (commercially available from Qiagen) is prepared with a bed volume of 5 ml, washed with 25 ml of water and equilibrated with 25 ml of loading buffer. The filtered cell extract is loaded onto the column at 0.5 ml per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM imidazole gradient in the secondary wash buffer. One ml fractions are collected and analyzed by SDS-PAGE and silver staining or Western blot with $Ni^{2+}$-NTA conjugated to alkaline phosphatase (Qiagen). Fractions containing the eluted $His_{10}$-tagged PRO256 are pooled and dialyzed against loading buffer.

Alternatively, purification of the IgG tagged (or Fc tagged) PRO256 can be performed using known chromatography techniques, including for instance, Protein A or Protein G column chromatography.

Example 8

Preparation of Antibodies that Bind PRO256

This example illustrates preparation of monoclonal antibodies which can specifically bind the PRO256 polypeptide or an epitope on the PRO256 polypeptide without substantially binding to any other polypeptide or polypeptide epitope.

Techniques for producing the monoclonal antibodies are known in the art and are described, for instance, in Goding, supra. Immunogens that may be employed include purified PRO256, fusion proteins containing PRO256, and cells expressing recombinant PRO256 on the cell surface. Selection of the immunogen can be made by the skilled artisan without undue experimentation.

Mice, such as Balb/c, are immunized with the PRO256 immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO256 antibodies.

After a suitable antibody titer has been detected, the animals "positive" for antibodies can be injected with a final intravenous injection of PRO256. Three to four days later, the mice are sacrificed and the spleen cells are harvested. The spleen cells are then fused (using 35% polyethylene glycol) to a selected murine myeloma cell line such as P3X63Ag0.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO256. Determination of "positive" hybridoma cells secreting the desired monoclonal antibodies against PRO256 is within the skill in the art.

The positive hybridoma cells can be injected intraperitoneally into syngeneic Balb/c mice to produce ascites containing the anti-PRO256 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to Protein A or Protein G can be employed.

Deposit of Material

The following material(s) has/have been deposited with the American Type Culture Collection, 10801 University Blvd., Manassas, Va. 20110–2209, USA (ATCC):

| Material | ATCC Dep. No. | Deposit Date |
| --- | --- | --- |
| DNA385880-1160 | 209379 | Oct. 16, 1997 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc., and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the material(s) on deposit should die or be lost or destroyed when cultivated under suitable conditions, the material(s) will be promptly replaced on notification with another of the same. Availability of the deposited material(s) is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct(s) deposited, since the deposited embodiment(s) is/are intended as single illustration(s) of certain aspects of the invention and any constructs that are functionally equivalent are within the scope of this invention. The deposit of material(s) herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated polypeptide having at least 97% amino acid sequence identity to an amino acid sequence shown as SEQ ID NO:2 and which inhibits human serum-induced cleavage of hepatocyte growth factor.

2. A chimeric molecule comprising a polypeptide of claim 1 fused to a heterologous polypeptide.

3. The chimeric molecule of claim 2, wherein said heterologous polypeptide is an epitope tag sequence.

4. The chimeric molecule of claim 2, wherein said heterologous polypeptide is a Fe region of an immunoglobulin.

5. The polypeptide of claim 1, wherein the sequence identity is 98%.

6. The polypeptide of claim 1, wherein the sequence identity is 99%.

7. The polypeptide of claim 1, wherein the polypeptide is SEQ ID NO:2.

8. An isolated polypeptide having at least 97% amino acid sequence identity to an amino sequence encoded by the full-length coding sequence of the DNA deposited under ATCC accession number 209379 and which inhibits human serum-induced cleavage of hepatocyte growth factor.

9. The polypeptide of claim 8, wherein the sequence identity is 98%.

10. The polypeptide of claim 8, wherein the sequence identity is 99%.

11. The polypeptide of claim 8, wherein the polypeptide is the amino acid encoded by the cDNA insert deposited under ATCC accession number 209379.

12. An isolated polypeptide having at least 97% amino acid sequence identity to the polypeptide shown as SEQ ID NO:2, lacking its associated signal peptide wherein said isolated polypeptide inhibits human serum-induced cleavage of hepatocyte growth factor.

13. The polypeptide of claim 12, wherein the sequence identity is 98%.

14. The polypeptide of claim 12, wherein the sequence identity is 99%.

15. The isolated polypeptide of claim 12, wherein the polypeptide comprises the sequence of SEQ ID NO:2, lacking a signal peptide.

16. An isolated polypeptide having at least 97% amino acid sequence identity to the polypeptide encoded by the full-length coding sequence of the DNA deposited under ATCC accession number 209379, lacking its associated signal peptide wherein said isolated polypeptide inhibits human serum or kallikrein-induced cleavage of hepalocyte growth factor.

17. The polypeptide of claim 16, wherein the sequence identity is 98%.

18. The polypeptide of claim 16, wherein the sequence identity is 99%.

19. The isolated polypeptide of claim 16, wherein the polypeptide is encoded by the full-length coding sequence of the DNA deposited under ATCC accession number 209379, lacking its associated signal peptide.

20. A composition comprising the polypeptide of claim 1 in admixture with a carrier.

21. A composition comprising the polypeptide of claim 8 in admixture with a carrier.

22. A composition comprising the polypeptide of claim 12 in admixture with a carrier.

23. A composition comprising the polypeptide of claim 16 in admixture with a carrier.

24. An article of manufacture comprising:
 (1) The composition of claim 20;
 (2) a container containing said composition; and
 (3) a label affixed to said container, or a package insert included in said container, referring to the use of said composition in the treatment of an cardiovascular, endothelial or angiogenic disorder.

25. An article of manufacture comprising:
 (1) The composition of claim 21;
 (2) a container containing said composition; and
 (3) a label affixed to said container, or is package insert included in said container, referring to the use of said composition in the treatment of an cardiovascular, endothelial or angiogenic disorder.

26. An article of manufacture comprising:
 (1) The composition of claim 22;
 (2) a container containing said composition; and
 (3) a label affixed to said container, or a package insert included in said container, referring to the use of said composition in the treatment of an cardiovascular, endothelial or angiogenic disorder.

27. An article manufacture comprising:
 (1) The composition of claim 23;
 (2) a container containing said composition; and
 (3) a label affixed to said container, or a package insert included in said container, referring to the use of said composition in the treatment of an cardiovascular, endothelial or angiogenic disorder.

* * * * *

UNITED STATES PATENT AND TRADEMARK OFFICE
CERTIFICATE OF CORRECTION

PATENT NO. : 6,800,604 B2
DATED : October 5, 2004
INVENTOR(S) : Austin L. Gurney et al.

It is certified that error appears in the above-identified patent and that said Letters Patent is hereby corrected as shown below:

Column 121,
Line 20, before "region," please delete "Fe" and insert -- Fc --.

Column 122,
Line 37, before "package," please delete "is" and insert -- a --.

Signed and Sealed this

Fifth Day of July, 2005

JON W. DUDAS
*Director of the United States Patent and Trademark Office*